United States Patent
Bisek et al.

(10) Patent No.: US 11,896,671 B2
(45) Date of Patent: Feb. 13, 2024

(54) CONJUGATION METHOD FOR CARRIER-LINKED PRODRUGS

(71) Applicant: Ascendis Pharma A/S, Hellerup (DK)

(72) Inventors: Nicola Bisek, Heidelberg (DE); Samuel Weisbrod, Heidelberg (DE); Kornelia Bigott, Mannheim (DE)

(73) Assignee: ASCENDIS PHARMA A/S, Hellerup (DK)

( * ) Notice: Subject to any disclaimer, the term of this patent is extended or adjusted under 35 U.S.C. 154(b) by 509 days.

(21) Appl. No.: 16/317,689

(22) PCT Filed: Jul. 12, 2017

(86) PCT No.: PCT/EP2017/067548
§ 371 (c)(1),
(2) Date: Jan. 14, 2019

(87) PCT Pub. No.: WO2018/011266
PCT Pub. Date: Jan. 18, 2018

(65) Prior Publication Data
US 2021/0369848 A1  Dec. 2, 2021

(30) Foreign Application Priority Data

Jul. 13, 2016 (EP) .................................. 16179285

(51) Int. Cl.
| | | |
|---|---|---|
| *A61K 47/61* | (2017.01) | |
| *A61K 47/54* | (2017.01) | |
| *A61K 47/64* | (2017.01) | |
| *A61K 47/60* | (2017.01) | |

(52) U.S. Cl.
CPC .......... *A61K 47/545* (2017.08); *A61K 47/542* (2017.08); *A61K 47/60* (2017.08); *A61K 47/61* (2017.08); *A61K 47/64* (2017.08)

(58) Field of Classification Search
CPC ............................ A61K 475/545; A61K 47/61
See application file for complete search history.

(56) References Cited

U.S. PATENT DOCUMENTS

| | | | |
|---|---|---|---|
| 7,585,837 B2 | 9/2009 | Shechter et al. | |
| 8,618,124 B2 | 12/2013 | Greenwald et al. | |
| 8,754,190 B2 | 6/2014 | Ashley et al. | |
| 8,946,405 B2 | 2/2015 | Ashley et al. | |
| 2010/0297021 A1 * | 11/2010 | Wendt ..................... | A61P 13/12 435/69.7 |
| 2012/0035101 A1 | 2/2012 | Fares et al. | |

FOREIGN PATENT DOCUMENTS

| | | |
|---|---|---|
| EP | 1 536 334 | 6/2005 |
| WO | WO 02/089789 | 11/2002 |
| WO | WO 2005/027978 | 3/2005 |
| WO | WO 2005/099768 | 10/2005 |
| WO | WO 2006/003014 | 1/2006 |
| WO | WO 2006/136586 | 12/2006 |
| WO | WO 2008/034122 | 3/2008 |
| WO | WO 2008/155134 | 12/2008 |
| WO | WO 2009/009712 | 1/2009 |
| WO | WO 2009/095479 | 8/2009 |
| WO | WO 2009/143412 | 11/2009 |
| WO | WO 2010/091122 | 8/2010 |
| WO | WO 2011/012715 | 2/2011 |
| WO | WO 2011/012722 | 2/2011 |
| WO | WO 2011/082368 | 7/2011 |
| WO | WO 2011/089214 | 7/2011 |
| WO | WO 2011/089215 | 7/2011 |
| WO | WO 2011/089216 | 7/2011 |
| WO | WO 2011/144756 | 11/2011 |
| WO | WO 2013/024047 | 2/2013 |
| WO | WO 2013/024048 | 2/2013 |
| WO | WO 2013/024052 | 2/2013 |
| WO | WO 2013/024053 | 2/2013 |
| WO | WO 2013/036857 | 3/2013 |
| WO | WO 2013/160340 | 10/2013 |
| WO | WO 2014/056926 | 4/2014 |
| WO | WO 2014/060512 | 4/2014 |
| WO | WO2015/104374 | * 7/2015 ........... C08G 65/337 |
| WO | WO 2015/104374 | 7/2015 |
| WO | WO 2016/110577 | 7/2016 |

OTHER PUBLICATIONS

Noda et al., J'nal of the ACS, vol. 136, No. 15, (2014) pp. 5611-5614.*
Saito et al., ACS Chemical Biology, vol. 10, No. 4 (2015) pp. 1026-1033.*
Hheredia et al., Macromolecules, vol. 40, No. 14, (2007) pp. 4772-4779.*
Dumas, A. M; Bode, J.W., "Synthesis of Acyltrifluoroborates", Org. Lett. (2012), 2138- 2141, 14(8).
Fumito Saito et al, "*Critical Evaluation and Rate Constants of Chemoselective Ligation Reactions for Stoichiometric Conjugations in Water*", ACS Chemical Biology, Apr. 17, 2015, 1026-1033, 10(4), XP55328644.
Herdia K L et al., "*Aminoxy End-Functionalized Polymers Synthesized by ATRP for Chemoselective conjugation to Proteins*", Macromolecules, American Chemical Society, US, Jul. 10, 2007, 4473-4779, 40(14), XP001505999.
Hideotoshi Noda et al., "*Rapid Ligations with Equimolar Reactants in Water with the Potassium Acyltrifluoroborate (KAT) Amide Formation*", Journal of the American Chemical Society, Mar. 31, 2014, 5611-5614, 136(15), XP055325974.

(Continued)

*Primary Examiner* — Paul V Ward

(74) *Attorney, Agent, or Firm* — Andrew T. Wilkins; Sean M. Coughlin; Dechert LLP

(57) ABSTRACT

The present invention relates to reagents comprising a substituted acyl borate or a substituted hydroxylamine, to a method of synthesizing a carrier-linked prodrug using said reagents and to carrier-linked prodrugs obtainable by said method.

24 Claims, No Drawings
Specification includes a Sequence Listing.

(56) References Cited

OTHER PUBLICATIONS

Nicolaou K C et al., "*Combinatorial synthesis through disulphide exchange: discovery of potent psammaplin A type antibacterial agents active against methicillin-resistant Staphylococcus aureus (MRSA)*", Chemistry—A European Journal, Wiley—VCHH Verlag GmbH & Co. KGAA, Weinheim, DE, Oct. 1, 2007, 4280-4295, 7(19), XP009140689.

* cited by examiner

```
                     SEQUENCE LISTING

<160> NUMBER OF SEQ ID NOS: 3

<210> SEQ ID NO 1
<211> LENGTH: 20
<212> TYPE: PRT
<213> ORGANISM: Artificial Sequence
<220> FEATURE:
<223> OTHER INFORMATION: Artificial random coil

<400> SEQUENCE: 1

Gly Gly Pro Gly Gly Pro Gly Pro Gly Gly Pro Gly Gly Pro Gly Pro
1               5                   10                  15

Gly Gly Pro Gly
            20

<210> SEQ ID NO 2
<211> LENGTH: 80
<212> TYPE: PRT
<213> ORGANISM: Artificial Sequence
<220> FEATURE:
<223> OTHER INFORMATION: Artificial random coil

<400> SEQUENCE: 2

Gly Gly Pro Gly Gly Pro Gly Pro Gly Gly Pro Gly Gly Pro Gly Pro
1               5                   10                  15

Gly Gly Pro Gly Gly Gly Pro Gly Gly Pro Gly Pro Gly Gly Pro Gly
            20                  25                  30
```

```
Gly Pro Gly Pro Gly Gly Pro Gly Gly Gly Pro Gly Gly Pro Gly Pro
            35                  40                  45
Gly Gly Pro Gly Gly Pro Gly Pro Gly Gly Pro Gly Gly Gly Pro Gly
        50                  55                  60
Gly Pro Gly Pro Gly Gly Pro Gly Gly Pro Gly Pro Gly Gly Pro Gly
65                  70                  75                  80

<210> SEQ ID NO 3
<211> LENGTH: 38
<212> TYPE: PRT
<213> ORGANISM: Homo sapiens
<220> FEATURE:
<221> NAME/KEY: DISULFID
<222> LOCATION: (22)..(38)

<400> SEQUENCE: 3

Leu Gln Glu His Pro Asn Ala Arg Lys Tyr Lys Gly Ala Asn Lys Lys
1               5                   10                  15
Gly Leu Ser Lys Gly Cys Phe Gly Leu Lys Leu Asp Arg Ile Gly Ser
            20                  25                  30
Met Ser Gly Leu Gly Cys
            35
```

CONJUGATION METHOD FOR CARRIER-LINKED PRODRUGS

The present invention relates to reagents comprising a substituted acyl borate or a substituted hydroxylamine, to a method of synthesizing a carrier-linked prodrug using said reagents and to carrier-linked prodrugs obtainable by said method.

To improve physicochemical or pharmacokinetic properties of a drug in vivo such drug can be conjugated to a carrier. Typically, carriers in drug delivery are either used in non-covalent complexation of drug and carrier, or by covalent attachment of a carrier reagent to one of the drug's functional groups.

However, the non-covalent approach requires a highly efficient drug-carrier complexation to prevent uncontrolled, burst-type release of the drug due to disintegration of the drug-carrier complex after administration. Restraining the diffusion of an unbound, water soluble drug molecule requires strong van der Waals contacts, frequently mediated through hydrophobic moieties and charged moieties for electrostatic binding. Many conformationally sensitive drugs, such as proteins or peptides, are rendered dysfunctional during the complexation process and/or during subsequent storage of the non-covalently bound drug.

Alternatively, a drug may be covalently conjugated to a carrier via a stable linker or a reversible prodrug linker moiety from which the drug is released. If the drug is stably connected to the carrier, such a conjugate needs to exhibit sufficient residual activity to have a pharmaceutical effect, thus the conjugate is constantly in an active form.

If the drug is conjugated to the carrier through a reversible prodrug linker, such conjugates are referred to as carrier-linked prodrugs. The advantage of this approach is that no residual activity of the conjugate is needed, because the drug exhibits its pharmacological effect upon release from the conjugate. A carrier-linked prodrug may exhibit no or little drug activity, i.e. the carrier-linked prodrug is pharmacologically inactive. This approach is applied to various classes of molecules, from so-called small molecules, to natural products and up to large proteins.

The biologically active moiety of such a carrier-linked prodrug can be released by enzymatic or non-enzymatic cleavage of the linkage between the carrier and the biologically active moiety, or by a sequential combination of both. However, enzyme-dependence is usually less preferred, because enzyme levels may vary significantly between patients and that makes the correct dosing difficult.

The synthesis of such carrier-linked prodrugs may be challenging, because reagents may be toxic, may have slow rate constants or the functional groups of the reagents may react unspecifically. For example, when using the commonly known thiol-maleimide chemistry the maleimide reagent may react with other thiols present in for example a peptide or protein. Also, the thiol-maleimide chemistry is preferably performed at neutral pH which may not be ideal for certain proteins and peptides. However, changing the reaction pH may have a negative impact on conjugation speed and efficiency.

A neutral pH is also not ideal for the synthesis of prodrugs, such as carrier-linked prodrugs, especially if the reversible bond between the reversible prodrug linker moiety and the biologically active moiety is already present in the step involving the thiol-maleimide conjugation, because the reversible bond may start hydrolyzing at a neutral pH. Therefore, such step in the synthesis of a carrier-linked prodrug is preferably performed at a lower or higher pH to keep the reversible linkage between the biologically active moiety and the reversible prodrug linker moiety intact, which, however, depending on the conjugation chemistry used slows down the reaction, which is also not desirable.

WO 2015/104374 A1 describes a conjugation method suitable for conjugating acyl borates substituted poly(ethylene glycol) (PEG) moieties to hydroxylamine containing macromolecules which conjugation chemistry, however, was exclusively restricted to PEG and was only used to form stable PEG conjugates, which stable conjugates have the disadvantages as described above (need for residual activity). Stable conjugates also do not suffer from the same difficulties as carrier-linked prodrugs, because the linkage between the biologically active moiety and the remainder of the conjugate is stable. Therefore, stable conjugates do not risk that a linkage starts hydrolyzing during later synthesis steps.

As PEG is only one of many types of molecules widely used as carrier for prodrugs and as it is advantageous to reversibly conjugate a drug to a carrier rather than having a stable linkage between the drug and the carrier, a similar chemoselective conjugation method is required for making carrier-linked prodrugs.

Therefore, there is a need for an alternative chemoselective conjugation method for the synthesis of carrier-linked prodrugs which at least partially overcomes the above-described shortcomings.

It is therefore an object of the present invention to at least partially overcome this shortcoming.

This objective is achieved with certain reagents described herein and their use in a method of synthesis.

In a first aspect, the present invention relates to a reagent of formula (I)

wherein
-D is a biologically active moiety;
each -L$^1$- is independently a reversible prodrug linker;
each -L$^2$- is independently a chemical bond or a spacer;
each -A is —X$^0$ or —Y$^0$;
a is selected from the group consisting of 1, 2, 3, 4, 5, 6, 7 or 8;
—X$^0$ is a substituted acyl borate; and
—Y$^0$ is a substituted hydroxylamine.

In a second aspect the present invention relates to a reagent of formula (II))

wherein
—Z is a carrier;
-L$^{2'}$- is a chemical bond or a spacer;
—B$^0$ is selected from the group consisting of —X$^0$ and —Y$^0$;
b is an integer of at least 1;
—X$^0$ is a substituted acyl borate; and
—Y$^0$ is a substituted hydroxylamine.

In a third aspect the present invention relates to a method of synthesizing a carrier-linked prodrug, the method comprising the step of reacting a reagent of formula (I) under aqueous conditions with a reagent of formula (II), with one of -A and —B$^0$ being —X$^0$ and the other one being —Y$^0$, and forming an amide bond between a moiety -A and a moiety —B$^0$.

In a forth aspect the present invention relates to a carrier-linked prodrug obtainable by the method of the present invention.

It was surprisingly found that substituted acyl borates and substituted hydroxylamines can also be used for the synthesis of carrier-linked prodrugs and that such carrier-linked prodrugs show near quantitative release of the drug.

Within the present invention the terms are used having the meaning as follows.

The term "drug" as used herein refers to a substance used in the treatment, cure, prevention, or diagnosis of a disease or used to otherwise enhance physical or mental well-being. If a drug D-H is conjugated to another moiety, the moiety -D of the resulting product that originated from the drug is referred to as "biologically active moiety".

As used herein the term "carrier-linked prodrug" refers to a biologically active moiety reversibly and covalently connected to a specialized protective group, i.e. the "carrier", through a reversible prodrug linker moiety. Said reversible prodrug linker moiety is a linker or "spacer" moiety comprising a reversible linkage with the biologically active moiety. The specialized protective group, i.e. the carrier, alters or eliminates undesirable properties in the parent molecule. This also includes the enhancement of desirable properties in the drug and the suppression of undesirable properties. A carrier-linked prodrug releases the reversibly and covalently bound biologically active moiety -D in the form of its corresponding drug D-H. In other words, a prodrug is a conjugate comprising a biologically active moiety which is covalently and reversibly conjugated to a carrier moiety via a reversible prodrug linker moiety, which covalent and reversible conjugation of the carrier to the reversible prodrug linker moiety is either directly or through a spacer, such as -$L^2$-. Such conjugate releases the formerly conjugated biologically active moiety in the form of a free drug.

A "biodegradable linkage" or a "reversible linkage" is a linkage that is hydrolytically degradable, i.e. cleavable, in the absence of enzymes under physiological conditions (aqueous buffer at pH 7.4, 37° C.) with a half-life ranging from one hour to three months, preferably from one hour to two months, most preferably from one hour to one month. Accordingly, a "stable linkage" is a linkage having a half-life under physiological conditions (aqueous buffer at pH 7.4, 37° C.) of more than three months.

Accordingly, a "reversible prodrug linker moiety" is a moiety which is covalently conjugated to a biologically active moiety through a reversible linkage and is also covalently conjugated to a carrier moiety, such as —Z, wherein the covalent conjugation to said carrier moiety is either directly or through a spacer moiety, such as -$L^2$-. Preferably the linkage between —Z and -$L^2$- is a stable linkage.

As used herein, the term "traceless prodrug linker" means a reversible prodrug linker which upon cleavage releases the drug in its free form. As used herein, the term "free form" of a drug means the drug in its unmodified, pharmacologically active form.

As used herein, the term "reagent" means a chemical compound which comprises at least one functional group for reaction with the functional group of another chemical compound or drug. It is understood that a drug comprising a functional group (such as a primary or secondary amine or hydroxyl functional group) is also a reagent.

As used herein, the term "moiety" means a part of a molecule, which lacks one or more atoms compared to the corresponding reagent. If, for example, a reagent of the formula "H—X—H" reacts with another reagent and becomes part of the reaction product, the corresponding moiety of the reaction product has the structure "H—X—" or "—X—", whereas each "—" indicates attachment to another moiety. Accordingly, a biologically active moiety is released from a prodrug as a drug.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N($R^1$)—" can be attached to two moieties or interrupting a moiety either as "—C(O)N($R^1$)—" or as "—N($R^1$)C(O)—".

As used herein, the term "functional group" means a group of atoms which can react with other groups of atoms. Functional groups include but are not limited to the following groups: carboxylic acid (—(C=O)OH), primary or secondary amine (—$NH_2$, —NH—), maleimide, thiol (—SH), sulfonic acid (—(O=S=O)OH), carbonate, carbamate (—O(C=O)N<), hydroxyl (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, sulfonamides, sulfuric acid, vinyl sulfone, vinyl ketone, diazoalkane, oxirane, and aziridine.

In case the carrier-linked prodrugs of the present invention comprise one or more acidic or basic groups, the invention also comprises their corresponding pharmaceutically or toxicologically acceptable salts, in particular their pharmaceutically utilizable salts. Thus, the carrier-linked prodrugs of the present invention comprising acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Carrier-linked prodrugs of the present invention comprising one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the carrier-linked prodrugs of the present invention simultaneously comprise acidic and basic groups, the invention also includes, in addition to the salt forms mentioned, inner salts or betaines (zwitterions). The respective salts can be obtained by customary methods which are known to the person skilled in the art like, for example by contacting these prodrugs with an organic or inorganic acid or base in a solvent or dispersant, or by anion exchange or cation exchange with other salts. The present invention also includes all salts of the carrier-linked prodrugs of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means a substance that does not cause harm when administered to a patient and preferably means approved by a regulatory agency, such as the EMA (Europe) and/or the FDA (US) and/or any other national regulatory agency for use in animals, preferably for use in humans.

As used herein the term "about" in combination with a numerical value is used to indicate a range ranging from and including the numerical value plus and minus no more than 10% of said numerical value, more preferably no more than 8% of said numerical value, even more preferably no more than 5% of said numerical value and most preferably no more than 2% of said numerical value. For example, the phrase "about 200" is used to mean a range ranging from and including 200+/−10%, i.e. ranging from and including 180 to 220; preferably 200+/−8%, i.e. ranging from and including 184 to 216; even more preferably ranging from and including 200+/−5%, i.e. ranging from and including 190 to 210; and most preferably 200+/−2%, i.e. ranging from and including 196 to 204. It is understood that a percentage given as "about 20%" does not mean "20%+/−10%", i.e. ranging from and including 10 to 30%, but "about 20%" means ranging from and including 18 to 22%, i.e. plus and minus 10% of the numerical value which is 20.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical groups and/or moieties, such as, for example, one or more functional groups. Preferably, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it preferable has a molecular weight of at most 1000 kDa, such as at most 750 kDa, such as at most 500 kDa, such as at most 300 kDa, such as at most 200 kDa, such as at most 100 kDa. It is understood that also a protein is a polymer in which the amino acids are the repeating structural units, even though the side chains of each amino acid may be different. It is further understood that in the case of a water-insoluble polymer, such as a hydrogel, no meaningful upper limit for the molecular weight can be provided.

As used herein, the term "polymeric" means a reagent or a moiety comprising one or more polymers or polymer moieties. A polymeric reagent or moiety may optionally also comprise one or more other moieties, which are preferably selected from the group consisting of:
$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and
linkages selected from the group comprising

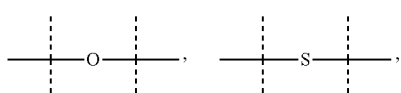

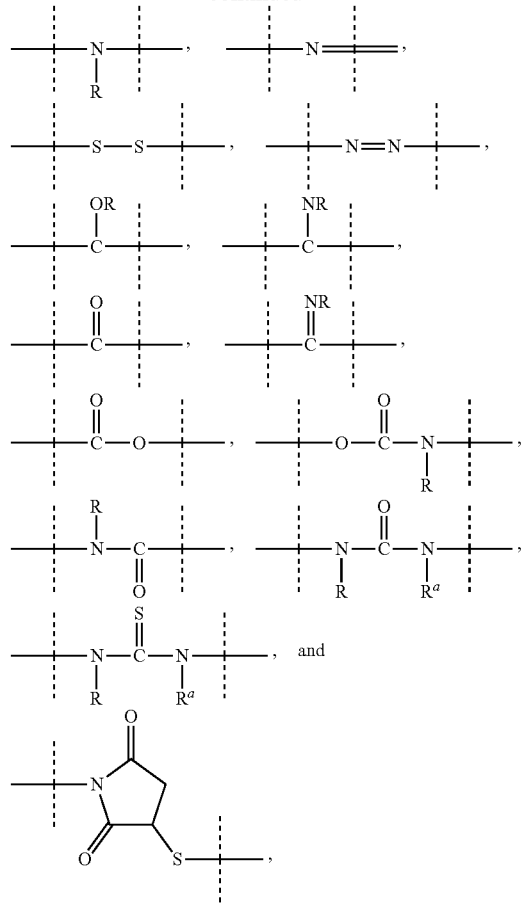

wherein
dashed lines indicate attachment to the remainder of the moiety or reagent, and
—R and —$R^a$ are independently of each other selected from the group consisting of —H, methyl, ethyl, propyl, butyl, pentyl and hexyl.

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers, i.e. to the arithmetic mean of the molecular weight of the polymer or polymeric moiety and the arithmetic mean of the number of monomers of the polymer or polymeric moiety.

Accordingly, in a polymeric moiety comprising "x" monomer units any integer given for "x" therefore corresponds to the arithmetic mean number of monomers. Any range of integers given for "x" provides the range of integers in which the arithmetic mean numbers of monomers lies. An integer for "x" given as "about x" means that the arithmetic mean numbers of monomers lies in a range of integers of x+/−10%, preferably x+/−8%, more preferably x+/−5% and most preferably x+/−2%.

As used herein, the term "number average molecular weight" means the ordinary arithmetic mean of the molecular weights of the individual polymers.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity.

As used herein the term "water-soluble" with reference to a carrier means that when such carrier is part of a conjugate of the present invention at least 1 g of the conjugate comprising such water-soluble carrier can be dissolved in one liter of water at 20° C. to form a homogeneous solution. Accordingly, the term "water-insoluble" with reference to a carrier means that when such carrier is part of the conjugate of the present invention less than 1 g of the conjugate comprising such water-insoluble carrier can be dissolved in one liter of water at 20° C. to form a homogeneous solution.

As used herein, the term "PEG-based" in relation to a moiety or reagent means that said moiety or reagent comprises PEG. Preferably, a "PEG-based moiety" or reagent comprises at least 10% (w/w) PEG, such as at least 20% (w/w) PEG, such as at least 30% (w/w) PEG, such as at least 40% (w/w) PEG, such as at least 50% (w/w), such as at least 60% (w/w) PEG, such as at least 70% (w/w) PEG, such as at least 80% (w/w) PEG, such as at least 90% (w/w) PEG, such as at least 95% (w/w). The remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

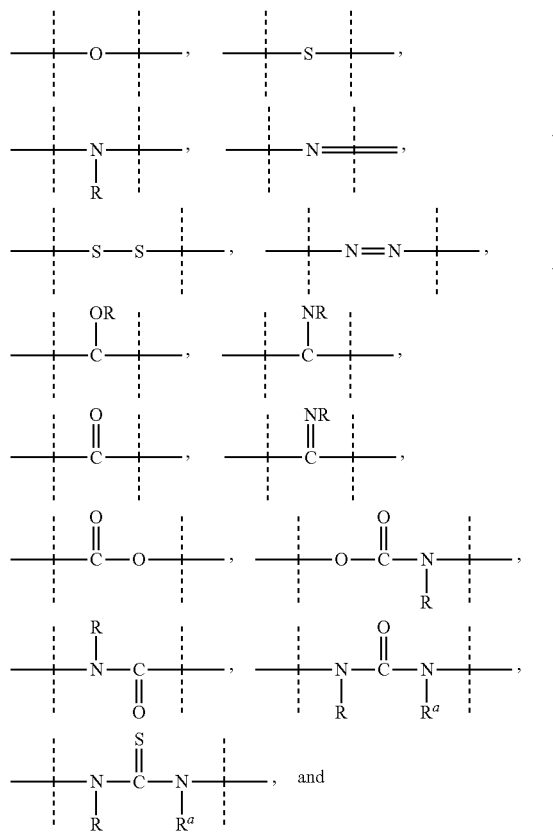

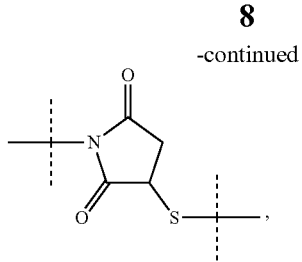

wherein dashed lines indicate attachment to the remainder of the moiety or reagent, and —R and —$R^a$ are independently of each other selected from the group consisting of —H, methyl, ethyl, propyl, butyl, pentyl and hexyl.

As used herein, the term "PEG-based comprising at least X % PEG" in relation to a moiety or reagent means that said moiety or reagent comprises at least X % (w/w) ethylene glycol units (—$CH_2CH_2O$—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

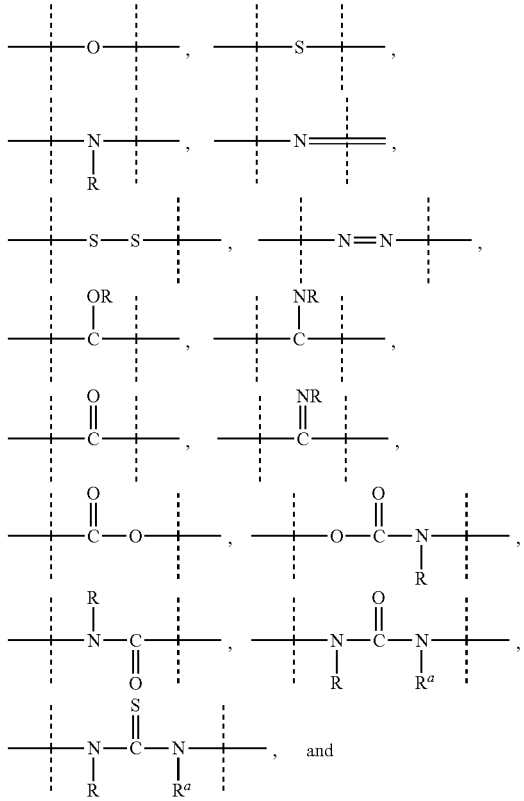

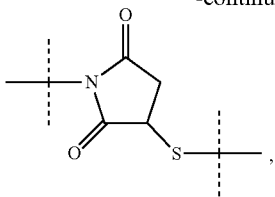

wherein
  dashed lines indicate attachment to the remainder of the moiety or reagent, and
  —R and —$R^a$ are independently of each other selected from the group consisting of —H, methyl, ethyl, propyl, butyl, pentyl and hexyl.

The terms "hyaluronic acid-based" and "hyaluronic acid-based comprising at least X % hyaluronic acid" are used accordingly.

The term "substituted" as used herein means that one or more —H atoms of a molecule or moiety are replaced by a different atom or a group of atoms, which are referred to as "substituent".

Preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

—R$^{x1}$, —R$^{x1a}$, —R$^{x1b}$ are independently of each other selected from the group consisting of —H, -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different;

each —R$^{x3}$, —R$^{x3a}$, —R$^{x4}$, —R$^{x4a}$, —R$^{x4b}$ is independently selected from the group consisting of —H and C$_{1-6}$ alkyl; wherein C$_{1-6}$ alkyl is optionally substituted with one or more halogen, which are the same or different.

More preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-10}$ alkyl, C$_{2-10}$ alkenyl, and C$_{2-10}$ alkynyl; wherein -T$^0$, C$_{1-10}$ alkyl, C$_{2-10}$ alkenyl, and C$_{2-10}$ alkynyl are optionally substituted with one or more —R$^{x2}$, which are the same or different and wherein C$_{1-10}$ alkyl, C$_{2-10}$ alkenyl, and C$_{2-10}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —R$^{x1}$, —R$^{x1a}$, —R$^{x1b}$, —R$^{x3}$, —R$^{x3a}$ is independently selected from the group consisting of —H, halogen, C$_{1-6}$ alkyl, C$_{2-6}$ alkenyl, and C$_{2-6}$ alkynyl;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different;

each —R$^{x4}$, —R$^{x4a}$, —R$^{x4b}$ is independently selected from the group consisting of —H, halogen, C$_{1-6}$ alkyl, C$_{2-6}$ alkenyl, and C$_{2-6}$ alkynyl.

Even more preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-6}$ alkyl, C$_{2-6}$ alkenyl, and C$_{2-6}$ alkynyl; wherein -T$^0$, C$_{1-6}$ alkyl, C$_{2-6}$ alkenyl, and C$_{2-6}$ alkynyl are optionally substituted with one or more —R$^{x2}$, which are the same or different and wherein C$_{1-6}$ alkyl, C$_{2-6}$ alkenyl, and C$_{2-6}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —$R^{x1}$, —$R^{x1a}$, —$R^{x1b}$, —$R^{x2}$, —$R^{x3}$, —$R^{x3a}$ is independently selected from the group consisting of —H, halogen, $C_{1-6}$ alkyl, $C_{2-6}$ alkenyl, and $C_{2-6}$ alkynyl;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{x2}$, which are the same or different.

Preferably, a maximum of 6 —H atoms of an optionally substituted molecule or moiety are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

The term "interrupted" means that a moiety is inserted between two carbon atoms or—if the insertion is at one of the moiety's ends—between a carbon or heteroatom and a hydrogen atom.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are —$CH_2$—, —$CH_2$—$CH_2$—, —$CH(CH_3)$—, —$CH_2$—$CH_2$—$CH_2$—, —$CH(C_2H_5)$—, —$C(CH_3)_2$—. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —$CH_2$—, —$CH_2$—$CH_2$—, —$CH(CH_3)$—, —$CH_2$—$CH_2$—$CH_2$—, —$CH(C_2H_5)$— and —$C(CH_3)_2$—. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl", "$C_{8-24}$ alkyl" or "$C_{1-50}$ alkyl" means an alkyl chain having 1 to 10, 1 to 20, 8 to 24 or 1 to 50 carbon atoms, respectively, wherein each hydrogen atom of the $C_{1-10}$, $C_{1-20}$, $C_{8-24}$ or $C_{1-50}$ carbon may optionally be replaced by a substituent as defined above. Optionally, a $C_{1-10}$, $C_{1-20}$, $C_{8-24}$ or $C_{1-50}$ alkyl may be interrupted by one or more moieties as defined below.

Accordingly, as used herein, the term "$C_6$ alkyl" alone or in combination means a straight-chain or branched alkyl moiety having 6 carbon atoms.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —CH=$CH_2$, —CH=CH—$CH_3$, —$CH_2$—CH=$CH_2$, —CH=CH—$CH_2$—$CH_3$ and —CH=CH—CH=$CH_2$. When two moieties of a molecule are linked by the $C_{2-6}$ alkenyl group, then an example for such $C_{2-6}$ alkenyl is —CH=CH—. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means straight-chain or branched hydrocarbon moiety comprising at least one carbon-carbon triple bond having 2 to 6 carbon atoms. If present at the end of a molecule, examples are —C≡CH, —$CH_2$—C≡CH, $CH_2$—$CH_2$—C≡CH and $CH_2$—C≡C—$CH_3$. When two moieties of a molecule are linked by the alkynyl group, then an example is —C≡C—. Each hydrogen atom of a $C_{2-6}$ alkynyl group may optionally be replaced by a substituent as defined above. Optionally, one or more double bonds may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bonds may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkynyl or $C_{2-50}$ alkynyl may optionally be interrupted by one or more moieties which are preferably selected from the group consisting of

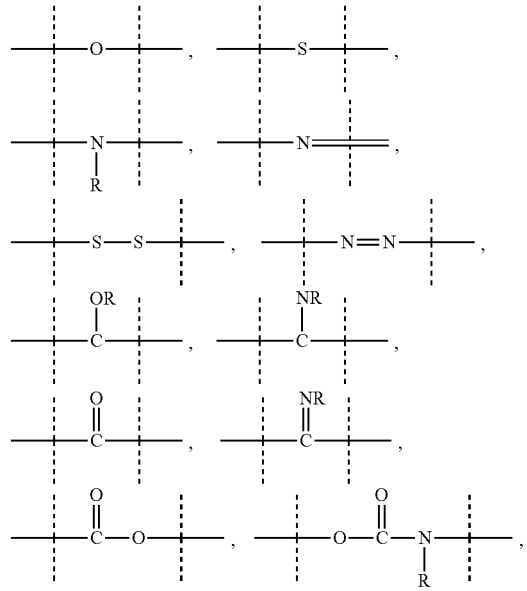

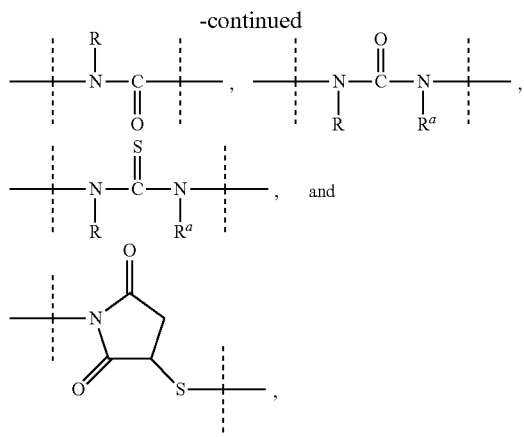

wherein
dashed lines indicate attachment to the remainder of the moiety or reagent; and
—R and —R$^a$ are independently of each other selected from the group consisting of —H, methyl, ethyl, propyl, butyl, pentyl and hexyl.

As used herein, the term "C$_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a C$_{3-10}$ cycloalkyl carbon may be replaced by a substituent as defined above. The term "C$_{3-10}$ cycloalkyl" also includes bridged bicycles like norbornane or norbornene.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of boron, sulfur (including —S(O)—, —S(O)$_2$—), oxygen and nitrogen (including =N$^+$(O)—), preferably of boron, nitrogen and oxygen, and wherein the ring is linked to the rest of the molecule via a boron atom, if the 3- to 10-membered heterocyclyl is used in connection with —X$^0$. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

—R$^{x1}$, —R$^{x1a}$, —R$^{x1b}$ are independently of each other selected from the group consisting of —H, -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different;

each —R$^{x3}$, —R$^{x3a}$, —R$^{x4}$, —R$^{x4a}$, —R$^{x4b}$ is independently selected from the group consisting of —H and C$_{1-6}$ alkyl; wherein C$_{1-6}$ alkyl is optionally substituted with one or more halogen, which are the same or different.

More preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-10}$ alkyl, C$_{2-10}$ alkenyl, and C$_{2-10}$ alkynyl; wherein -T$^0$, C$_{1-10}$ alkyl, C$_{2-10}$ alkenyl, and C$_{2-10}$ alkynyl are optionally substituted with one or more —$R^{x2}$, which are the same or different and wherein $C_{1-10}$ alkyl, $C_{2-10}$ alkenyl, and $C_{2-10}$ alkynyl are optionally interrupted by one or more groups selected from the group consisting of -$T^0$-, —C(O)O—, —O—, —C(O)—, —C(O)N($R^{x3}$)—, —S(O)$_2$N($R^{x3}$)—, —S(O)N($R^{x3}$)—, —S(O)$_2$—, —S(O)—, —N($R^{x3}$)S(O)$_2$N($R^{x3a}$)—, —S—, —N($R^{x3}$)—, —OC(O$R^{x3}$)($R^{x3a}$)—, —N($R^{x3}$)C(O)N($R^{x3a}$)—, and —OC(O)N($R^{x3}$)—;

each —$R^{x1}$, —$R^{x1a}$, —$R^{x1b}$, —$R^{x3}$, —$R^{x3a}$ is independently selected from the group consisting of —H, halogen, $C_{1-6}$ alkyl, $C_{2-6}$ alkenyl, and $C_{2-6}$ alkynyl;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{x2}$, which are the same or different;

each —$R^{x2}$ is independently selected from the group consisting of halogen, —CN, oxo (=O), —COO$R^{x4}$, —O$R^{x4}$, —C(O)$R^{x4}$, —C(O)N($R^{x4}R^{x4a}$), —S(O)$_2$N($R^{x4}R^{x4a}$), —S(O)N($R^{x4}R^{x4a}$), —S(O)$_2R^{x4}$, —S(O)$R^{x4}$, —N($R^{x4}$)S(O)$_2$N($R^{x4a}R^{x4b}$), —S$R^{x4}$, —N($R^{x4}R^{x4a}$), —NO$_2$, —OC(O)$R^{x4}$, —N($R^{x4}$)C(O)$R^{x4a}$, —N($R^{x4}$)S(O)$_2R^{x4a}$, —N($R^{x4}$)S(O)$R^{x4a}$, —N($R^{x4}$)C(O)O$R^{x4a}$, —N($R^{x4}$)C(O)N($R^{x4a}R^{x4b}$), —OC(O)N($R^{x4}R^{x4a}$), and $C_{1-6}$ alkyl; wherein $C_{1-6}$ alkyl is optionally substituted with one or more halogen, which are the same or different;

each —$R^{x4}$, —$R^{x4a}$, —$R^{x4b}$ is independently selected from the group consisting of —H, halogen, $C_{1-6}$ alkyl, $C_{2-6}$ alkenyl, and $C_{2-6}$ alkynyl;

Even more preferably, the one or more further optional substituents are independently of each other selected from the group consisting of halogen, —CN, —COO$R^{x1}$, —O$R^{x1}$, —C(O)$R^{x1}$, —C(O)N($R^{x1}R^{x1a}$), —S(O)$_2$N($R^{x1}R^{x1a}$), —S(O)N($R^{x1}R^{x1a}$), —S(O)$_2R^{x1}$, —S(O)$R^{x1}$, —N($R^{x1}$)S(O)$_2$N($R^{x1a}R^{x1b}$), —S$R^{x1}$, —N($R^{x1}R^{x1a}$), —NO$_2$, —OC(O)$R^{x1}$, —N($R^{x1}$)C(O)$R^{x1a}$, —N($R^{x1}$)S(O)$_2R^{x1a}$, —N($R^{x1}$)S(O)$R^{x1a}$, —N($R^{x1}$)C(O)O$R^{x1a}$, —N($R^{x1}$)C(O)N($R^{x1a}R^{x1b}$), —OC(O)N($R^{x1}R^{x1a}$), -$T^0$, $C_{1-6}$ alkyl, $C_{2-6}$ alkenyl, and $C_{2-6}$ alkynyl; wherein -$T^0$, $C_{1-6}$ alkyl, $C_{2-6}$ alkenyl, and $C_{2-6}$ alkynyl are optionally substituted with one or more —$R^{x2}$, which are the same or different and wherein $C_{1-6}$ alkyl, $C_{2-6}$ alkenyl, and $C_{2-6}$ alkynyl are optionally interrupted by one or more groups selected from the group consisting of -$T^0$-, —C(O)O—, —O—, —C(O)—, —C(O)N($R^{x3}$)—, —S(O)$_2$N($R^{x3}$)—, —S(O)N($R^{x3}$)—, —S(O)$_2$—, —S(O)—, —N($R^{x3}$)S(O)$_2$N($R^{x3a}$)—, —S—, —N($R^{x3}$)—, —OC(O$R^{x3}$)($R^{x3a}$)—, —N($R^{x3}$)C(O)N($R^{x3a}$)—, and —OC(O)N($R^{x3}$)—;

each —$R^{x1}$, —$R^{x1a}$, —$R^{x1b}$, —$R^{x2}$, —$R^{x3}$, —$R^{x3a}$ is independently selected from the group consisting of —H, halogen, $C_{1-6}$ alkyl, $C_{2-6}$ alkenyl, and $C_{2-6}$ alkynyl;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{x2}$, which are the same or different.

Preferably, a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

The term "8- to 30-membered heteropolycyclyl" or "8- to 30-membered heteropolycycle" means a cyclic moiety of two or more rings with 8 to 30 ring atoms which ring atoms comprise at least one heteroatom, wherein two neighboring rings share at least one ring atom, each ring may contain up to the maximum number of double bonds (aromatic or non-aromatic ring which is fully, partially or un-saturated) and wherein the ring is linked to the rest of the molecule via a boron atom, if the 8- to 30-membered heteropolycyclyl is used in connection with —$X^0$. Preferably an 8- to 30-membered heteropolycyclyl comprises no more than 10 heteroatoms, even more preferably no more than 9 heteroatoms, even more preferably no more than 8 heteroatoms, even more preferably no more than 7 heteroatoms, even more preferably no more than 6 heteroatoms, even more preferably no more than 5 heteroatoms and most preferably no more than 4 heteroatoms. Preferably the heteroatoms are selected from the group consisting of boron, sulfur (including —S(O)—, —S(O)$_2$—), oxygen and nitrogen (including =$N^+$(O)—), most preferably boron, oxygen and nitrogen. Preferably an 8- to 30-membered heteropolycyclyl means a cyclic moiety of two, three, four or five rings, more preferably of two, three or four rings.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). Preferably a 8- to 30-membered carbopolycyclyl means a cyclic moiety of two, three, four or five rings, more preferably of two, three or four rings.

As used herein, "halogen" means fluoro, chloro, bromo or iodo. It is generally preferred that halogen is fluoro or chloro.

The term "peptide" as used herein refers to a chain of at least 2 and up to and including 50 amino acid monomer moieties linked by peptide (amide) linkages. The term "peptide" also includes peptidomimetics, such as D-peptides, peptoids or β-peptides, and covers such peptidomimetic chains with up to and including 50 monomer moieties.

The term "peptide nucleic acids" refers to organic polymers having a peptidic backbone, i.e. a backbone in which the monomers are connected to each other through peptide linkages, to which nucleobases, preferably adenine, cytosine, guanine, thymine and uracil, are attached. A preferred backbone comprises N-(2-aminoethyl)-glycine.

As used herein, the term "protein" refers to a chain of more than 50 amino acid monomer moieties linked by peptide linkages, in which preferably no more than 12000 amino acid monomers are linked by peptide linkages, such as no more than 10000 amino acid monomer moieties, no more than 8000 amino acid monomer moieties, no more than 5000 amino acid monomer moieties or no more than 2000 amino acid monomer moieties.

As used herein, the term "random coil" refers to a peptide or protein adopting/having/forming, preferably having, a conformation which substantially lacks a defined secondary and tertiary structure as determined by circular dichroism spectroscopy performed in aqueous buffer at ambient temperature, and pH 7.4. Preferably, ambient temperature is about 20° C., i.e. between 18° C. and 22° C., most preferably ambient temperature is 20° C.

As used herein, the term "oligonucleotide" refers to double- or single-stranded RNA and DNA with preferably 2 to 1000 nucleotides and any modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited, to 2'-position sugar modifications, 5-position pyrimidine modifications, 8-position purine modifications, modifications at exocyclic amines, substitution of 4-thiouridines, substitution of 5-bromo or 5-iodo-uracil; backbone modifications, methylations, unusual base-pairing combinations such as the isobases isocytidine and isoguanidine and the like. Modifications can also include 3' and 5' modifications such as capping and change of stereochemistry. The term also includes aptamers.

As used herein the term "small molecule biologically active moiety" refers to an organic biologically active moiety having a molecular weight of less than 1000 Da, such as less than 900 Da or less than 800 Da.

In general, the term "comprise" or "comprising" also encompasses "consist of" or "consisting of".

In the following paragraphs the invention is described in further detail.

Preferably, -D of formula (I) is preferably selected from the group consisting of small molecule biologically active moieties, oligonucleotide moieties, peptide nucleic acid moieties, peptide moieties and protein moieties. More preferably -D of formula (I) is selected from the group consisting of oligonucleotide moieties, peptide nucleic acid moieties, peptide moieties and protein moieties. Even more preferably -D of formula (I) is selected from the group consisting of peptide moieties and protein moieties.

In one preferred embodiment -D of formula (I) is a peptide moiety.

In a particular preferred embodiment -D of formula (I) is a CNP moiety.

In another preferred embodiment -D of formula (I) is a protein moiety.

Preferably, a of formula (I) is selected from the group consisting of 1, 2, 3 and 4 and most preferably a of formula (I) is 1.

Preferably, all moieties -$L^1$- of the reagent of formula (I) are the same.

The moiety -$L^1$- of formula (I) is a reversible prodrug linker from which the drug D-H is released in its free form, i.e. -$L^1$- of formula (I) is a traceless prodrug linker. Suitable prodrug linkers are known in the art, such as for example the reversible prodrug linker moieties disclosed in WO 2005/099768 A2, WO 2006/136586 A2, WO 2011/089216 A1 and WO 2013/024053 A1, which are incorporated by reference herewith.

In another embodiment -$L^1$- of formula (I) is a reversible prodrug linker as described in WO 2011/012722 A1, WO 2011/089214 A1, WO 2011/089215 A1, WO 2013/024052 A1 and WO 2013/160340 A1 which are incorporated by reference herewith.

The moiety -$L^1$- of formula (I) can be connected to -D of formula (I) through any type of linkage, provided that it is reversible. Preferably, -$L^1$- of formula (I) is connected to -D of formula (I) through a linkage selected from the group consisting of amide, ester, carbamate, acetal, aminal, imine, oxime, hydrazone, disulfide and acylguanidine. Even more preferably -$L^1$- of formula (I) is connected to -D of formula (I) through a linkage selected from the group consisting of amide, ester, carbamate and acylguanidine.

In a preferred embodiment, the moiety -$L^1$- of formula (I) is connected to -D of formula (I) through an amide linkage. It is understood that amide linkages, like some of the other linkages listed above, generally are not reversible, but that in the present invention neighboring groups comprised in -$L^1$- of formula (I) render them reversible.

A particularly preferred moiety -$L^1$- is disclosed in WO 2009/095479 A2. Accordingly, in one preferred embodiment the moiety -$L^1$- of formula (I) is of formula (a-i):

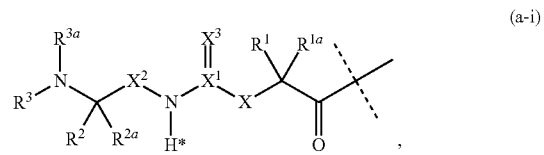

wherein
the dashed line indicates the attachment to a primary or secondary amine of -D by forming an amide bond;
—X— is —C($R^4R^{4a}$)—; —N($R^4$)—; —O—; —C($R^4R^{4a}$)—C($R^5R^{5a}$)—; —C($R^5R^{5a}$)—C($R^4R^{4a}$)—; —C($R^4R^{4a}$)—N($R^6$)—; —N($R^6$)—C($R^4R^{4a}$)—; —C($R^4R^{4a}$)—O—; —O—C($R^4R^{4a}$)—; or —C($R^7R^{7a}$)—;
>$X^1$═ is C; or S(O);
—$X^2$— is —C($R^8R^{8a}$)—; or —C($R^8R^{8a}$)—C($R^9R^{9a}$)—;
═$X^3$ is ═O; ═S; or ═N—CN;
—$R^1$, —$R^{1a}$, —$R^2$, —$R^{2a}$, —$R^4$, —$R^{4a}$, —$R^5$, —$R^{5a}$, —$R^6$, —$R^8$, —$R^{8a}$, —$R^9$, —$R^{9a}$ are independently selected from the group consisting of —H; and $C_{1-6}$ alkyl;
—$R^3$, —$R^{3a}$ are independently selected from the group consisting of —H; and $C_{1-6}$ alkyl, provided that in case one of —$R^3$, —$R^{3a}$ or both are other than —H they are connected to N to which they are attached through a $sp^3$-hybridized carbon atom;
—$R^7$ is —N($R^{10}R^{10a}$); or —N$R^{10}$—(C═O)—$R^{11}$;
—$R^{7a}$, —$R^{10}$, —$R^{10a}$, —$R^{11}$ are independently of each other —H; or $C_{1-6}$ alkyl;
optionally, one or more of the pairs —$R^{1a}$/—$R^{4a}$, —$R^{1a}$/—$R^{5a}$, —$R^{1a}$/—$R^{7a}$, —$R^{4a}$/—$R^{5a}$, —$R^{8a}$/—$R^{9a}$ form a chemical bond;
optionally, one or more of the pairs —$R^1$/—$R^{1a}$, —$R^2$/—$R^{2a}$, —$R^4$/—$R^{4a}$, —$R^5$/—$R^{5a}$, —$R^8$/—$R^{8a}$, —$R^9$/—$R^{9a}$ are joined together with the atom to which they are attached to form a $C_{3-10}$ cycloalkyl; or 3- to 10-membered heterocyclyl;
optionally, one or more of the pairs —$R^1$/—$R^4$, —$R^1$/—$R^5$, —$R^1$/—$R^6$, —$R^1$/—$R^{7a}$, —$R^4$/—$R^5$, —$R^4$/—$R^6$, —$R^8$/—$R^9$, —$R^2$/—$R^3$ are joined together with the atoms to which they are attached to form a ring $A^0$;
optionally, $R^3$/$R^{3a}$ are joined together with the nitrogen atom to which they are attached to form a 3- to 10-membered heterocycle;
$A^0$ is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and
wherein -$L^1$- is substituted with 1, 2, 3, 4, 5, 6, 7 or 8 moieties -$L^2$-A and
wherein -$L^1$- is optionally further substituted, provided that the hydrogen marked with the asterisk in formula (a-i) is not replaced by -$L^2$-A or a substituent.
Preferably, -$L^1$- of formula (a-i) is substituted with one moiety -$L^2$-A.

In one embodiment -$L^1$- of formula (a-i) is not further substituted.

It is understood that if —$R^3$/—$R^{3a}$ of formula (a-i) are joined together with the nitrogen atom to which they are attached to form a 3- to 10-membered heterocycle, only such 3- to 10-membered heterocycles may be formed in which the atoms directly attached to the nitrogen are sp³-hybridized carbon atoms. In other words, such 3- to 10-membered heterocycle formed by —R³/—R³ª together with the nitrogen atom to which they are attached has the following structure:

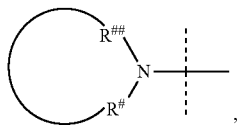

wherein
the dashed line indicates attachment to the rest of -L¹-;
the ring comprises 3 to 10 atoms comprising at least one nitrogen; and
R# and R## represent a sp³-hydridized carbon atom.

It is also understood that the 3- to 10-membered heterocycle may be further substituted.

Exemplary embodiments of suitable 3- to 10-membered heterocycles formed by —R³/—R³ª of formula (a-i) together with the nitrogen atom to which they are attached are the following:

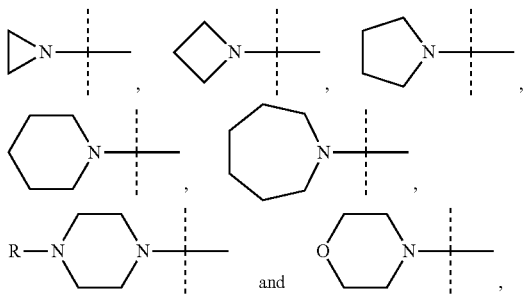

wherein
dashed lines indicate attachment to the rest of -L¹-; and
—R is selected from the group consisting of —H and $C_{1-6}$ alkyl.

-L¹- of formula (a-i) may optionally be further substituted. In general, any substituent may be used as far as the cleavage principle is not affected, i.e. the hydrogen marked with the asterisk in formula (a-i) is not replaced and the nitrogen of the moiety

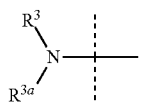

of formula (a-i) remains part of a primary, secondary or tertiary amine, i.e. —R³ and —R³ª are independently of each other —H or are connected to —N< through a sp³-hybridized carbon atom.

In one embodiment —R¹ or —R¹ª of formula (a-i) is substituted with -L²-A. In another embodiment —R² or —R²ª of formula (a-i) is substituted with -L²-A. In another embodiment —R³ or —R³ª of formula (a-i) is substituted with -L²-A. In another embodiment —R⁴ of formula (a-i) is substituted with -L²-A. In another embodiment —R⁵ or —R⁵ª of formula (a-i) is substituted with -L²-A. In another embodiment —R⁶ of formula (a-i) is substituted with -L²-A. In another embodiment —R⁷ or —R⁷ª of formula (a-i) is substituted with -L²-A. In another embodiment —R⁸ or —R⁸ª of formula (a-i) is substituted with -L²-A. In another embodiment —R⁹ or —R⁹ª of formula (a-i) is substituted with -L²-A. Preferably, -A is —Y⁰.

Most preferably, —R⁴ of formula (a-i) is substituted with -L²-A and -A is —Y⁰.

Preferably, —X— of formula (a-i) is —C(R⁴R⁴ª)— or —N(R⁴)—. Most preferably, —X— of formula (a-i) is —C(R⁴R⁴ª)—.

Preferably, >X¹= of formula (a-i) is C.
Preferably, =X³ of formula (a-i) is =O.
Preferably, —X²— of formula (a-i) is —C(R⁸R⁸ª)—.
Preferably —R⁸ and —R⁸ª of formula (a-i) are independently selected from the group consisting of —H, methyl and ethyl. More preferably at least one of —R⁸ and —R⁸ª of formula (a-i) is —H. Even more preferably both —R⁸ and —R⁸ª of formula (a-i) are —H.

Preferably, —R¹ and —R¹ª of formula (a-i) are independently selected from the group consisting of —H, methyl and ethyl. More preferably, at least one of —R¹ and —R¹ª of formula (a-i) is —H. Even more preferably both —R¹ and —R¹ª of formula (a-i) are —H.

Preferably, —R² and —R²ª of formula (a-i) are independently selected from the group consisting of —H, methyl and ethyl. More preferably, at least one of —R² and —R²ª of formula (a-i) is —H. Even more preferably both —R² and —R²ª of formula (a-i) are H.

Preferably, —R³ and —R³ª of formula (a-i) are independently selected from the group consisting of —H, methyl, ethyl, propyl and butyl. Even more preferably at least one of —R³ and —R³ª of formula (a-i) is methyl. In an equally preferred embodiment —R³ and —R³ª of formula (a-i) are both —H. In another equally preferred embodiment —R³ and —R³ª of formula (a-i) are both methyl.

Preferably, —R³ of formula (a-i) is —H and —R³ª of formula (a-i) is methyl.

Preferably, —R⁴ and —R⁴ª of formula (a-i) are independently selected from the group consisting of —H, methyl and ethyl. More preferably, at least one of —R⁴ and —R⁴ª of formula (a-i) is —H. Even more preferably both —R⁴ and —R⁴ª of formula (a-i) are —H.

Preferably the moiety -L¹- of formula (I) is of formula (a-ii):

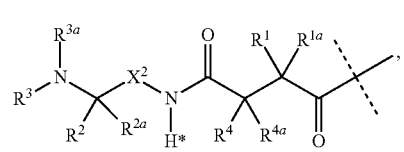

wherein
the dashed line indicates the attachment to a primary or secondary amine of -D by forming an amide bond;
—R¹, —R¹ª, —R², —R²ª, —R³, —R³ª, —R⁴, —R⁴ª and —X²— are used as defined in formula (a-i); and
wherein -L¹- is substituted with 1, 2, 3, 4, 5, 6, 7 or 8 moieties -L²-A and
wherein -L¹- is optionally further substituted, provided that the hydrogen marked with the asterisk in formula (a-ii) is not replaced by -L²-A or a substituent.

Preferably, -L¹- of formula (a-ii) is substituted with one moiety -L²-A.

Preferably, the moiety -L$^1$- of formula (a-ii) is not further substituted.

Preferably, —R$^1$ and —R$^{1a}$ of formula (a-ii) are independently selected from the group consisting of —H, methyl and ethyl. More preferably, at least one of —R$^1$ and —R$^{1a}$ of formula (a-ii) is —H. Even more preferably both —R$^1$ and —R$^{1a}$ of formula (a-ii) are —H.

Preferably, —R$^4$ and —R$^{4a}$ of formula (a-ii) are independently selected from the group consisting of —H, methyl and ethyl. More preferably, at least one of —R$^4$ and —R$^{4a}$ of formula (a-ii) is —H. Even more preferably both —R$^4$ and —R$^{4a}$ of formula (a-ii) are —H.

Preferably, —X$^2$— of formula (a-ii) is —C(R$^8$R$^{8a}$)—.

Preferably —R$^8$ and —R$^{8a}$ of formula (a-ii) are independently selected from the group consisting of —H, methyl and ethyl. More preferably at least one of —R$^8$ and —R$^{8a}$ of formula (a-ii) is —H. Even more preferably both —R$^8$ and —R$^{8a}$ of formula (a-ii) are —H.

Preferably, —R$^2$ and —R$^{2a}$ of formula (a-ii) are independently selected from the group consisting of —H, methyl and ethyl. More preferably, at least one of —R$^2$ and —R$^{2a}$ of formula (a-ii) is —H. Even more preferably both —R$^2$ and —R$^{2a}$ of formula (a-ii) are H.

Preferably, —R$^3$ and —R$^{3a}$ of formula (a-ii) are independently selected from the group consisting of —H, methyl, ethyl, propyl and butyl. Even more preferably at least one of —R$^3$ and —R$^{3a}$ of formula (a-ii) is methyl. In an equally preferred embodiment —R$^3$ and —R$^{3a}$ of formula (a-ii) are both —H. In another equally preferred embodiment —R$^3$ and —R$^{3a}$ of formula (a-ii) are both methyl.

Preferably, —R$^3$ of formula (a-ii) is —H and —R$^{3a}$ of formula (a-ii) is methyl.

Preferably the moiety -L$^1$- of formula (I) is of formula (a-iii):

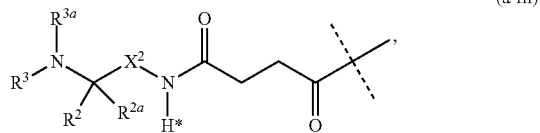

(a-iii)

wherein the dashed line indicates the attachment to a primary or secondary amine of -D by forming an amide bond;

—R$^2$, —R$^{2a}$, —R$^3$, —R$^{3a}$ and —X$^2$— are used as defined in formula (a-i); and wherein -L$^1$- is substituted with 1, 2, 3, 4, 5, 6, 7 or 8 moieties -L$^2$-A and wherein -L$^1$- is optionally further substituted, provided that the hydrogen marked with the asterisk in formula (a-iii) is not replaced by -L$^2$-A or a substituent.

Preferably -L$^1$- of formula (a-iii) is substituted with one moiety -L$^2$-A.

Preferably the moiety -L$^1$- of formula (a-iii) is not further substituted.

Preferably, —X$^2$— of formula (a-iii) is —C(R$^8$R$^{8a}$)—.

Preferably —R$^8$ and —R$^{8a}$ of formula (a-iii) are independently selected from the group consisting of —H, methyl and ethyl. More preferably at least one of —R$^8$ and —R$^{8a}$ of formula (a-iii) is —H. Even more preferably both —R$^8$ and —R$^{8a}$ of formula (a-iii) are —H.

Preferably, —R$^2$ and —R$^{2a}$ of formula (a-iii) are independently selected from the group consisting of —H, methyl and ethyl. More preferably, at least one of —R$^2$ and —R$^{2a}$ of formula (a-iii) is —H. Even more preferably both —R$^2$ and —R$^{2a}$ of formula (a-iii) are H.

Preferably, —R$^3$ and —R$^{3a}$ of formula (a-iii) are independently selected from the group consisting of —H, methyl, ethyl, propyl and butyl. Even more preferably at least one of —R$^3$ and —R$^{3a}$ of formula (a-iii) is methyl. In an equally preferred embodiment —R$^3$ and —R$^{3a}$ of formula (a-iii) are both —H. In another equally preferred embodiment —R$^3$ and —R$^{3a}$ of formula (a-iii) are both methyl.

Most preferably, —R$^3$ of formula (a-iii) is —H and —R$^{3a}$ of formula (a-iii) is methyl.

Even more preferably the moiety -L$^1$- of formula (I) is of formula (a-iii'):

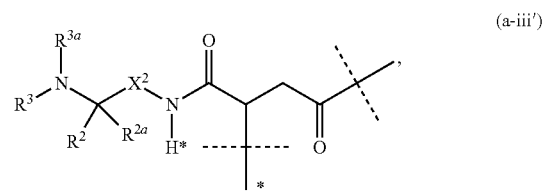

(a-iii')

wherein the dashed line indicates the attachment to a primary or secondary amine of -D by forming an amide bond;

the dashed line marked with the asterisk indicates attachment to -L$^2$-;

—R$^2$, —R$^{2a}$, —R$^3$, —R$^{3a}$ and —X$^2$— are used as defined in formula (a-i); and wherein -L$^1$- is substituted with 1, 2, 3, 4, 5, 6, 7 or 8 moieties -L$^2$-A and wherein -L$^1$- is optionally further substituted, provided that the hydrogen marked with the asterisk in formula (a-iii') is not replaced by -L$^2$-A or a substituent.

Preferably -L$^1$- of formula (a-iii') is substituted with one moiety -L$^2$-A.

Preferably the moiety -L$^1$- of formula (a-iii') is not further substituted.

Preferably, —X$^2$— of formula (a-iii') is —C(R$^8$R$^{8a}$)—.

Preferably —R$^8$ and —R$^{8a}$ of formula (a-iii') are independently selected from the group consisting of —H, methyl and ethyl. More preferably at least one of —R$^8$ and —R$^{8a}$ of formula (a-iii') is —H. Even more preferably both —R$^8$ and —R$^{8a}$ of formula (a-iii') are —H.

Preferably, —R$^2$ and —R$^{2a}$ of formula (a-iii') are independently selected from the group consisting of —H, methyl and ethyl. More preferably, at least one of —R$^2$ and —R$^{2a}$ of formula (a-iii') is —H. Even more preferably both —R$^2$ and —R$^{2a}$ of formula (a-iii') are H.

Preferably, —R$^3$ and —R$^{3a}$ of formula (a-iii') are independently selected from the group consisting of —H, methyl, ethyl, propyl and butyl. Even more preferably at least one of —R$^3$ and —R$^{3a}$ of formula (a-iii') is methyl. In an equally preferred embodiment —R$^3$ and —R$^{3a}$ of formula (a-iii') are both —H. In another equally preferred embodiment —R$^3$ and —R$^{3a}$ of formula (a-iii') are both methyl.

Most preferably, —R$^3$ of formula (a-iii') is —H and —R$^{3a}$ of formula (a-iii') is methyl.

Preferably the moiety -$L^1$- of formula (I) is of formula (a-iv):

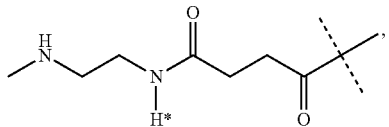
(a-iv)

wherein
the dashed line indicates the attachment to a primary or secondary amine of -D by forming an amide bond; and
wherein -$L^1$- is substituted with 1, 2, 3, 4, 5, 6, 7 or 8 moieties -$L^2$-A and
wherein -$L^1$- is optionally further substituted, provided that the hydrogen marked with the asterisk in formula (a-iv) is not replaced by -$L^2$-A or a substituent.

Preferably -$L^1$- of formula (a-iv) is substituted with one moiety -$L^2$-A.

Preferably the moiety -$L^1$- of formula (a-iv) is not further substituted.

In another preferred embodiment the moiety -$L^1$- of formula (I) is of formula (a-v):

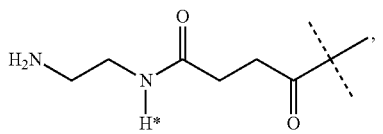
(a-v)

wherein
the dashed line indicates the attachment to a primary or secondary amine of -D by forming an amide bond; and
wherein -$L^1$- is substituted with 1, 2, 3, 4, 5, 6, 7 or 8 moieties -$L^2$-A and
wherein -$L^1$- is optionally further substituted, provided that the hydrogen marked with the asterisk in formula (a-v) is not replaced by -$L^2$-A or a substituent.

Preferably -$L^1$- of formula (a-v) is substituted with one moiety -$L^2$-A.

Preferably the moiety -$L^1$- of formula (a-v) is not further substituted.

In another preferred embodiment the moiety -$L^1$- of formula (I) is of formula (a-vi):

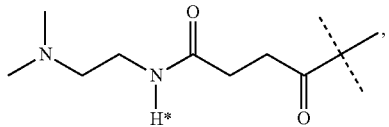
(a-vi)

wherein
the dashed line indicates the attachment to a primary or secondary amine of -D by forming an amide bond; and
wherein -$L^1$- is substituted with 1, 2, 3, 4, 5, 6, 7 or 8 moieties -$L^2$-A and
wherein -$L^1$- is optionally further substituted, provided that the hydrogen marked with the asterisk in formula (a-vi) is not replaced by -$L^2$-A or a substituent.

Preferably -$L^1$- of formula (a-vi) is substituted with one moiety -$L^2$-A.

Preferably the moiety -$L^1$- of formula (a-vi) is not further substituted.

Even more preferably the moiety -$L^1$- of formula (I) is selected from the group consisting of formula (a-vii), (a-viii), (a-ix), (a-x) and (a-xi):

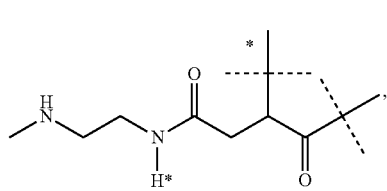
(a-vii)

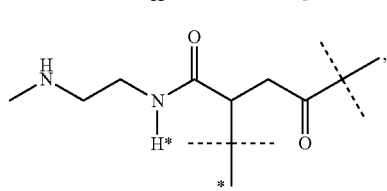
(a-viii)

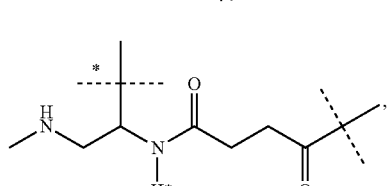
(a-ix)

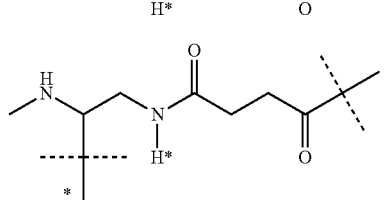
(a-x)

and
wherein
the unmarked dashed line indicates the attachment to a primary or secondary amine of -D by forming an amide bond;
the dashed line marked with the asterisk indicates attachment to -$L^2$-A; and
wherein -$L^1$- is optionally further substituted, provided that the hydrogen marked with the asterisk in formula (a-vii), (a-viii), (a-ix), (a-x) and (a-xi) is not replaced by a substituent.

Preferably, the moiety -$L^1$- of formula (a-vii), (a-viii), (a-ix), (a-x) and (a-xi) is not further substituted.

In a particularly preferred embodiment the moiety -$L^1$- of formula (I) is:

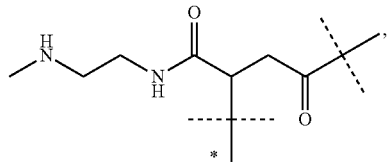
(a-viii)

wherein
the unmarked dashed line indicates the attachment to a primary or secondary amine of -D by forming an amide bond; and the dashed line marked with the asterisk indicates attachment to -L²-A;

In an equally preferred embodiment the moiety -L¹- of formula (I) is selected from the group consisting of formula (a-vii-a), (a-viii-a), (a-ix-a), (a-x-a) and (a-xi-a):

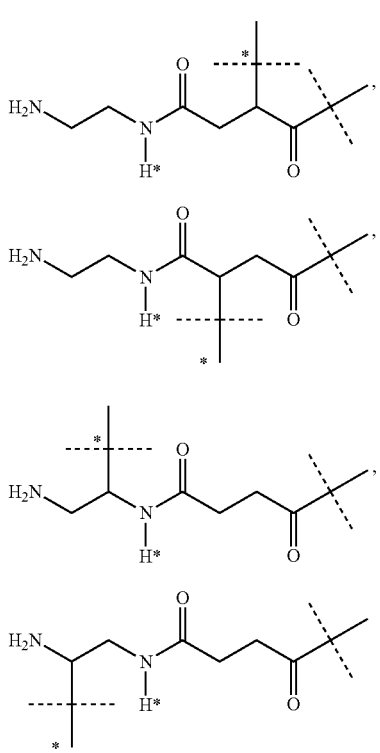

and
wherein
the unmarked dashed line indicates the attachment to a primary or secondary amine of -D by forming an amide bond;
the dashed line marked with the asterisk indicates attachment to -L²-A; and
wherein -L¹- is optionally further substituted, provided that the hydrogen marked with the asterisk in formula (a-vii-a), (a-viii-a), (a-ix-a), (a-x-a) and (a-xi-a) is not replaced by a substituent.

Preferably, the moiety -L¹- of formula (a-vii-a), (a-viii-a), (a-ix-a), (a-x-a) and (a-xi-a) is not further substituted.

In another particularly preferred embodiment the moiety -L¹- of formula (I) is:

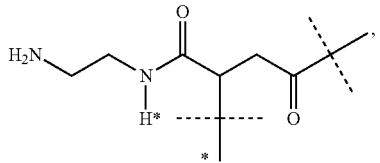

wherein
the unmarked dashed line indicates the attachment to a primary or secondary amine of -D by forming an amide bond; and the dashed line marked with the asterisk indicates attachment to -L²-A;

In an equally preferred embodiment the moiety -L¹- of formula (I) is selected from the group consisting of formula (a-vii-b), (a-viii-b), (a-ix-b) and (a-x-b):

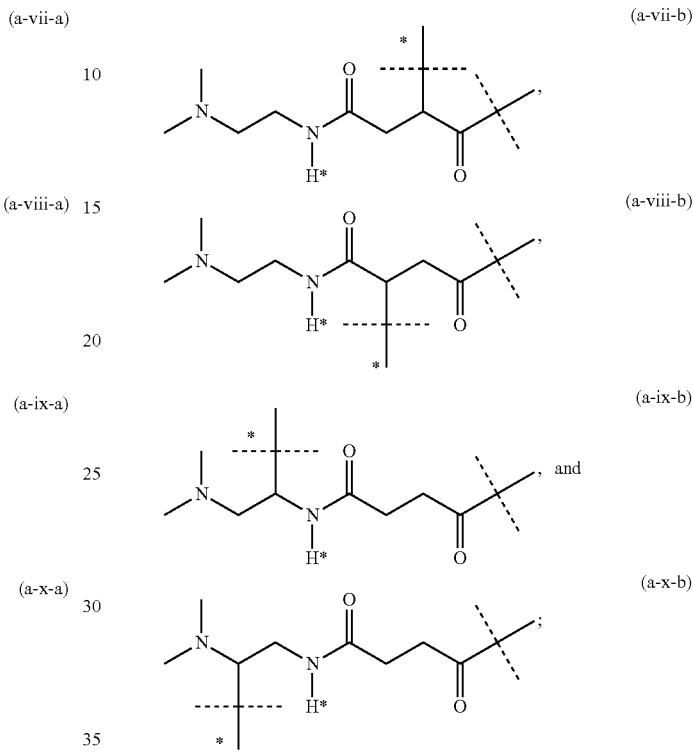

wherein
the unmarked dashed line indicates the attachment to a primary or secondary amine of -D by forming an amide bond;
the dashed line marked with the asterisk indicates attachment to -L²-A; and
wherein -L¹- is optionally further substituted, provided that the hydrogen marked with the asterisk in formula (a-vii-b), (a-viii-b), (a-ix-b) and (a-x-b) is not replaced by a substituent.

Preferably, the moiety -L¹- of formula (a-vii-b), (a-viii-b), (a-ix-b) and (a-x-b) is not further substituted.

In another particularly preferred embodiment the moiety -L¹- of formula (I) is

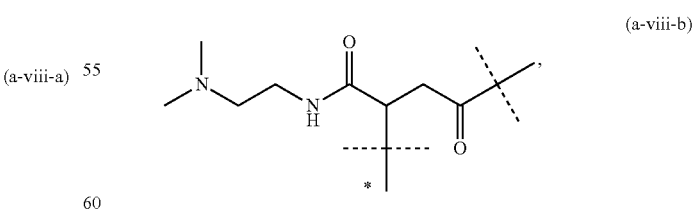

wherein
the unmarked dashed line indicates the attachment to a primary or secondary amine of -D by forming an amide bond; and
the dashed line marked with the asterisk indicates attachment to -L²-A;

The optional further substituents of -L$^1$- of formula (a-i), (a-ii), (a-iii), (a-iii'), (a-iv), (a-v), (a-vi), (a-vii), (a-viii), (a-ix), (a-x), (a-xi), (a-vii-a), (a-viii-a), (a-ix-a), (a-x-a), (a-xi-a), (a-vii-b), (a-viii-b), (a-ix-b) and (a-x-b) are preferably as described above.

Another particularly preferred moiety -L$^1$- of formula (I) is disclosed in WO 2016/020373 A1. Accordingly, in another preferred embodiment the moiety -L$^1$- of formula (I) is of formula (b):

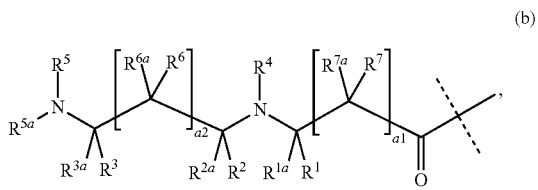

(b)

wherein
the dashed line indicates attachment to a primary or secondary amine or hydroxyl of -D by forming an amide or ester linkage, respectively;

—R$^1$, —R$^{1a}$, —R$^2$, —R$^{2a}$, —R$^3$ and —R$^{3a}$ are independently of each other selected from the group consisting of —H, —C(R$^8$R$^{8a}$R$^{8b}$), —C(=O)R$^8$, —C≡N, —C(=NR$^8$)R$^{8a}$, —CR$^8$(=CR$^{8a}$R$^{8b}$), —C≡CR$^8$ and -T;

—R$^4$, —R$^5$ and —R$^{5a}$ are independently of each other selected from the group consisting of —H, —C(R$^9$R$^{9a}$R$^{9b}$) and -T;

a1 and a2 are independently of each other 0 or 1;

each —R$^6$, —$^{6a}$, —R$^7$, —R$^{7a}$, —R$^8$, —R$^{8a}$, —R$^{8b}$, —R$^9$, —R$^{9a}$, —R$^{9b}$ are independently of each other selected from the group consisting of —H, halogen, —CN, —COOR$^{10}$, —OR$^{10}$, —C(O)R$^{10}$, —C(O)N(R$^{10}$R$^{10a}$), —S(O)$_2$N(R$^{10}$R$^{10a}$), —S(O)N(R$^{10}$R$^{10a}$), —S(O)$_2$R$^{10}$, —S(O)R$^{10}$, —N(R$^{10}$)S(O)$_2$N(R$^{10a}$R$^{10b}$), —SR$^{10}$, —N(R$^{10}$R$^{10a}$), —NO$_2$, —OC(O)R$^{10}$, —N(R$^{10}$)C(O)R$^{10a}$, —N(R$^{10}$)S(O)$_2$R$^{10a}$, —N(R$^{10}$)S(O)R$^{10a}$, —N(R$^{10}$)C(O)OR$^{10a}$, —N(R$^{10}$)C(O)N(R$^{10a}$R$^{10b}$), —OC(O)N(R$^{10}$R$^{10a}$), -T, C$_{1-20}$ alkyl, C$_{2-20}$ alkenyl, and C$_{2-20}$ alkynyl; wherein -T, C$_{1-20}$ alkyl, C$_{2-20}$ alkenyl, and C$_{2-20}$ alkynyl are optionally substituted with one or more —R$^{11}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{12}$)—, —S(O)$_2$N(R$^{12}$)—, —S(O)N(R$^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$)—, and —OC(O)N(R$^{12}$)—;

each —R$^{10}$, —R$^{10a}$, —R$^{10b}$ is independently selected from the group consisting of —H, -T, C$_{1-20}$ alkyl, C$_{2-20}$ alkenyl, and C$_{2-20}$ alkynyl; wherein -T, C$_{1-20}$ alkyl, C$_{2-20}$ alkenyl, and C$_{2-20}$ alkynyl are optionally substituted with one or more —R$^{11}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{12}$)—, —S(O)$_2$N(R$^{12}$)—, —S(O)N(R$^{12}$)—, —S(O)$_2$—, —S(O)—, —N(R$^{12}$)S(O)$_2$N(R$^{12a}$)—, —S—, —N(R$^{12}$)—, —OC(OR$^{12}$)(R$^{12a}$)—, —N(R$^{12}$)C(O)N(R$^{12a}$)—, and —OC(O)N(R$^{12}$)—;

each T is independently of each other selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T is independently optionally substituted with one or more —R$^{11}$, which are the same or different;

each —R$^{11}$ is independently of each other selected from halogen, —CN, oxo (=O), —COOR$^{13}$, —OR$^{13}$, —C(O)R$^{13}$, —C(O)N(R$^{13}$R$^{13a}$), —S(O)$_2$N(R$^{13}$R$^{13a}$), —S(O)N(R$^{13}$R$^{13a}$), —S(O)$_2$R$^{13}$, —S(O)R$^{13}$, —N(R$^{13}$)S(O)$_2$N(R$^{13a}$R$^{13b}$), —SR$^{13}$, —N(R$^{13}$R$^{13a}$), —NO$_2$, —OC(O)R$^{13}$, —N(R$^{13}$)C(O)R$^{13a}$, —N(R$^{13}$)S(O)$_2$R$^{13a}$, —N(R$^{13}$)S(O)R$^{13a}$, —N(R$^{13}$)C(O)OR$^{13a}$, —N(R$^{13}$)C(O)N(R$^{13a}$R$^{13b}$), —OC(O)N(R$^{13}$R$^{13a}$), and C$_{1-6}$ alkyl; wherein C$_{1-6}$ alkyl is optionally substituted with one or more halogen, which are the same or different;

each —R$^{12}$, —R$^{12a}$, —R$^{13}$, —R$^{13a}$, —R$^{13b}$ is independently selected from the group consisting of —H, and C$_{1-6}$ alkyl; wherein C$_{1-6}$ alkyl is optionally substituted with one or more halogen, which are the same or different;

optionally, one or more of the pairs —R$^1$/—R$^{1a}$, —R$^2$/—R$^{2a}$, —R$^3$/—R$^{3a}$, —R$^6$/—R$^{6a}$, —R$^7$/—R$^{7a}$ are joined together with the atom to which they are attached to form a C$_{3-10}$ cycloalkyl or a 3- to 10-membered heterocyclyl;

optionally, one or more of the pairs —R$^1$/—R$^2$, —R$^1$/—R$^3$, —R$^1$/—R$^4$, —R$^1$/—R$^5$, —R$^1$/—R$^6$, —R$^1$/—R$^7$, —R$^2$/—R$^3$, —R$^2$/—R$^4$, —R$^2$/—R$^5$, —R$^2$/—R$^6$, —R$^2$/—R$^7$, —R$^3$/—R$^4$, —R$^3$/—R$^5$, —R$^3$/—R$^6$, —R$^3$/—R$^7$, —R$^4$/—R$^5$, —R$^4$/—R$^6$, —R$^4$/—R$^7$, —R$^5$/—R$^6$, —R$^5$/—R$^7$, —R$^6$/—R$^7$ are joint together with the atoms to which they are attached to form a ring A$^o$;

A$^o$ is selected from the group consisting of phenyl; naphthyl; indenyl; indanyl; tetralinyl; C$_{3-10}$ cycloalkyl; 3- to 10-membered heterocyclyl; and 8- to 11-membered heterobicyclyl;

wherein -L$^1$- is substituted with 1, 2, 3, 4, 5, 6, 7 or 8 moieties -L$^2$-A and wherein -L$^1$- is optionally further substituted.

The optional further substituents of -L$^1$- of formula (b) are preferably as described above.

Preferably -L$^1$- of formula (b) is substituted with one moiety -L$^2$-A.

Preferably -L$^1$- of formula (b) is not further substituted.

Additional preferred embodiments for -L$^1$- of formula (I) are disclosed in WO 2009/009712 A1, WO 2008/034122 A1, WO 2009/143412 A2, WO 2011/082368 A2, and U.S. Pat. No. 8,618,124 B2, which are herewith incorporated by reference in their entirety.

Additional preferred embodiments for -L$^1$- of formula (I) are disclosed in U.S. Pat. No. 8,946,405 B2 and U.S. Pat. No. 8,754,190 B2, which are herewith incorporated by reference in their entirety. Accordingly, a preferred moiety -L$^1$- is of formula (c):

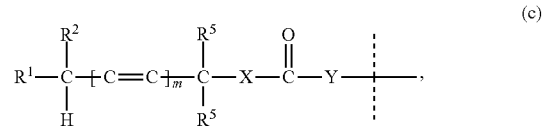

(c)

wherein the dashed line indicates attachment to -D through a functional group of -D selected from the group consisting of —OH, —SH and —NH$_2$;

m is 0 or 1;

at least one or both of —R$^1$ and —R$^2$ is/are independently of each other selected from the group consisting of —CN, —NO$_2$, optionally substituted aryl, optionally substituted heteroaryl, optionally substituted alkenyl, optionally substituted alkynyl, —C(O)R$^3$, —S(O)R$^3$, —S(O)$_2$R$^3$, and —SR$^4$;

one and only one of —R$^1$ and —R$^2$ is selected from the group consisting of —H, optionally substituted alkyl, optionally substituted arylalkyl, and optionally substituted heteroarylalkyl;

—R$^3$ is selected from the group consisting of —H, optionally substituted alkyl, optionally substituted aryl, optionally substituted arylalkyl, optionally substituted heteroaryl, optionally substituted heteroarylalkyl, —OR$^9$ and —N(R$^9$)$_2$;

—R$^4$ is selected from the group consisting of optionally substituted alkyl, optionally substituted aryl, optionally substituted arylalkyl, optionally substituted heteroaryl, and optionally substituted heteroarylalkyl;

each —R$^5$ is independently selected from the group consisting of —H, optionally substituted alkyl, optionally substituted alkenylalkyl, optionally substituted alkynylalkyl, optionally substituted aryl, optionally substituted arylalkyl, optionally substituted heteroaryl and optionally substituted heteroarylalkyl;

—R$^9$ is selected from the group consisting of —H and optionally substituted alkyl;

—Y— is absent and —X— is —O— or —S—; or

—Y— is —N(Q)CH$_2$— and —X— is —O—;

Q is selected from the group consisting of optionally substituted alkyl, optionally substituted aryl, optionally substituted arylalkyl, optionally substituted heteroaryl and optionally substituted heteroarylalkyl;

optionally, —R$^1$ and —R$^2$ may be joined to form a 3 to 8-membered ring; and optionally, both —R$^9$ together with the nitrogen to which they are attached form a heterocyclic ring;

wherein -L$^1$- is substituted with 1, 2, 3, 4, 5, 6, 7 or 8 moieties -L$^2$-A and wherein -L$^1$- is optionally further substituted.

The optional further substituents of -L$^1$- of formula (c) are preferably as described above.

Preferably -L$^1$- of formula (c) is substituted with one moiety -L$^2$-A.

Preferably -L$^1$- of formula (c) is not further substituted.

Only in the context of formula (c) the terms used have the following meaning:

The term "alkyl" as used herein includes linear, branched or cyclic saturated hydrocarbon groups of 1 to 8 carbons, or in some embodiments 1 to 6 or 1 to 4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds.

The term "alkynyl" includes non-aromatic unsaturated hydrocarbons with carbon-carbon triple bonds.

The term "aryl" includes aromatic hydrocarbon groups of 6 to 18 carbons, preferably 6 to 10 carbons, including groups such as phenyl, naphthyl, and anthracenyl. The term "heteroaryl" includes aromatic rings comprising 3 to 15 carbons containing at least one N, O or S atom, preferably 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instance, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4 to 8 membered aromatic or non-aromatic ring comprising 3 to 7 carbon atoms and at least one N, O, or S atom. Examples are piperidinyl, piperazinyl, tetrahydropyranyl, pyrrolidine, and tetrahydrofuranyl, as well as the exemplary groups provided for the term "heteroaryl" above.

When a ring system is optionally substituted, suitable substituents are selected from the group consisting of alkyl, alkenyl, alkynyl, or an additional ring, each optionally further substituted. Optional substituents on any group, including the above, include halo, nitro, cyano, —OR, —SR, —NR$_2$, —OCOR, —NRCOR, —COOR, —CONR$_2$, —SOR, —SO$_2$R, —SONR$_2$, —SO$_2$NR$_2$, wherein each R is independently alkyl, alkenyl, alkynyl, aryl or heteroaryl, or two R groups taken together with the atoms to which they are attached form a ring.

An additional preferred embodiment for -L$^1$- of formula (I) is disclosed in WO 2013/036857 A1, which is herewith incorporated by reference in its entirety. Accordingly, a preferred moiety -L$^1$- is of formula (d):

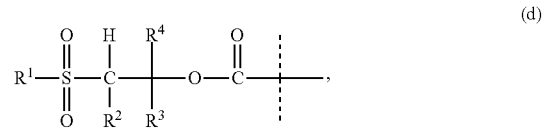

wherein the dashed line indicates attachment to -D through an amine functional group of -D;

—R$^1$ is selected from the group consisting of optionally substituted C$_1$-C$_6$ linear, branched, or cyclic alkyl; optionally substituted aryl; optionally substituted heteroaryl; alkoxy; and —NR$^5$$_2$;

—R$^2$ is selected from the group consisting of —H; optionally substituted C$_1$-C$_6$ alkyl; optionally substituted aryl; and optionally substituted heteroaryl;

—R$^3$ is selected from the group consisting of —H; optionally substituted C$_1$-C$_6$ alkyl; optionally substituted aryl; and optionally substituted heteroaryl;

—R$^4$ is selected from the group consisting of —H; optionally substituted C$_1$-C$_6$ alkyl; optionally substituted aryl; and optionally substituted heteroaryl;

each —R$^5$ is independently of each other selected from the group consisting of —H; optionally substituted C$_1$-C$_6$ alkyl; optionally substituted aryl; and optionally substituted heteroaryl; or when taken together two —R$^5$ can be cycloalkyl or cycloheteroalkyl;

wherein -L$^1$- is substituted with 1, 2, 3, 4, 5, 6, 7 or 8 moieties -L$^2$-A and wherein -L$^1$- is optionally further substituted.

The optional further substituents of -L$^1$- of formula (d) are preferably as described above.

Preferably -L$^1$- of formula (d) is substituted with one moiety -L$^2$-A.

Preferably -L$^1$- of formula (d) is not further substituted.

Only in the context of formula (d) the terms used have the following meaning:

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6 carbons.

"Aryl" includes aromatic hydrocarbon groups of 6-18 carbons, preferably 6-10 carbons, including groups such as phenyl, naphthyl, and anthracene. "Heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiszolyl, isothiazolyl, quinolyl, indolyl, indenyl, and similar.

The term "substituted" means an alkyl, alkenyl, alkynyl, aryl, or heteroaryl group comprising one or more substituent groups in place of one or more hydrogen atoms. Substituents may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched and cyclic; amino, alkylamino, dialkylamino, silyl including alkylsilyl, alkoxysilyl, and arylsilyl; nitro; cyano; carbonyl; carboxylic acid, carboxylic ester, carboxylic amide, aminocarbonyl; aminoacyl; carbamate; urea; thiocarbamate; thiourea; ketone; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

A further preferred embodiment for -L$^1$- of formula (I) is disclosed in U.S. Pat. No. 7,585,837 B2, which is herewith incorporated by reference in its entirety. Accordingly, a preferred moiety -L$^1$- is of formula (e):

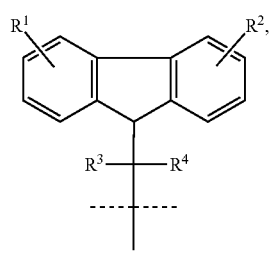

wherein
the dashed line indicates attachment to -D through an amine functional group of -D;

—R$^1$ and —R$^2$ are independently selected from the group consisting of hydrogen, alkyl, alkoxy, alkoxyalkyl, aryl, alkaryl, aralkyl, halogen, nitro, —SO$_3$H, —SO$_2$NHR$^5$, amino, ammonium, carboxyl, PO$_3$H$_2$, and OPO$_3$H$_2$;

—R$^3$, —R$^4$, and —R$^5$ are independently selected from the group consisting of hydrogen, alkyl, and aryl;

wherein -L$^1$- is substituted with 1, 2, 3, 4, 5, 6, 7 or 8 moieties -L$^2$-A and wherein -L$^1$- is optionally further substituted.

Suitable substituents for formulas (e) are alkyl (such as C$_{1-6}$ alkyl), alkenyl (such as C$_{2-6}$ alkenyl), alkynyl (such as C$_{2-6}$ alkynyl), aryl (such as phenyl), heteroalkyl, heteroalkenyl, heteroalkynyl, heteroaryl (such as aromatic 4 to 7 membered heterocycle) or halogen moieties.

Preferably -L$^1$- of formula (e) is substituted with one moiety -L$^2$-A.

Preferably -L$^1$- of formula (e) is not further substituted.

Only in the context of formula (e) the terms used have the following meaning:

The terms "alkyl", "alkoxy", "alkoxyalkyl", "aryl", "alkaryl" and "aralkyl" mean alkyl radicals of 1-8, preferably 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

A further preferred embodiment for -L$^1$- of formula (I) is disclosed in WO 2002/089789 A1, which is herewith incorporated by reference in its entirety. Accordingly, a preferred moiety -L$^1$- is of formula (f):

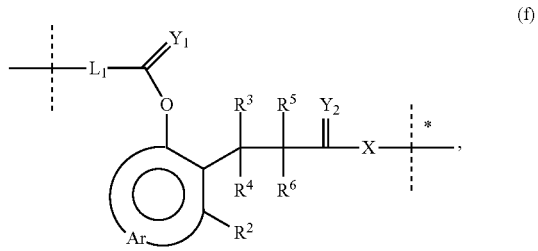

wherein
the dashed line indicates attachment to -D through an amine functional group of -D;
L$_1$ is a bifunctional linking group,
Y$_1$ and Y$_2$ are independently O, S or NR$^7$;
R$^2$, R$^3$, R$^4$, R$^5$, R$^6$ and R$^7$ are independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cycloalkyls, aryls, substituted aryls, aralkyls, C$_{1-6}$ heteroalkyls, substituted C$_{1-6}$ heteroalkyls, C$_{1-6}$ alkoxy, phenoxy, and C$_{1-6}$ heteroalkoxy;
Ar is a moiety which when included in formula (VII) forms a multisubstituted aromatic hydrocarbon or a multi-substituted heterocyclic group;
X is a chemical bond or a moiety that is actively transported into a target cell, a hydrophobic moiety, or a combination thereof,
y is 0 or 1;
wherein -L$^1$- is substituted with 1, 2, 3, 4, 5, 6, 7 or 8 moieties -L$^2$-A and
wherein -L$^1$- is optionally further substituted.

The optional further substituents of -L$^1$- of formula (f) are preferably as described above.

Preferably -L¹- of formula (f) is substituted with one moiety -L²-A.

Preferably -L¹- of formula (f) is not further substituted.

Only in the context of formula (f) the terms used have the following meaning:

The term "alkyl" shall be understood to include, e.g. straight, branched, substituted $C_{1-12}$ alkyls, including alkoxy, $C_{3-8}$ cycloalkyls or substituted cycloalkyls, etc.

The term "substituted" shall be understood to include adding or replacing one or more atoms contained within a functional group or compounds with one or more different atoms.

Substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxythiophone; alkoxy includes moieties such as methoxy; and phenoxy includes moieties such as 3-nitrophenoxy. Halo-shall be understood to include fluoro, chloro, iodo and bromo.

In another preferred embodiment -L¹- of formula (I) comprises a substructure of formula (g):

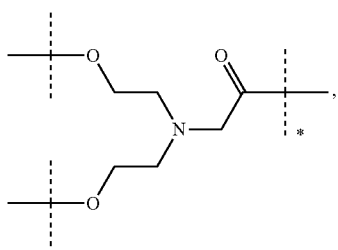

(g)

wherein the dashed line marked with the asterisk indicates attachment to a nitrogen of -D by forming an amide bond;

the unmarked dashed lines indicate attachment to the remainder of -L¹-; and wherein -L¹- is substituted with 1, 2, 3, 4, 5, 6, 7 or 8 moieties -L²-A and wherein -L¹- is optionally further substituted.

The optional further substituents of -L¹- of formula (g) are preferably as described above.

Preferably -L¹- of formula (g) is substituted with one moiety -L²-A.

Preferably -L¹- of formula (g) is not further substituted.

In another preferred embodiment -L¹- of formula (I) comprises a substructure of formula (h):

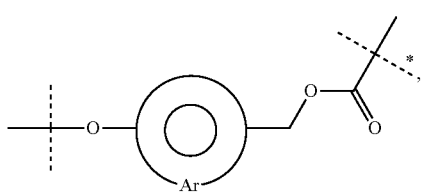

(h)

wherein the dashed line marked with the asterisk indicates attachment to a nitrogen of -D by forming a carbamate bond;

the unmarked dashed lines indicate attachment to the remainder of -L¹-; and wherein -L¹- is substituted with 1, 2, 3, 4, 5, 6, 7 or 8 moieties -L²-A and wherein -L¹- is optionally further substituted.

The optional further substituents of -L¹- of formula (h) are preferably as described above.

Preferably -L¹- of formula (h) is substituted with one moiety -L²-A.

Preferably -L¹- of formula (h) is not further substituted.

If —Z of formula (II) is a water-soluble carrier, b of formula (II) is selected from the group consisting of 1, 2, 3, 4, 5, 6, 7, 8, 9, 10, 11 and 12. If —Z of formula (II) is a water-soluble carrier, b of formula (II) is preferably selected from the group consisting of 1, 2, 3, 4, 5, 6, 7 and 8, even more preferably b of formula (II) is selected from the group consisting of 1, 2, 3 and 4. Most preferably b of formula (II) is 1, if —Z of formula (II) is a water-soluble carrier.

If —Z is a water-insoluble carrier, such as a hydrogel, such carrier is usually connected to such a high number of moieties —B⁰ that it is impossible to provide an upper limit for b of formula (II).

In one embodiment —Z of formula (II) is a water-insoluble carrier.

Preferably, such water-insoluble carrier is a hydrogel comprising a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In one embodiment, such water-insoluble carrier —Z of formula (II) is a PEG-based or hyaluronic acid-based hydrogel.

In a preferred embodiment such water-insoluble carrier —Z of formula (II) is a PEG-based hydrogel.

In an equally preferred embodiment such water-insoluble carrier —Z of formula (II) is a hyaluronic acid-based hydrogel.

Even more preferably, the carrier —Z of formula (II) is a hydrogel as described in WO 2006/003014 A2, WO 2011/012715 A1 or WO 2014/056926 A1, which are herewith incorporated by reference in their entirety.

In another embodiment —Z of formula (II) is a polymer network formed through the physical aggregation of polymer chains, which physical aggregation is preferably caused by hydrogen bonds, crystallization, helix formation or complexation. In one embodiment such polymer network is a thermogelling polymer.

In a preferred embodiment —Z of formula (II) is a water-soluble carrier.

Preferably, such water-soluble carrier —Z of formula (II) comprises a $C_{8-24}$ alkyl moiety or a polymeric moiety.

In one embodiment —Z of formula (II) comprises a $C_{8-24}$ alkyl moiety and derivatives thereof. Derivatives of $C_{8-24}$ alkyl moieties are those disclosed in WO 2005/027978 A2 and WO 2014/060512 A1 which are herewith incorporated by reference.

In a preferred embodiment —Z of formula (II) comprises a polymeric moiety.

Such polymeric moiety —Z of formula (II) may be a linear, branched, multi-arm or dendritic polymeric moiety.

In one embodiment —Z of formula (II) comprises a linear polymeric moiety.

In another embodiment —Z of formula (II) comprises a multi-arm polymeric moiety.

In another embodiment —Z of formula (II) comprises a dendritic polymeric moiety.

In a preferred embodiment —Z of formula (II) comprises a branched polymeric moiety.

Preferably, such polymer moiety —Z of formula (II) has a molecular weight ranging from 5 to 200 kDa. Even more preferably, —Z of formula (II) has a molecular weight ranging from 8 to 100 kDa, even more preferably ranging from 10 to 80 kDa, even more preferably from 12 to 60 kDa, even more preferably from 15 to 40 kDa and most preferably —Z of formula (II) has a molecular weight of about 20 kDa. In another equally preferred embodiment —Z of formula (II) has a molecular weight of about 40 kDa.

Preferably —Z of formula (II) comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropyl-methacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In one embodiment such water-soluble carrier —Z of formula (II) comprises a protein.

In one embodiment —Z of formula (II) comprises a carboxy-terminal peptide of chorionic gonadotropin as described in US 2012/0035101 A1 which is herewith incorporated by reference.

In another embodiment —Z of formula (II) comprises an albumin moiety.

In another embodiment —Z of formula (II) comprises an Fc fusion protein.

In another preferred embodiment —Z of formula (II) comprises a polysarcosine moiety.

In another preferred embodiment —Z of formula (II) comprises a poly(N-methylglycine) moiety.

In another preferred embodiment —Z of formula (II) comprises a random coil protein moiety.

In one preferred embodiment —Z of formula (II) comprises one random coil protein moiety.

In another preferred embodiment —Z of formula (II) comprises two random coil protein moieties.

In another preferred embodiment —Z of formula (II) comprises three random coil protein moieties.

In another preferred embodiment —Z of formula (II) comprises four random coil protein moieties.

In another preferred embodiment —Z of formula (II) comprises five random coil protein moieties.

In another preferred embodiment —Z of formula (II) comprises six random coil protein moieties.

In another preferred embodiment —Z of formula (II) comprises seven random coil protein moieties.

In another preferred embodiment —Z of formula (II) comprises eight random coil protein moieties.

Preferably, such random coil protein comprises at least 25 amino acid residues and at most 2000 amino acids. Even more preferably such random coil protein comprises at least 30 amino acid residues and at most 1500 amino acid residues. Even more preferably such random coil protein comprises at least 50 amino acid residues and at most 500 amino acid residues.

In a preferred embodiment, —Z of formula (II) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine and proline. Even more preferably, at least 10%, but less than 75%, preferably less than 65%, of the total number of amino acid residues of such random coil protein moiety are proline residues. Preferably, such random coil protein moiety is as described in WO 2011/144756 A1 which is hereby incorporated by reference in its entirety. Even more preferably —Z comprises at least one moiety selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:51 and SEQ ID NO:61 as disclosed in WO 2011/144756 A1 which are hereby incorporated by reference. A moiety comprising such random coil protein comprising alanine and proline will be referred to as "PA" or "PA moiety".

Accordingly, —Z of formula (II) may comprise a PA moiety.

In an equally preferred embodiment, —Z of formula (II) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, serine and proline. Even more preferably, at least 4%, but less than 40% of the total number of amino acid residues of such random coil protein moiety are proline residues. Preferably, such random coil protein moiety is as described in WO 2008/155134 A1 which is hereby incorporated by reference in its entirety. Even more preferably —Z comprises at least one moiety selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:40, SEQ ID NO:42, SEQ ID NO:44, SEQ ID NO:46, SEQ ID NO:50, SEQ ID NO:52, SEQ ID NO:54 and SEQ ID NO:56 as disclosed in WO 2008/155134 A1, which are hereby incorporated by reference. A moiety comprising such random coil protein moiety comprising alanine, serine and proline will be referred to as "PAS" or "PAS moiety".

Accordingly, —Z of formula (II) may comprise a PAS moiety.

In an equally preferred embodiment, —Z of formula (II) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, glycine and proline. A moiety comprising such random coil protein moiety comprising alanine, glycine and proline will be referred to as "PAG" or "PAG moiety".

Accordingly, —Z of formula (II) may comprise a PAG moiety.

In an equally preferred embodiment, —Z of formula (II) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from proline and glycine. A moiety comprising such random coil protein moiety comprising proline and glycine will be referred to as "PG" or "PG moiety".

Accordingly, —Z of formula (II) may comprise a PG moiety.

Preferably, such PG moiety comprises a moiety of formula (a-0)

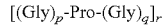   (a-0);

wherein
p is selected from the group consisting of 0, 1, 2, 3, 4 and 5;
q is selected from the group consisting of 0, 1, 2, 3, 4 and 5;
r is an integer ranging from and including 10 to 1000;
provided that at least one of p and q is at least 1;
Preferably, p of formula (a-0) is selected from the group consisting of 1, 2 and 3.

Preferably, q of formula (a-0) is selected from 0, 1 and 2.

Even more preferably the PG moiety comprises the sequence of SEQ ID:NO 1: GGPGGPGPGGPGGPGPGGPG.

Even more preferably, the PG moiety comprises the sequence of SEQ ID:NO 1 of formula (a-0-a)

   (a-0-a), wherein
v is an integer ranging from and including 1 to 50.

Accordingly, —Z of formula (II) may comprise a PG moiety.

In an equally preferred embodiment, —Z of formula (II) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, glycine, serine, threonine, glutamate and proline. Preferably, such random coil protein moiety is as described in WO 2010/091122 A1 which is hereby incorporated by reference. Even more preferably —Z comprises at least one moiety selected from the group consisting of SEQ ID NO:182, SEQ ID NO:183, SEQ ID NO:184; SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO:769, SEQ ID NO:770, SEQ ID NO:771, SEQ ID NO:772, SEQ ID NO:773, SEQ ID NO:774, SEQ ID NO:775, SEQ ID NO:776, SEQ ID NO:777, SEQ ID NO:778, SEQ ID NO:779, SEQ ID NO:1715, SEQ ID NO:1716, SEQ ID NO:1718, SEQ ID NO:1719, SEQ ID NO:1720, SEQ ID NO:1721 and SEQ ID NO:1722 as disclosed in WO 2010/091122 A1, which are hereby incorporated by reference. A moiety comprising such random coil protein moiety comprising alanine, glycine, serine, threonine, glutamate and proline will be referred to as "XTEN" or "XTEN moiety" in line with its designation in WO 2010/091122 A1.

Accordingly, —Z of formula (II) comprises an XTEN moiety.

In another preferred embodiment —Z of formula (II) comprises a hyaluronic acid-based polymer.

In another preferred embodiment —Z of formula (II) comprises a PEG-based polymer.

In one embodiment —Z of formula (II) comprises a branched or multi-arm PEG-based polymer. Most preferably, —Z of formula (II) comprises a multi-arm PEG-based polymer. Even more preferably, —Z of formula (II) comprises a multi-arm PEG-based polymer having at least 4 PEG-based arms.

In one embodiment —Z of formula (II) is a carrier as disclosed in WO 2013/024047 A1 which is herewith incorporated by reference.

In another embodiment —Z of formula (II) is a carrier as disclosed in WO 2013/024048 A1 which is herewith incorporated by reference.

Preferably, all moieties -A of formula (I) are the same.

In one embodiment all moieties -A of formula (I) are —X⁰, preferably all moieties -A of formula (I) are the same moieties —X⁰.

In another embodiment all moieties -A of formula (I) are —Y⁰, preferably all moieties -A of formula (I) are the same moieties —Y⁰.

Preferably, all moieties —B⁰ of formula (II) are the same.

In one embodiment all moieties —B⁰ of formula (II) are —X⁰, preferably all moieties —B⁰ of formula (I) are the same moieties —X⁰.

In another embodiment all moieties —B⁰ of formula (II) are —Y⁰, preferably all moieties —B⁰ of formula (I) are the same moieties —Y⁰.

Preferably, each —X⁰ of formula (I) and (II) is independently of formula (III):

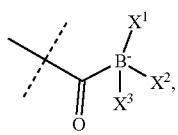

(III)

wherein
the dashed line indicates attachment to -L²- or -L²'-, respectively;
—X¹, —X² and —X³ are independently of each other selected from the group consisting of —F, —OR, —N⁺R₃, —N⁺R₂OR, —N⁺R₂SR and —N⁺R₂NR₂;
each —R is independently selected from the group consisting of —H, -T⁰, $C_{1-50}$ alkyl, $C_{2-50}$ alkenyl, and $C_{2-50}$ alkynyl; wherein -T⁰, $C_{1-50}$ alkyl, $C_{2-50}$ alkenyl, and $C_{2-50}$ alkynyl are optionally substituted with one or more —R$^{x1}$, which are the same or different and wherein $C_{1-50}$ alkyl, $C_{2-50}$ alkenyl, and $C_{2-50}$ alkynyl are optionally interrupted by one or more groups selected from the group consisting of -T⁰-, —C(O)O—, —O—, —C(O)—, —C(O)N(R$^{x2}$)—, —S(O)₂N(R$^{x2}$)—, —S(O)N(R$^{x2}$)—, —S(O)₂—, —S(O)—, —N(R$^{x2}$)S(O)₂N(R$^{x2a}$)—, —S—, —N(R$^{x2}$)—, —OC(OR$^{x2}$)(R$^{x2a}$)—, —N(R$^{x2}$)C(O)N(R$^{x2a}$)—, and —OC(O)N(R$^{x2}$)—;
each T⁰ is independently selected from the group consisting of phenyl, naphthyl, indenyl, indanyl, tetralinyl, $C_{3-10}$ cycloalkyl, 3- to 10-membered heterocyclyl, and 8- to 30-membered heteropolycyclyl; wherein each T⁰ is independently optionally substituted with one or more —R$^{x1}$, which are the same or different;
each —R$^{x1}$ is independently selected from the group consisting of halogen, -T⁰, —CN, oxo (=O), —COOR$^{x3}$, —OR$^{x3}$, —C(O)R$^{x3}$, —C(O)N(R$^{x3}$R$^{x3a}$), —S(O)₂N(R$^{x3}$R$^{x3a}$), —S(O)N(R$^{x3}$R$^{x3a}$), —S(O)₂R$^{x3}$, —S(O)R$^{x3}$, —N(R$^{x3}$)S(O)₂N(R$^{x3a}$R$^{x3b}$), —SR$^{x3}$, —N(R$^{x3}$R$^{x3a}$), —NO₂, —OC(O)R$^{x3}$, —N(R$^{x3}$)C(O)R$^{x3a}$, —N(R$^{x3}$)S(O)₂R$^{x3a}$, —N(R$^{x3}$)S(O)R$^{x3a}$, —N(R$^{x3}$)C(O)OR$^{x3a}$, —N(R$^{x3}$)C(O)N(R$^{x3a}$R$^{x3b}$), —OC(O)N(R$^{x3}$R$^{x3a}$), and $C_{1-6}$ alkyl; wherein $C_{1-6}$ alkyl is optionally substituted with one or more halogen, which are the same or different;
each —R$^{x2}$, —R$^{x2a}$, —R$^{x3}$, —R$^{x3a}$, —R$^{x3b}$ is independently selected from the group consisting of —H and $C_{1-6}$ alkyl; wherein $C_{1-6}$ alkyl is optionally substituted with one or more halogen, which are the same or different;
optionally, two or three of —X¹, —X² and —X³ are joined together with the atom to which they are attached to form a ring A⁰;

A⁰ is selected from the group consisting of 3- to 10-membered heterocyclyl and 8- to 30-membered heteropolycyclyl.

Typically, a counterion will also be present if there is no dative bond or cation within the ligand on boron, such as preferentially K⁺ or Cs⁺, but also —H⁺, Li⁺, Na⁺, R₄N⁺, R₄P⁺ or R₃S⁺=O, or mixtures thereof; wherein R is defined as in formula (III); preferably R is $C_{1-10}$ alkyl and most preferably $C_{1-4}$ alkyl.

In a first preferred embodiment all three substituents —X¹, —X² and —X³ of formula (III) are —F, i.e. the substituted acyl borate present in formula (III-i) is a trifluoroborate. Accordingly, a preferred substituted acyl borate of the present invention is of formula (III-i):

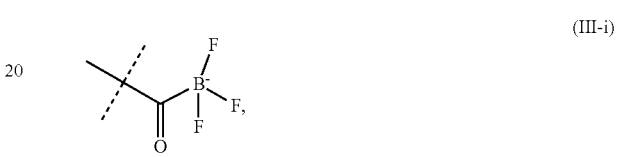

(III-i)

wherein
the dashed line indicates attachment to -L²- or -L²'-, respectively.

Even more preferably the counterion for the substituted acyl borate of formula (III-i) is potassium, i.e. K⁺.

Preparation of such acyl trifluoroborates starting from aldehydes has been described in Org Lett 2012, 14, 2138-2141.

In a second preferred embodiment —X¹ of formula (III) is —F and —X² and —X³ of formula (III) are both —OR, wherein —R is used as defined in formula (III). Preferably, —X² and —X³ are forming a 3- to 10-membered heterocycle or an 8- to 30-membered heteropolycycle.

Preferably, the substituted acyl borate of the present invention according to the second embodiment is selected from the group consisting of

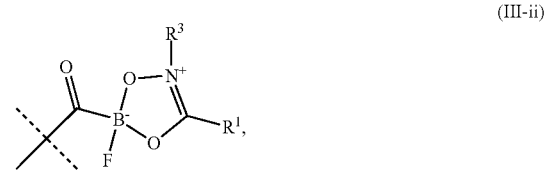

(III-ii)

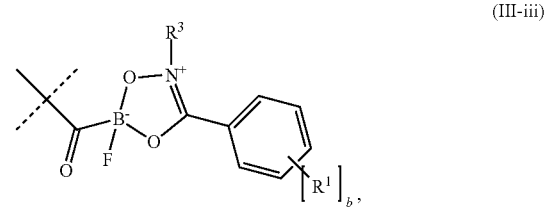

(III-iii)

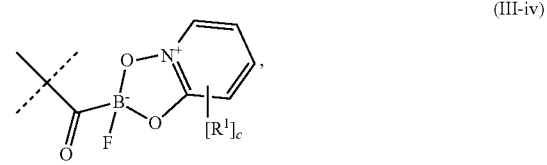

(III-iv)

-continued

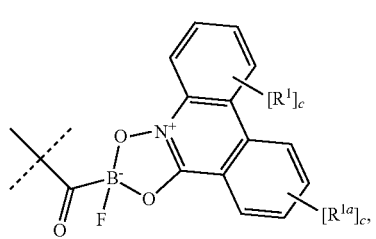
(III-v)

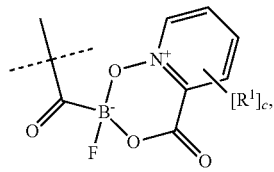
(III-vi)

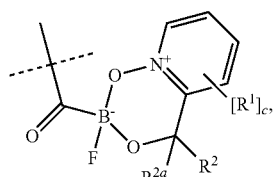
(III-vii)

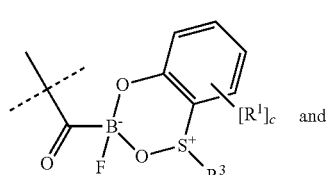
(III-viii)

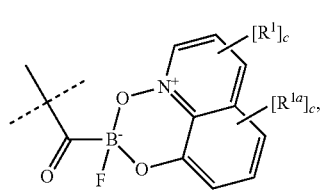
(III-ix)

wherein the dashed line indicates attachment to -L²- or -L²'-, respectively;

b is selected from the group consisting of 0, 1, 2, 3, 4 and 5;

each c is independently of each other selected from the group consisting of 0, 1, 2, 3 and 4;

—$R^1$, —$R^{1a}$, —$R^2$ and —$R^{2a}$ are independently of each other selected from the group consisting of —H, halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

—R$^3$ is selected from the group comprising of —H, -T$^0$, C$_{1-20}$ alkyl, C$_{2-20}$ alkenyl, C$_{2-20}$ alkynyl, which -T$^0$, C$_{1-20}$ alkyl, C$_{2-20}$ alkenyl, C$_{2-20}$ alkynyl are optionally substituted by one or more —R$^{x2}$ and —O—C$_{1-20}$ alkyl;

each —R$^{x1}$, —R$^{x1a}$, —R$^{x1b}$ is independently of each other selected from the group consisting of —H, -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 30-membered heteropolycyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different; and each —R$^{x3}$, —R$^{x3a}$, —R$^{x4}$, —R$^{x4a}$, —R$^{x4b}$ is independently selected from the group consisting of —H and C$_{1-6}$ alkyl; wherein C$_{1-6}$ alkyl is optionally substituted with one or more halogen, which are the same or different;

provided that the first atom of —R$^2$ and —R$^{2a}$ is a carbon atom.

Preferably, each —R$^1$, —R$^{1a}$, —R$^2$ and —R$^{2a}$ of formula (III-ii), (III-iii), (III-iv), (III-v), (III-vi), (III-vii), (III-viii) and (III-ix) is independently of each other selected from the group consisting of —H and methyl.

Preferably, each —R$^3$ of formula (III-ii), (III-iii) and (III-viii) is selected from the group consisting of —H and methyl. Most preferably —R$^3$ of formula (III-ii), (III-iii) and (III-viii) is methyl.

A preferred embodiment of (III-ii) is (III-ii-a):

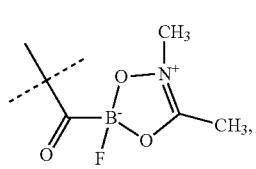
(III-ii-a)

wherein
the dashed line indicates attachment to -L²- or -L²'-, respectively.

A preferred embodiment of (III-iii) is (III-iii-a):

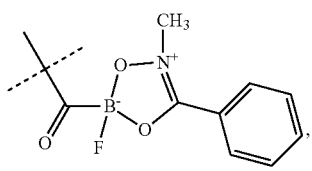

(III-iii-a)

wherein
the dashed line indicates attachment to -L²- or -L²'-, respectively.

A preferred embodiment of (III-viii) is (III-viii-a):

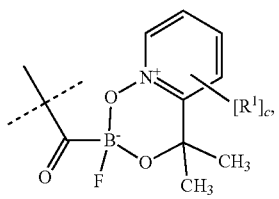

wherein
the dashed line indicates attachment to -L²- or -L²'-, respectively.

An even more preferred embodiment of (III-vii) is (III-vii-b):

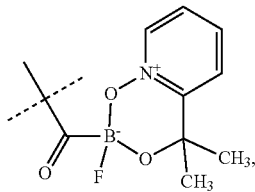

(III-vii-b)

wherein
the dashed line indicates attachment to -L²- or -L²'-, respectively.

A preferred embodiment of (III-viii) is (III-viii-a):

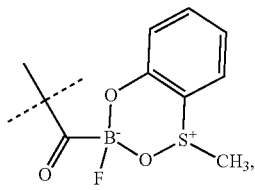

(III-viii-a)

wherein
the dashed line indicates attachment to -L²- or -L²'-, respectively.

A preferred embodiment of (III-ix) is (III-ix-a):

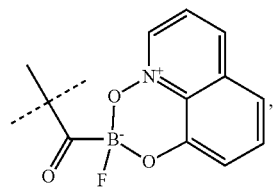

(III-ix-a)

the dashed line indicates attachment to -L²- or -L²'-, respectively.

Preferably, the substituted acyl borate according to the second embodiment is selected from the group consisting of (III-ii), (III-iii) and (III-ix).

In a third preferred embodiment —X¹ of formula (III) is —F, —X² of formula (III) is selected from the group consisting of —N⁺R₃, —N⁺R₂OR¹ᵃ, —N⁺R₂SR and —N⁺R₂NR₂ and —X³ of formula (III) is —OR, with —R being used as defined in formula (III). Preferably —X² and —X³ of formula (III) are forming a 3- to 10-membered heterocycle or an 8- to 30-membered heteropolycycle.

Preferably, the substituted acyl borate of the present invention according to the third embodiment is selected from the group consisting of

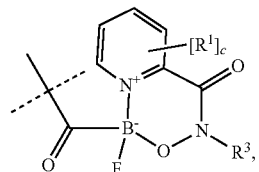

(III-x)

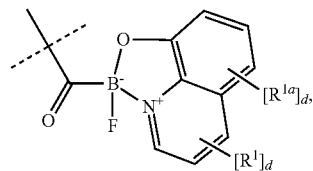

(III-xi)

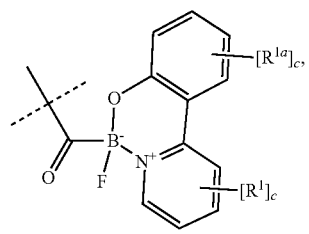

(III-xii)

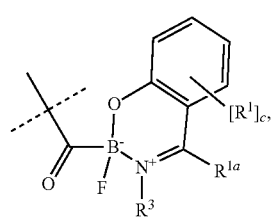

(III-xiii)

-continued

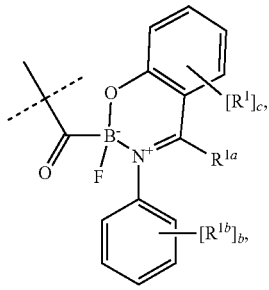

(III-xiv)

wherein
the dashed line indicates attachment to -L²- or -L²'-, respectively;
each b is selected from the group consisting of 0, 1, 2, 3, 4 and 5;
each c is independently of each other selected from the group consisting of 0, 1, 2, 3 and 4;
each d is independently of each other selected from the group consisting of 0, 1, 2 and 3;
—$R^1$, —$R^{1a}$ and —$R^{1b}$ are independently of each other selected from the group consisting of —H, halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T⁰, C$_{1-50}$ alkyl, C$_{2-50}$ alkenyl, and C$_{2-50}$ alkynyl; wherein -T⁰, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T⁰-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;
—$R^3$ is selected from the group —H, -T⁰, C$_{1-20}$ alkyl, C$_{2-20}$ alkenyl, C$_{2-20}$ alkynyl, which -T⁰, C$_{1-20}$ alkyl, C$_{2-20}$ alkenyl, C$_{2-20}$ alkynyl are optionally substituted by one or more —R$^{x2}$ and —O—C$_{1-20}$ alkyl;
each —R$^{x1}$, —R$^{x1a}$, —R$^{x1b}$ is independently of each other selected from the group consisting of —H, -T⁰, C$_{1-50}$ alkyl, C$_{2-50}$ alkenyl, and C$_{2-50}$ alkynyl; wherein -T⁰, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T⁰-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;
each T⁰ is independently selected from the group consisting of phenyl, naphthyl, indenyl, indanyl, tetralinyl, C$_{3-10}$ cycloalkyl, 3- to 10-membered heterocyclyl, and 8- to 30-membered heteropolycyclyl; wherein each T⁰ is independently optionally substituted with one or more —R$^{x2}$, which are the same or different;
each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different; and
each —R$^{x3}$, —R$^{x3a}$, —R$^{x4}$, —R$^{x4a}$, —R$^{x4b}$ is independently selected from the group consisting of —H and C$_{1-6}$ alkyl; wherein C$_{1-6}$ alkyl is optionally substituted with one or more halogen, which are the same or different.

Preferably, —$R^1$, —$R^{1a}$ and —$R^{1b}$ of formula (III-x), (III-xi), (III-xi), (III-xiii) and (III-xiv) are independently of each other selected from the group consisting of —H and methyl. Most preferably, —$R^1$, —$R^{1a}$ and —$R^{1b}$ of formula (III-x), (III-xi), (III-xi), (III-xiii) and (III-xiv) are —H.

Preferably, —$R^3$ of formula (III-x) and (III-xiii) is selected from the group consisting of —H and methyl. Most preferably —$R^3$ of formula (III-x) and (III-xiii) is methyl.

Preferably, the compound of formula (III-xii) is of formula (III-xii-a):

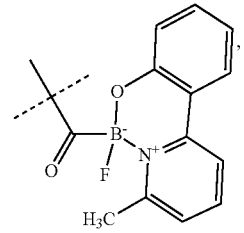

(III-xii-a)

wherein
the dashed line indicates attachment to -L²- or -L²'-, respectively.

A preferred embodiment of (III-xiii) is (III-xiii-a):

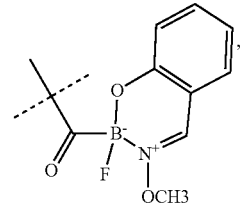

(III-xiii-a)

wherein
the dashed line indicates attachment to -L²- or -L²'-, respectively.

Preferably, the substituted acyl borate according to the third embodiment is selected from the group consisting of (III-xii) and (III-xiv). Most preferably the substituted acyl borate according to the third embodiment is of formula (III-xiv).

In another preferred embodiment, the substituted acyl borate of the present invention according to the third embodiment is selected from the group consisting of

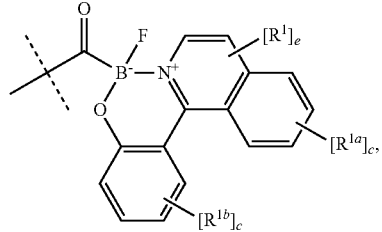

(III-a)

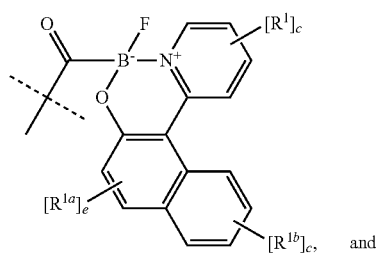

(III-b)

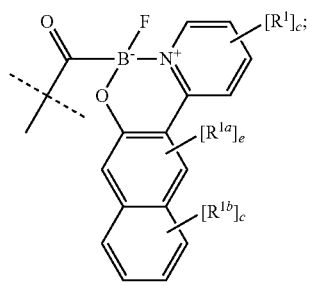

(III-c)

wherein the dashed line indicates attachment to -L$^2$- or -L$^{2'}$-, respectively;

each c is independently of each other selected from the group consisting of 0, 1, 2, 3 and 4;

each e is independently of each other selected from the group consisting of 0, 1 and 2;

—R$^1$, —R$^{1a}$ and —R$^{1b}$ are independently of each other selected from the group consisting of —H, halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —R$^{x1}$, —R$^{x1a}$, —R$^{x1b}$ is independently of each other selected from the group consisting of —H, -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 30-membered heteropolycyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different; and each —R$^{x3}$, —R$^{x3a}$, —R$^{x4}$, —R$^{x4a}$, —R$^{x4b}$ is independently selected from the group consisting of —H and C$_{1-6}$ alkyl; wherein C$_{1-6}$ alkyl is optionally substituted with one or more halogen, which are the same or different.

Preferably, —R$^1$, —R$^{1a}$ and —R$^{1b}$ of formula (III-a), (III-b) and (III-c) are independently of each other selected from the group consisting of —H and methyl. Most preferably, —R$^1$, —R$^{1a}$ and —R$^{1b}$ of formula (III-a), (III-b) and (III-c) are —H.

A preferred embodiment of (III-a) is (III-a-i):

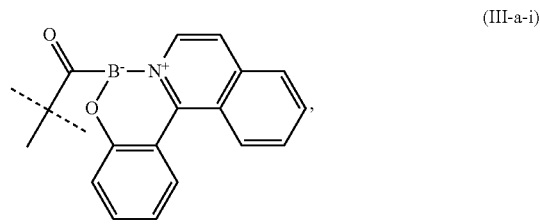

(III-a-i)

wherein the dashed line indicates attachment to -L$^2$- or -L$^{2'}$-, respectively.

A preferred embodiment of (III-b) is (III-b-i):

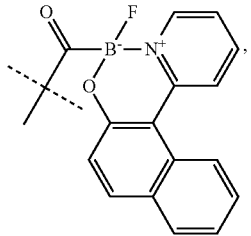
(III-b-i)

wherein
the dashed line indicates attachment to -L²- or -L²'-, respectively.

A preferred embodiment of (III-c) is (III-c-i):

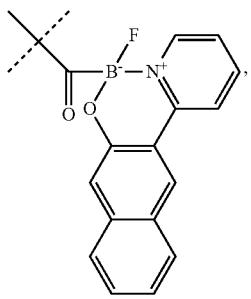
(III-c-i)

wherein
the dashed line indicates attachment to -L²- or -L²'-, respectively.

In a forth preferred embodiment —X¹ and —X³ of formula (III) are —OR, with —R being used as defined in formula (III), and —X² of formula (III) is selected from the group consisting of —N⁺R₃, —N⁺R₂OR¹ᵃ, —N⁺R₂SR and —N⁺R₂NR₂. Preferably, —X¹, —X² and —X³ of formula (III) form a 3- to 10-membered heterocycle or an 8- to 30-membered heteropolycycle.

Preferably, the substituted acyl borate of the present invention according to the forth embodiment is selected from the group consisting of

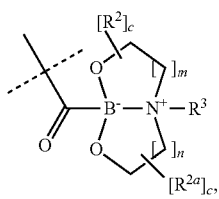
(III-xv)

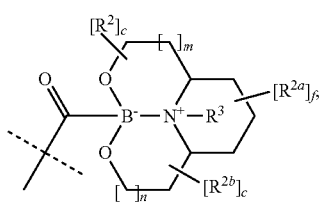
(III-xvi)

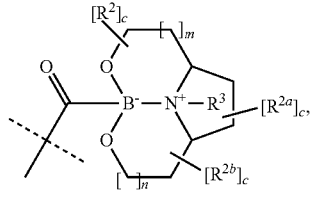
(III-xvii)

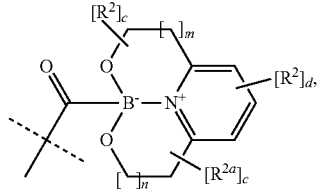
(III-xviii)

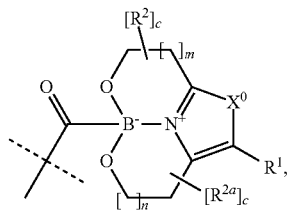
(III-xix)

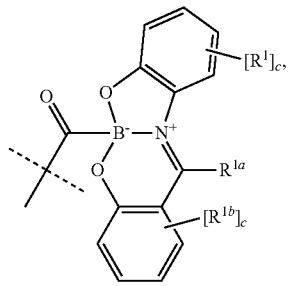
(III-xx)

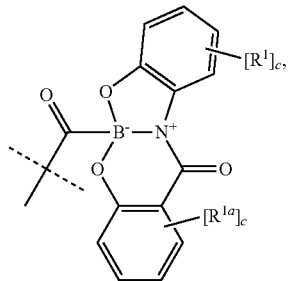
(III-xxi)

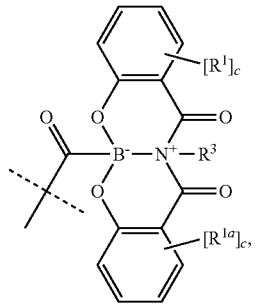
(III-xxii)

-continued (III-xxiii)
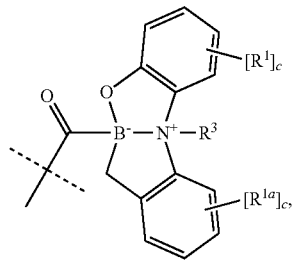

(III-xxiv)
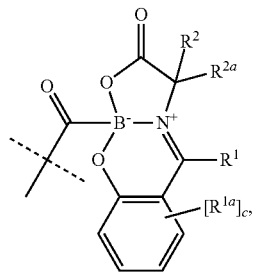

(III-xxv)
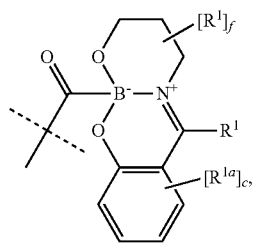

(III-xxvi)
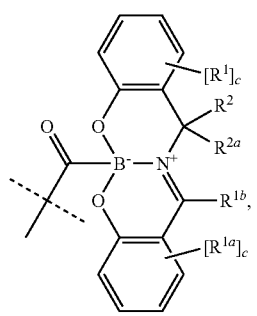

(III-xxvii)
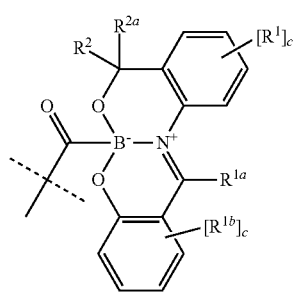 and (III-xxviii)
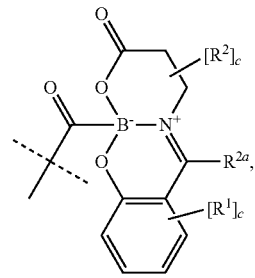

wherein
the dashed line indicates attachment to -L²- or -L²'-, respectively;
each c is independently of each other selected from the group consisting of 0, 1, 2, 3 and 4;
d is selected from the group consisting of 0, 1, 2 and 3;
f is selected from the group consisting of 0, 1, 2, 3, 4, 5 and 6;
m and n are independently of each other selected from the group consisting of 0, 1, 2 and 3;
—X⁰— is selected from the group consisting of —O—, —S—, —NH— and —NCH₃—;
—R¹, —R¹ᵃ, —R¹ᵇ, —R², —R²ᵃ, and —R²ᵇ are independently of each other selected from the group consisting of —H, halogen, —CN, —COOR$^{x1}$, —OR$^{x1}$, —C(O)R$^{x1}$, —C(O)N(R$^{x1}$R$^{x1a}$), —S(O)₂N(R$^{x1}$R$^{x1a}$), —S(O)N(R$^{x1}$R$^{x1a}$), —S(O)₂R$^{x1}$, —S(O)R$^{x1}$, —N(R$^{x1}$)S(O)₂N(R$^{x1a}$R$^{x1b}$), —SR$^{x1}$, —N(R$^{x1}$R$^{x1a}$), —NO₂, —OC(O)R$^{x1}$, —N(R$^{x1}$)C(O)R$^{x1a}$, —N(R$^{x1}$)S(O)₂R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T⁰, C$_{1-50}$ alkyl, C$_{2-50}$ alkenyl, and C$_{2-50}$ alkynyl; wherein -T⁰, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T⁰-, —C(O)O—, —O—, —C(O)—, —C(O)N(R$^{x3}$)—, —S(O)₂N(R$^{x3}$)—, —S(O)N(R$^{x3}$)—, —S(O)₂—, —S(O)—, —N(R$^{x3}$)S(O)₂N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;
—R³ is selected from the group —H, -T⁰, C$_{1-20}$ alkyl, C$_{2-20}$ alkenyl, C$_{2-20}$ alkynyl, which -T⁰, C$_{1-20}$ alkyl, C$_{2-20}$ alkenyl, C$_{2-20}$ alkynyl are optionally substituted by one or more —R$^{x2}$ and —O—C$_{1-20}$ alkyl;
each —R$^{x1}$, —R$^{x1a}$, —R$^{x1b}$ is independently of each other selected from the group consisting of —H, -T⁰, C$_{1-50}$ alkyl, C$_{2-50}$ alkenyl, and C$_{2-50}$ alkynyl; wherein -T⁰, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T⁰-, —C(O)O—, —O—, —C(O)—, —C(O)N(R$^{x3}$)—, —S(O)₂N(R$^{x3}$)—, —S(O)N(R$^{x3}$)—; —S(O)₂—, —S(O)—, —N(R$^{x3}$)S(O)₂N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;
each T⁰ is independently selected from the group consisting of phenyl, naphthyl, indenyl, indanyl, tetralinyl, C$_{3-10}$ cycloalkyl, 3- to 10-membered heterocyclyl, and 8- to 30-membered heteropolycyclyl; wherein each $T^0$ is independently optionally substituted with one or more $—R^{x2}$, which are the same or different;

each $—R^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different; and each $—R^{x3}$, $—R^{x3a}$, $—R^{x4}$, $—R^{x4a}$, $—R^{x4b}$ is independently selected from the group consisting of —H and $C_{1-6}$ alkyl; wherein $C_{1-6}$ alkyl is optionally substituted with one or more halogen, which are the same or different;

provided that the first atom of $—R^2$, $—R^{2a}$ and $—R^{2b}$ is a carbon atom, if $—R^2$, $—R^{2a}$ and $—R^{2b}$ are attached to a ring carbon which is next to a heteroatom.

Preferably, $—R^1$, $—R^{1a}$, $—R^{1b}$, $—R^2$, $—R^{2a}$, and $—R^{2b}$ of formula (III-xv), (III-xvi), (III-xvii), (III-xviii), (III-xix), (III-xx), (III-xxi), (III-xxii), (III-xxiii), (III-xxiv), (III-xxv), (III-xxvi), (III-xxvii) and (III-xxviii) are independently of each other selected from the group consisting of —H and methyl. Most preferably, $—R^1$, $—R^{1a}$, $—R^{1b}$, $—R^2$, $—R^{2a}$, and $—R^{2b}$ of formula (III-xv), (III-xvi), (III-xvii), (III-xviii), (III-xix), (III-xx), (III-xxi), (III-xxii), (III-xxiii), (III-xxiv), (III-xxv), (III-xxvi), (III-xxvii) and (III-xxviii) are —H.

Preferably, $—R^3$ of formula (III-xv), (III-xvi), (III-xvii), (III-xxii) and (III-xxii) is selected from the group consisting of —H and methyl. Most preferably $—R^3$ of formula (III-xv), (III-xvi), (III-xvii), (III-xxii) and (III-xxii) is methyl.

In a particularly preferred embodiment the substituted acyl borate according to the forth embodiment is of formula (III-xv), even more preferably of formula (III-xv-a):

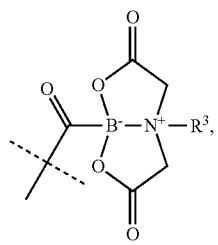

(III-xv-a)

wherein the dashed line indicates attachment to -L$^2$- or -L$^{2'}$-, respectively; and $—R^3$ is selected from —H, methyl, ethyl, propyl, and butyl.

In a fifth preferred embodiment $—X^1$, $—X^2$ and $—X^3$ of formula (III) are —OR, with —R being used as defined in formula (III). Preferably, $—X^1$, $—X^2$ and $—X^3$ of formula (III) form a 3- to 10-membered heterocycle or an 8- to 30-membered heteropolycycle.

Preferably, the substituted acyl borate of the present invention according to the fifth embodiment is selected from the group consisting of

(III-xxix)

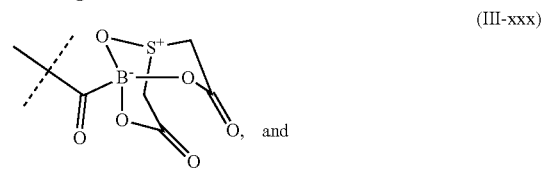

(III-xxx)

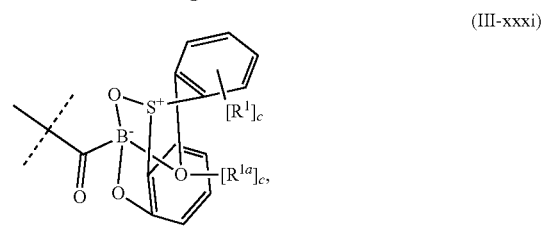

(III-xxxi)

wherein
the dashed line indicates attachment to -L$^2$- or -L$^{2'}$-, respectively;
each c is independently of each other selected from the group consisting of 0, 1, 2, 3 and 4; and
$—R^1$ and $—R^{1a}$ are independently of each other selected from the group consisting of —H, halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more $—R^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each $—R^{x1}$, $—R^{x1a}$, $—R^{x1b}$ is independently of each other selected from the group consisting of —H, -T$^0$, $C_{1-50}$ alkyl, $C_{2-50}$ alkenyl, and $C_{2-50}$ alkynyl; wherein -T$^0$, $C_{1-50}$ alkyl, $C_{2-50}$ alkenyl, and $C_{2-50}$ alkynyl are optionally substituted with one or more $—R^{x2}$, which are the same or different and wherein $C_{1-50}$ alkyl, $C_{2-50}$ alkenyl, and $C_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 30-membered heteropolycyclyl; wherein each $T^0$ is independently optionally substituted with one or more $—R^{x2}$, which are the same or different;

each $—R^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-6}$ alkyl; wherein $C_{1-6}$ alkyl is optionally substituted with one or more halogen, which are the same or different; and each $—R^{x3}$, $—R^{x3a}$, $—R^{x4}$, $—R^{x4a}$, $—R^{x4b}$ is independently selected from the group consisting of —H and $C_{1-6}$ alkyl; wherein $C_{1-6}$ alkyl is optionally substituted with one or more halogen, which are the same or different.

Preferably, $—R^1$ and $—R^{1a}$ of formula (III-xxxi) are independently of each other selected from the group consisting of —H, $C_{1-6}$ alkyl, $C_{2-6}$ alkenyl and $C_{2-6}$ alkynyl. Most preferably, $—R^1$ and $—R^{1a}$ of formula (III-xxxi) are —H.

In one embodiment -A of formula (I) is a substituted hydroxylamine, i.e. $—Y^0$. Preferably all moieties $—Y^0$ of formula (I) are the same.

In one embodiment $—B^0$ of formula (II) is a substituted hydroxylamine, i.e. $—Y^0$. Preferably all moieties $—Y^0$ of formula (II) are the same.

Preferably, each $—Y^0$ of formula (I) and (II) is independently of formula (IV):

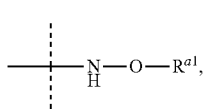

(IV)

wherein
the dashed line indicates attachment to -L$^2$- or -L$^{2'}$-, respectively;
—R$^{a1}$ is selected from the group comprising —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —S(O)$_2$OR$^{x1}$, —N(R$^{x1}$R$^{x1a}$), -T$^0$, $C_{1-20}$ alkyl, $C_{2-20}$ alkenyl, and $C_{2-20}$ alkynyl; wherein -T$^0$, $C_{1-20}$ alkyl, $C_{2-20}$ alkenyl, and $C_{2-20}$ alkynyl are optionally substituted with one or more $—R^{x2}$, which are the same or different and wherein $C_{1-20}$ alkyl, $C_{2-20}$ alkenyl, and $C_{2-20}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;
$—R^{x1}$, $—R^{x1a}$, $—R^{x1b}$ are independently of each other selected from the group consisting of —H, -T$^0$, $C_{1-10}$ alkyl, $C_{2-10}$ alkenyl, and $C_{2-10}$ alkynyl; wherein -T$^0$, $C_{1-10}$ alkyl, $C_{2-10}$ alkenyl, and $C_{2-10}$ alkynyl are optionally substituted with one or more $—R^{x2}$, which are the same or different and wherein $C_{1-10}$ alkyl, $C_{2-10}$ alkenyl, and $C_{2-10}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more $—R^{x2}$, which are the same or different;

each $—R^{x2}$ is independently selected from the group consisting of halogen, -T$^0$, —CN, oxo(=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and $C_{1-4}$ alkyl; wherein $C_{1-4}$ alkyl is optionally substituted with one or more halogen, which are the same or different;

each $—R^{x3}$, $—R^{x3a}$, $—R^{x4}$, $—R^{x4a}$, $—R^{x4b}$ is independently selected from the group consisting of —H and $C_{1-4}$ alkyl; wherein $C_{1-4}$ alkyl is optionally substituted with one or more halogen, which are the same or different.

Even more preferably, $—R^{a1}$ of formula (IV) is selected from the group consisting of methyl, ethyl, propyl,

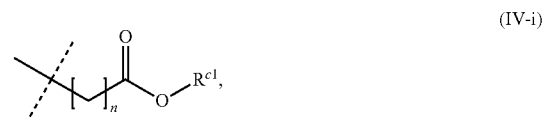

(IV-i)

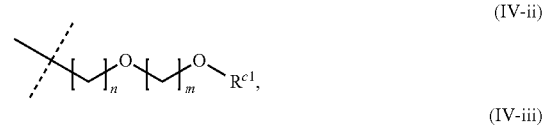

(IV-ii)

(IV-iii)

(IV-iv)

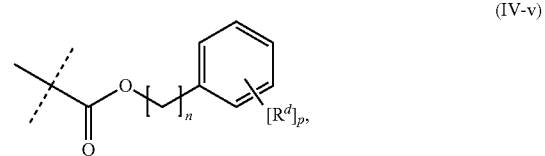

(IV-v)

-continued

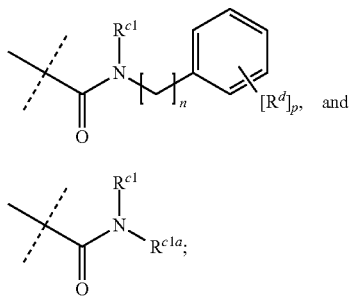

(IV-v)

(IV-vi)

wherein
—$R^{c1}$ and —$R^{c1a}$ are independently of each other selected from the group consisting of —H, -$T^0$ and $C_{1-6}$ alkyl;
—$R^d$ is selected from the group consisting of $C_{1-6}$ alkyl and —$NO_2$, —CN, —C(O)O$R^e$, —S(O)$_2$O$R^e$;
each -$T^0$ is independently of each other selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each -$T^0$ is independently optionally substituted with one or more —$R^e$, which are the same or different;
each —$R^e$ is independently selected from the group consisting of $C_{1-6}$ alkyl;
n is selected from the group consisting of 0, 1, 2, 3, 4, 5, 6, 7, 8, 9 and 10;
m is selected from the group consisting of 1, 2, 3, 4, 5, 6, 7, 8, 9 and 10;
p is selected from 0, 1, 2, 3, 4 and 5;
In one embodiment —$R^{a1}$ of formula (IV) is methyl.
In another embodiment —$R^{a1}$ of formula (IV) is ethyl.
In one embodiment —$R^{a1}$ of formula (IV) is propyl.
In one embodiment —$R^{a1}$ of formula (IV) is of formula (IV-i).
In one embodiment —$R^{a1}$ of formula (IV) is of formula (IV-ii).
In one embodiment —$R^{a1}$ of formula (IV) is of formula (IV-iii).
In one embodiment —$R^{a1}$ of formula (IV) is of formula (IV-iv).
In one embodiment —$R^{a1}$ of formula (IV) is of formula (IV-v).
In one embodiment —$R^{a1}$ of formula (IV) is of formula (IV-vi).
Most preferably —$R^{a1}$ of formula (IV)

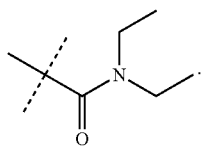

Preferably, all moieties -$L^2$- of formula (I) are the same.
In one embodiment -$L^2$- of formula (I) is a chemical bond.
Preferably, all moieties -$L^{2'}$- of formula (II) are the same.
In one embodiment -$L^{2'}$- of formula (II) is a chemical bond.
In another embodiment -$L^2$- of formula (I) is a spacer moiety. Preferably all spacer moieties are the same.
In another embodiment -$L^{2'}$- of formula (II) is a spacer moiety. Preferably all spacer moieties are the same.

If -$L^2$- of formula (I) or -$L^{2'}$- of formula (II) is a spacer, such spacer is preferably selected from the group consisting of -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;
—$R^{y1}$ and —$R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;
each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;
each —$R^{y2}$ is independently selected from the group consisting of halogen, —CN, oxo (=O), —COO$R^{y5}$, —O$R^{y5}$, —C(O)$R^{y5}$, —C(O)N($R^{y5}R^{y5a}$), —S(O)$_2$N($R^{y5}R^{y5a}$), —S(O)N($R^{y5}R^{y5a}$), —S(O)$_2R^{y5}$, —S(O)$R^{y5}$, —N($R^{y5}$)S(O)$_2$N($R^{y5a}R^{y5b}$), —S$R^{y5}$, —N($R^{y5}R^{y5a}$), —NO$_2$, —OC(O)$R^{y5}$, —N($R^{y5}$)C(O)$R^{y5a}$, —N($R^{y5}$)S(O)$_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and
each —$R^{y3}$, —$R^{y3a}$, —$R^{y4}$, —$R^{y4a}$, —$R^{y5}$, —$R^{y5a}$ and —$R^{y5b}$ is independently selected from the group consisting of —H, and $C_{1-6}$ alkyl, wherein $C_{1-6}$ alkyl is optionally substituted with one or more halogen, which are the same or different.
If -$L^2$- of formula (I) or -$L^{2'}$- of formula (II) is a spacer, such spacer is even more preferably selected from -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more —$R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more —$R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

—$R^{y2}$ is selected from the group consisting of halogen, —CN, oxo (=O), —COO$R^{y5}$, —O$R^{y5}$, —C(O)$R^{y5}$, —C(O)N($R^{y5}R^{y5a}$), —S(O)$_2$N($R^{y5}R^{y5a}$), —S(O)N($R^{y5}R^{y5a}$), —S(O)$_2R^{y5}$, —S(O)$R^{y5}$, —N($R^{y5}$)S(O)$_2$N($R^{y5a}R^{y5b}$), —S$R^{y5}$, —N($R^{y5}R^{y5a}$), —NO$_2$, —OC(O)$R^{y5}$, —N($R^{y5}$)C(O)$R^{y5a}$, —N($R^{y5}$)S(O)$_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different.

If -$L^2$- of formula (I) or -$L^{2'}$- of formula (II) is a spacer, such spacer is even more preferably selected from the group consisting of -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —$R^{y2}$ is independently selected from the group consisting of halogen, and $C_{1-6}$ alkyl; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different.

In a preferred embodiment -$L^2$- of formula (I) and -$L^{2'}$- of formula (II) are selected from the group consisting of $C_{1-10}$ alkyl, phenyl, naphthyl, azulenyl, indenyl, indanyl, $C_{3-10}$ cycloalkyl, 3- to 10-membered heterocyclyl and -A and —$B^0$ are —$X^0$. Preferably -$L^2$- of formula (I) and -$L^{2'}$- of formula (II) is selected from the group consisting of $C_{1-10}$ alkyl and phenyl and -A and —$B^0$ are —$X^0$.

In another preferred embodiment -$L^2$- of formula (I) and -$L^{2'}$- of formula (II) are $C_{1-10}$ alkyl, preferably $C_6$ alkyl, and -A and —$B^0$ are —$Y^0$.

The method of the present invention is conducted under aqueous conditions, i.e. in an aqueous buffer, which aqueous buffer may comprise additives. Preferably, the reaction is conducted in a solvent mixture selected from the group consisting of THF/$H_2O$, $CH_3CN$/$H_2O$, tBuOH/$H_2O$ and DMSO/tBuOH/$H_2O$. In general, ratios of 7:3 to 3:7 have been found to be advantageous. Best results have so far been observed for a 1:1 mixture of tBuOH/$H_2O$.

Preferably, the method of the present invention is performed at a pH ranging from and including 1 to 8, more preferably ranging from and including 2 to 6, even more preferably from and including 3 to 5. Even more preferably, the method of the present invention is performed at a pH of about 4, most preferably at pH 4. The pH is preferably adjusted by the addition of acid, more preferably by the addition of HCl, TFA, oxalic acid, AcOH and/or $H_3PO_4$.

Preferably, the method of the present invention is conducted at room temperature or slightly elevated temperature. Suitable reaction temperatures range from and including about –20° C. to about 160° C., with a temperature of about 10° C. to about 60° C. being preferred. Particularly preferred are reaction temperatures of about 20° C. to about 40° C. and even more preferred are reaction temperatures ranging from and including 20° C. to 26° C. Most preferred is a reaction temperature of about 20° C.

Preferably, the method of the present invention is performed for 1 minute to 5 hours, more preferably for 3 minutes to 2 hours, even more preferably for 5 minutes to 1 hour.

Particularly preferably, the method is performed under acidic conditions in a 1:1 mixture of tBuOH/$H_2O$.

The reaction of the method of the present invention generally occurs upon simple mixing the reagents of formula (I) and (II), in which one of -A and —$B^0$ is a substituted acyl borate and the other a substituted hydroxylamine.

The method of the present invention is highly chemoselective, such that the presence of unprotected functional groups on —Z, -D, -$L^1$-, -$L^2$- and -$L^{2'}$- does not interfere with it.

In particular, —Z, -D, -$L^1$-, -$L^2$- and -$L^{2'}$- may comprise one or more unprotected functional groups selected from the group consisting of carboxylic acid, hydroxyl, phenol, thiol, amine, ammonium, guanidine, guanidinium, imidazole, indole, and methyl thioether. It has been found that none of these functional groups will undergo a reaction with the substituted acyl borate under the above described reaction conditions.

Furthermore, the reaction also proceeds extremely fast: a second order rate constant of >20 $M^{-1}s^{-1}$ has been measured. Consequently, these reactions enable selective conjugations of large molecules at micromolar concentrations using equimolar amounts of reactants.

EXAMPLES

Materials and Methods

Materials:

The protein moiety "PA" is obtained as described in WO 2011/144756 A1, wherein the sequence was a 20-mer of SEQ ID NO:1 as disclosed therein.

Hyaluronic acid (HA, 90-130 kDa lab grade, batch 214-9272) was purchased from Contipro Biotech, Czech Republic.

Sunbright® GL2-200PA, was purchased from NOF Europe N.V., Grobbendonk, Belgium.

Dipentafluorophenylcarbonate was obtained from IRIS Biotech GmbH, Germany.

COMU, EDC.HCl, NHS, TBTU and PyBOP were purchased from Novabiochem, Germany.

Fmoc-N-Me-Asp(OBn)-OH was obtained from Peptide International Inc., Louisville, KY, USA. All other protected amino acids were obtained from Bachem, Switzerland.

HMPB-ChemMatrix® resin, all other chemicals and solvents were purchased from Sigma-ALDRICH Chemie GmbH, Taufkirchen, Germany.

Polypeptides Fmoc-GP(80)-OH, Ac-GP(80)-OH and Fmoc-Lys(Cbz)-GP(80)-OH were synthesized by standard Fmoc synthesis strategy using a Biotage® Initiator+Alstra™ peptide synthesizer with microwave (Biotage AB, Sweden) on HMPB-ChemMatrix® resin preloaded with glycine. Besides standard Fmoc amino acids Fmoc-Gly-Pro-OH was used to introduce proline into the sequence. The sequence of GP(80) is SEQ ID NO:2: (GGPGGPGPGGPGGPGPGGPG)$_4$ Methods:

Reactions were performed with anhydrous solvents (DCM, THF, ACN, DMF, MeOH, NMP). Generally, reactions were stirred at room temperature and monitored by HPLC/MS or TLC.

RP-HPLC was performed on a XBridge BEH300 C18 OBD Prep 10 µm 30×150 mm or 5 µm 10×150 mm (Waters, Eschborn, Germany) connected to a Waters 600 or 2535 HPLC System and Waters 2487 or 2489 Absorbance detector, respectively. If not indicated otherwise, linear gradients of solution A (0.1% TFA in H$_2$O (v/v)) and solution B (0.1% TFA in acetonitrile (v/v)) were used. HPLC fractions containing product were combined and lyophilized.

Flash chromatography purifications were performed on an Isolera™ One system from Biotage AB, Sweden, using Biotage® KP-Sil silica cartridges and n-heptane, ethyl acetate, dichloromethane, acetonitrile and methanol as eluents. Products were detected at 254 nm. For products showing no absorbance above 240 nm fractions were screened by TLC or LC/MS.

HPLC-Electrospray ionization mass spectrometry (HPLC-ESI-MS) was performed on a Waters Acquity UPLC with an Acquity PDA detector coupled to a Thermo LTQ Orbitrap Discovery high resolution/high accuracy mass spectrometer or Waters Micromass ZQ or an Agilent technologies 1290 Infinity II system with a G4212A diode array and a G6120B single quad MS system. A Waters ACQUITY UPLC BEH300 C18 RP column (2.1×50 mm, 300 Å, 1.7 µm, flow: 0.25 mL/min; solvent A: water+0.04% TFA (v/v), solvent B: acetonitrile+0.05% TFA (v/v) was used in all cases.

Example 1

1d and 1e were synthesized according to the following scheme:

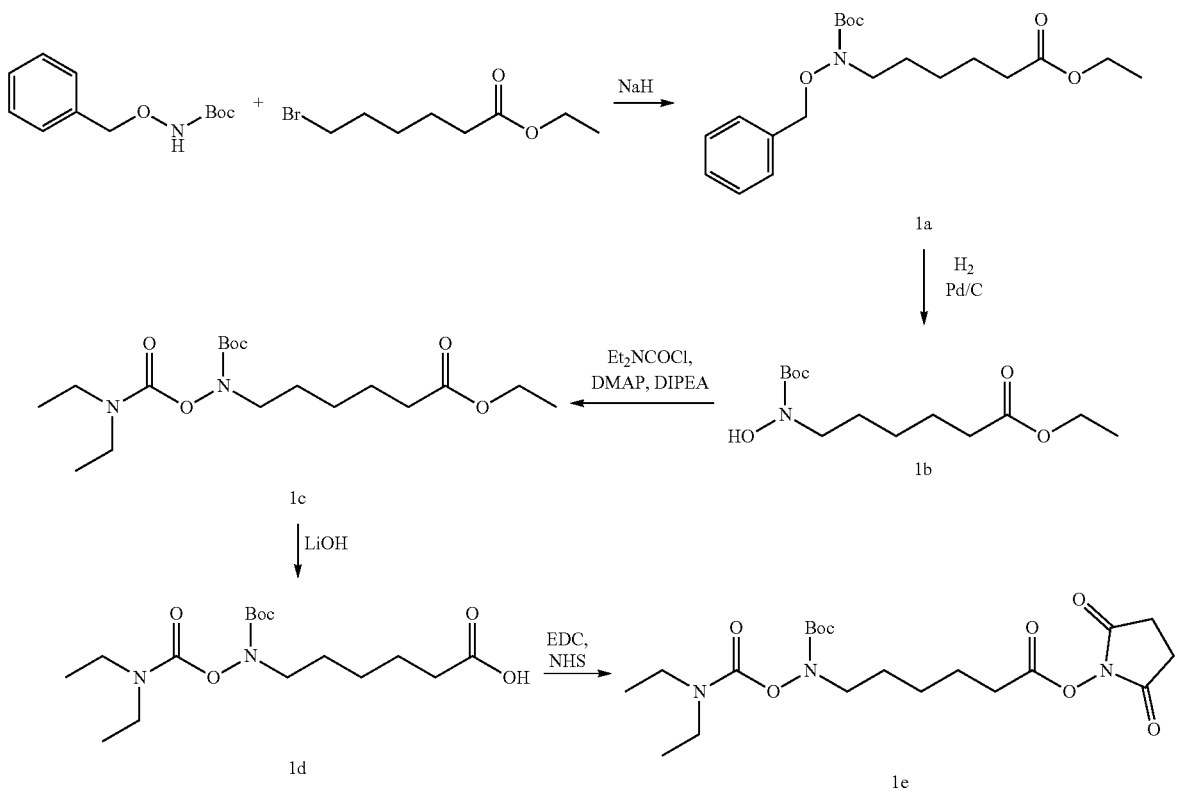

A solution of tert-butyl-N-(benzyloxy)carbamate (4.00 g, 17.9 mmol) in DMF (20 mL) was added slowly to a suspension of sodium hydride (60% in mineral oil) (0.932 g; 23.3 mmol) in DMF (52 mL) at 0° C. The reaction was stirred at 0° C. for 1 h, then ethyl 6-bromohexanoate (15.9 mL, 89.6 mmol) was added. The reaction mixture was stirred at room temperature for 1 hour. The reaction was quenched with sat. ammonium chloride solution (130 ml) and the mixture was extracted with DCM (3×200 ml). The combined organic layers were dried ($Na_2SO_4$), filtered and concentrated in vacuo. The obtained crude material (1a) was used in the next step without further purification.

1a was dissolved in methanol (140 mL). The solution was split in two equal parts and two reactions were carried out in parallel. 10% Pd/C (190 mg, 0.18 mmol) was added to each solution. The reaction mixtures were purged with $H_2$ and stirred under $H_2$-atmosphere (balloon) for 15.5 h. The reaction mixtures were filtered through a plug of celite, which was washed with MeOH. The volatiles were removed in vacuo. The crude product was purified by flash chromatography to yield 1b as colorless oil.

Yield: 4.73 g, 96% over 2 steps.

To a solution of 1b (4.70 g, 17.1 mmol) in DCM (150 mL), DMAP (688 mg, 5.63 mmol), DIPEA (5.95 mL, 34.1 mmol) and N,N-diethylcarbamoyl chloride (6.49 mL, 51.2 mmol) were added. The reaction mixture was stirred at room temperature for 14 h. The reaction was quenched with sat. ammonium chloride solution (180 ml) and the layers were separated. The aqueous phase was extracted with DCM (3×180 ml). The combined organic layers were dried ($Na_2SO_4$), filtered and concentrated in vacuo. The crude product was purified by flash chromatography to yield 1c as colorless oil.

Yield: 6.27 g, 98%.

1c (6.21 g, 16.6 mmol) was dissolved in a mixture of THF (186 mL), MeOH (62 mL) and water (62 mL). Lithium hydroxide (1.11 g, 46.4 mmol) was added and the reaction mixture was stirred for 4 h at room temperature. The reaction-mixture was cooled down in an ice bath and 1 M HCl was added until the pH reached pH 2. The mixture was extracted with 375 ml of ethyl acetate three times. The combined organic phase was dried ($Na_2SO_4$), filtered and concentrated in vacuo. The crude product was purified by flash chromatography to yield 1d as slightly yellow oil.

Yield: 5.27 g, 92%.

To a solution of 1d (1.97 g, 5.69 mmol) in DCM (15.8 mL), NHS (982 mg, 8.53 mmol) and EDC.HCl (1.64 g, 8.53 mmol) were added. The reaction mixture was stirred for 1.5 h at room temperature. The reaction mixture was diluted with 210 ml DCM and the solution was washed two times with 210 ml of 0.1 M aq. HCl and once with 210 ml of brine. The organic phase was dried ($Na_2SO_4$), filtered and concentrated in vacuo. The residue (1e) was used without further purification.

Yield: 2.72 g.

Example 2

Linker reagent 2f was synthesized according to the following scheme:

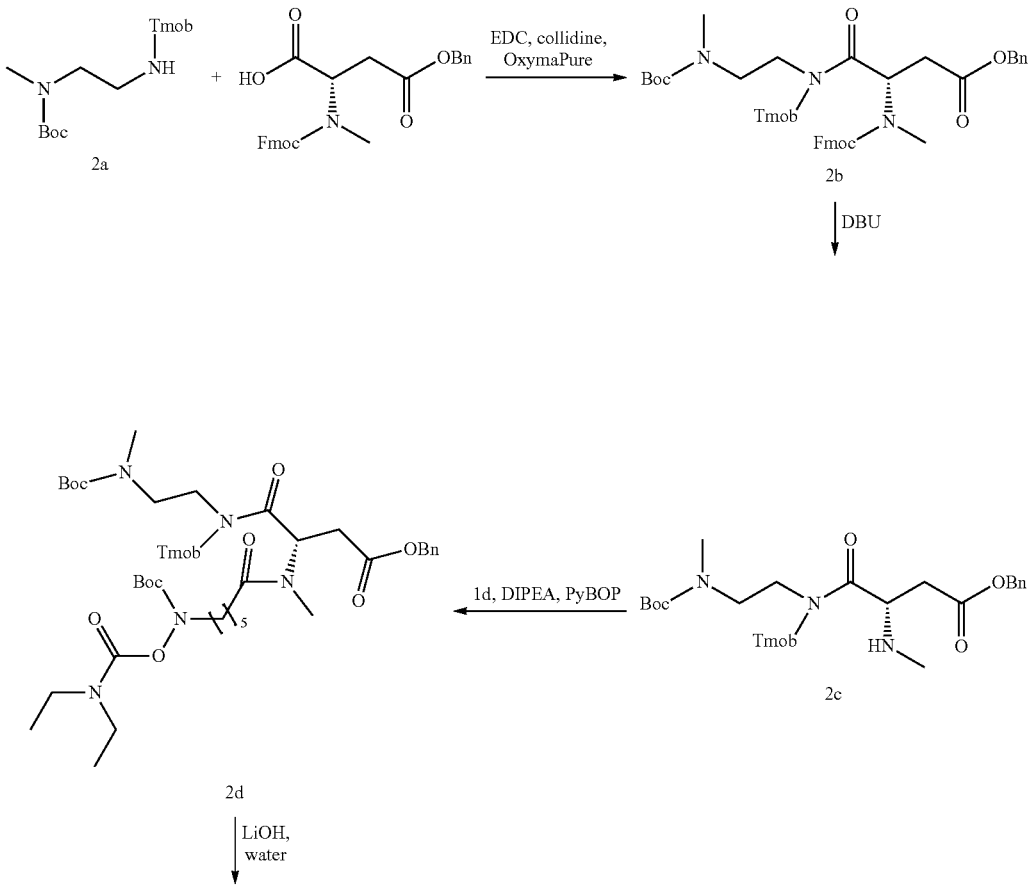

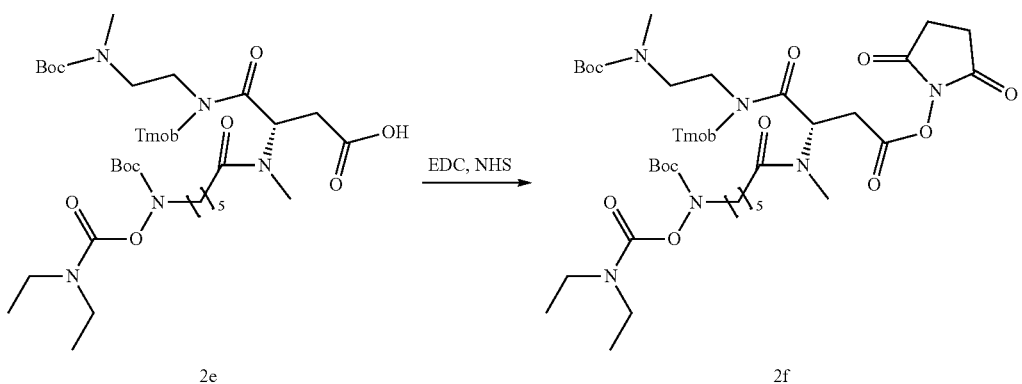

To a solution of N-methyl-N-Boc-ethylenediamine (2.05 ml, 11.48 mmol) and NaCNBH$_3$ (685 mg, 10.9 mmol) in MeOH (20 mL) was added 2,4,6-trimethoxybenzaldehyde (2.14 g, 10.9 mmol) as a solution in MeOH/DCM 1:1 v/v (40 ml) over 2 h. The mixture was stirred at room temperature for 1 h, acidified with 0.4 M HCl (60 mL) and stirred further 30 min. The reaction mixture was extracted 4 times with 150 mL ethyl acetate. The combined organic phase was washed with sat. NaHCO$_3$ solution (200 mL) and brine (90 mL), dried over Na$_2$SO$_4$ and the solvents were evaporated under reduced pressure. The resulting N-methyl-N-Boc-N'-Tmob-ethylenediamine 2a was dried in vacuo and used in the next reaction step without further purification.

Yield: 4.02 g, 99%, colorless oil.

To a solution of Fmoc-N-Me-Asp(OBzl)-OH (4.77 g, 10.4 mmol) in DCM (147 mL), EDC.HCl (2.58 g, 13.48 mmol), OxymaPure (2.06 g, 14.5 mmol) and 2,4,6-collidine (2.6 mL, 19.7 mmol) were added. The mixture was stirred for 5 minutes. A solution of 2a (3.97 g, 11.2 mmol) in DCM (36.8 mL) was added. The reaction mixture was stirred at room temperature for 2 h. The reaction was quenched with 300 mL of 0.1 M HCl. The aqueous phase was extracted twice with 80 mL DCM. The organic phases were combined and washed with sat. NaHCO$_3$ (1×140 mL, 2×70 mL) and brine (80 mL). The organic phase was dried over Na$_2$SO$_4$, filtrated and the residue concentrated in vacuo. 2b was purified using flash chromatography.

Yield: 6.73 g, 82%.

2b (6.71 g, 8.43 mmol) was dissolved in THF (67 mL). DBU (1.48 mL, 9.90 mmol) was added. The reaction mixture was stirred for 12 minutes. The reaction mixture was directly subjected to flash chromatography to yield 2c.

Yield: 4.63 g, 96%.

1d (800 mg, 2.31 mmol) was dissolved in DCM (7 ml). PyBOP (1.20 g, 2.31 mmol) and DIPEA (366 µL, 2.10 mmol) were added. Last, a solution of 2c (1.20 g, 2.10 mmol) in DCM (8 ml) was added. The reaction was stirred for 72 h. The reaction mixture was diluted with DCM (180 ml) and the solution was washed three times with 120 ml of 0.1 M aqueous HCl and one time with 120 ml of brine. The organic phase was dried over Na$_2$SO$_4$ and filtered. The solvent was evaporated. 2d was purified using flash chromatography.

Yield: 1.69 g, 89%.

2d (1.65 g, 1.83 mmol) was dissolved in a mixture of isopropanol (20 mL) and water (20 mL). LiOH (131 mg, 5.49 mmol) was added and the reaction stirred for 3 h. The reaction mixture was diluted with DCM (200 ml) and the solution was washed three times with 120 ml of 0.1 M aqueous HCl. The aqueous phase was extracted with 100 ml of dichloromethane and the organic phases were combined. The organic phase was washed with 120 mL of brine, dried over Na$_2$SO$_4$ and filtered. The solvent was evaporated. 2e was purified using flash chromatography.

Yield: 706 mg, 48%.

2e (363 mg, 0.45 mmol) was dissolved in DCM (4.36 mL). NHS (77 mg, 0.67 mmol), and EDC.HCl (129 mg, 0.67 mmol) were added. The reaction mixture was stirred for 5.7 h at room temperature. The reaction mixture was diluted with 100 ml DCM and the solution was washed two times with 66 ml of 0.1 M aqueous HCl and once with 66 ml of brine. The organic phase was dried over Na$_2$SO$_4$ and was filtered. The solvent was evaporated. 2f was purified using flash chromatography.

Yield: 319 mg, 78%.

Example 3

Linker reagent 3e was synthesized according to the following scheme:

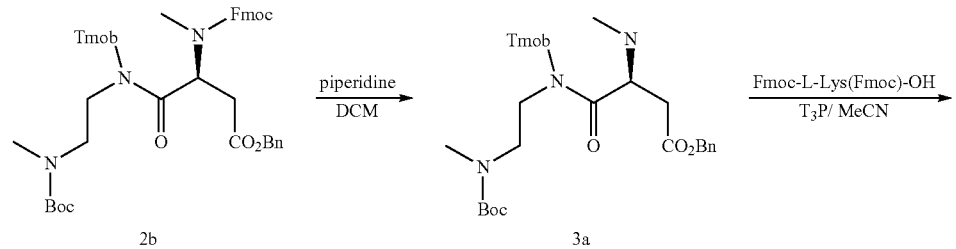

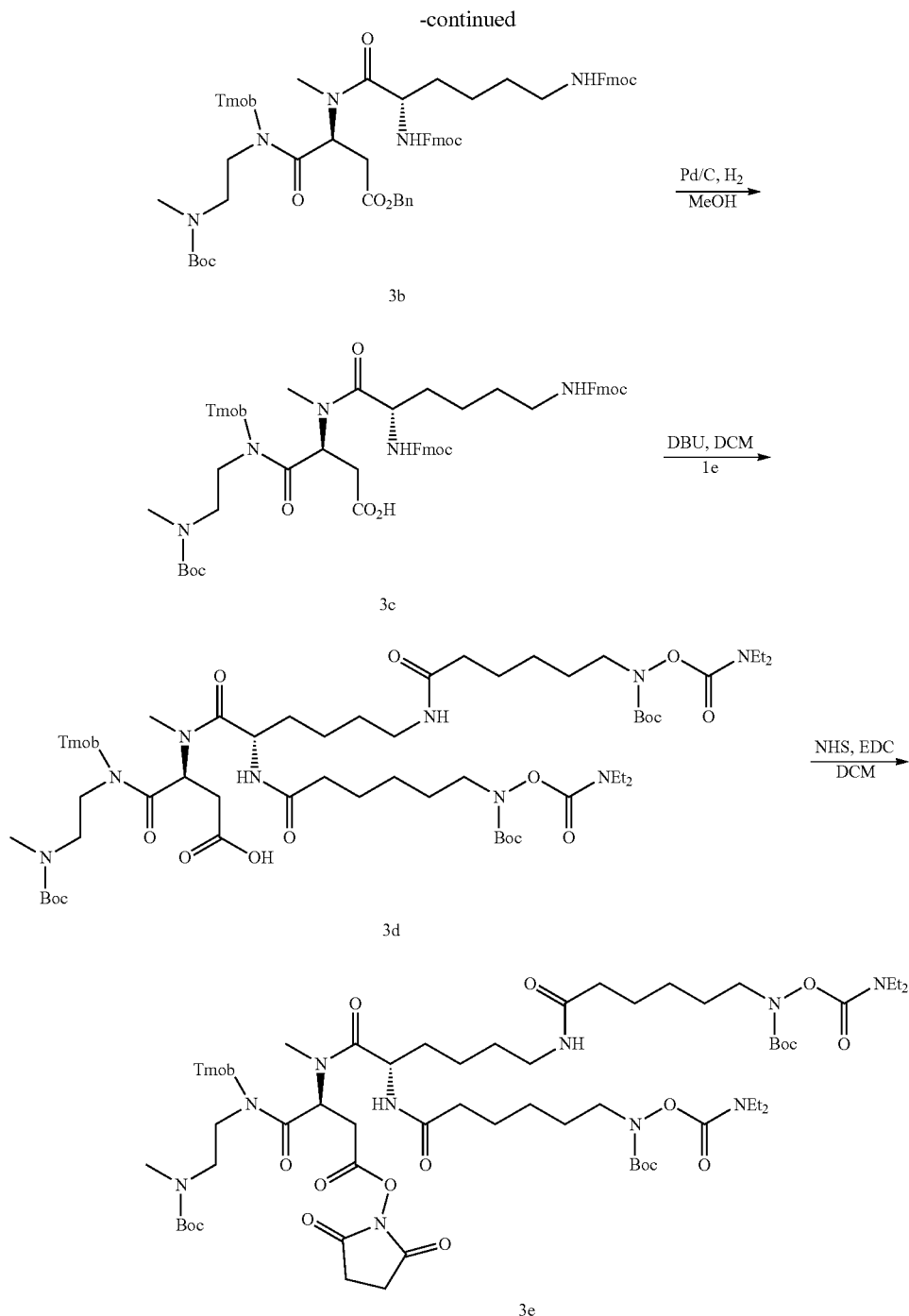

Four reactions were carried out in parallel. To a solution of compound 2b (60 g, 75 mmol) in CH$_2$Cl$_2$ (300 mL) was added piperidine (58 g, 0.68 mol, 67 mL). The reaction mixture was stirred at room temperature for 4 h. The four reactions which were performed in parallel were combined for work-up. The reaction mixture was diluted with H$_2$O (500 mL) and adjusted with a 0.5 N HCl solution to pH=3-4. The organic phase was separated and the aqueous phase was extracted with CH$_2$Cl$_2$ (800 mL). The combined organic phases were washed with brine (400 mL) and 5% saturated NaHCO$_3$ solution (400 mL). Then, the combined organic phases were dried over Na$_2$SO$_4$, filtered and the solvent was evaporated in vacuo. 3a was purified by chromatography on silica (100-200 mesh) with DCM/MeOH (20/1 to 4/1).

Yield: 150 g, 87%.

Two reactions were carried out in parallel. To a solution of Fmoc-Lys(Fmoc)-OH (79 g, 0.13 mol), 3a (70 g, 0.12 mol), 4-ethyl-morpholine (70 g, 0.61 mol, 77 mL) in MeCN (850 mL), T$_3$P (50% in EtOAc; 140 g, 0.22 mol) was added dropwise over a period of 30 min. After addition, the reaction mixture was stirred at room temperature for 18 h. The two reactions which were performed in parallel were combined for work-up. The reaction mixture was diluted with H$_2$O/CH$_2$Cl$_2$ (1:1, 2 L) and then adjusted with 0.5 N HCl solution to pH=3-4. The organic phase was separated and the aqueous phase was extracted with CH$_2$Cl$_2$ (1 L). The combined organic phases were washed with brine (800 mL) and 5% NaHCO$_3$ solution (800 mL) in turn. Then, the combined organic phases were dried over Na$_2$SO$_4$, filtered and the solvent was evaporated in vacuo. 3b was purified by chromatography on silica (100-200 mesh) with petroleum ether/ethyl acetate (5/1 to 1/1).

Yield: 160 g, 57%.

Two reactions were carried out in parallel. To a solution of 3b (60 g, 52 mmol) in MeOH (1.2 L) was added 10% Pd/C (18 g) in a 2 L vessel. The reaction mixture was degassed and purged 3× with H$_2$ and then stirred at 25° C. under H$_2$-atmosphere (45 psi) for 2.5 h. The two reactions which were performed in parallel were combined for work-up. The reaction mixture was filtered by diatomite and the filtrate was concentrated in vacuo to give crude 3c. 3c was purified by chromatography on silica (100-200 mesh) with DCM/MeOH (200/1 to 100/3).

Yield: 70 g, 63%.

MS: m/z 1056.4=[M+H]$^+$, (calculated monoisotopic mass=1056.50).

3c (1.10 g, 1.05 mmol) was dissolved in DCM (5.56 mL) and DBU (312 µL, 2.09 mmol) was added. The reaction mixture was stirred for 40 min. A solution of 1e (1.50 g, 3.14 mmol) in DCM (5.56 mL) was added. The reaction mixture was stirred for 30 min. The reaction mixture was diluted with ethyl acetate (240 mL) and washed three times with a mixture of 0.1 N HCl (150 mL) and brine (45 mL). The organic layer was dried over Na$_2$SO$_4$ and concentrated in vacuo. 3d was purified using flash chromatography.

Yield: 1.07 g, 81%.

3d (1.04 g, 0.82 mmol) was dissolved in DCM (12.5 mL). NHS (142 mg, 1.23 mmol) and EDC.HCl (236 mg, 1.23 mmol) were added. The reaction mixture was stirred for 3.5 h. The reaction mixture was diluted with 180 ml DCM and the solution was washed two times with 120 ml of 0.1 M aqueous HCl and once with 120 ml of brine. The organic phase was dried over Na$_2$SO$_4$ and was filtered. The solvent was evaporated. 3e was purified using flash chromatography.

Yield: 518 mg, 43%.

Example 4

Synthesis of CNP Linker Hydroxylamine:

Protected CNP was synthesized according to International application PCT/EP2017/050220 example 39c. The used CNP has the amino acid sequence of SEQ ID NO:3: LQEHPNARKYKGANKKGLSKGCFGLKLDRI-GSMSGLGC, wherein the cysteines at position 22 and 38 are connected through a disulfide-bridge. The linker was attached to lysine at position 26 according to the following scheme:

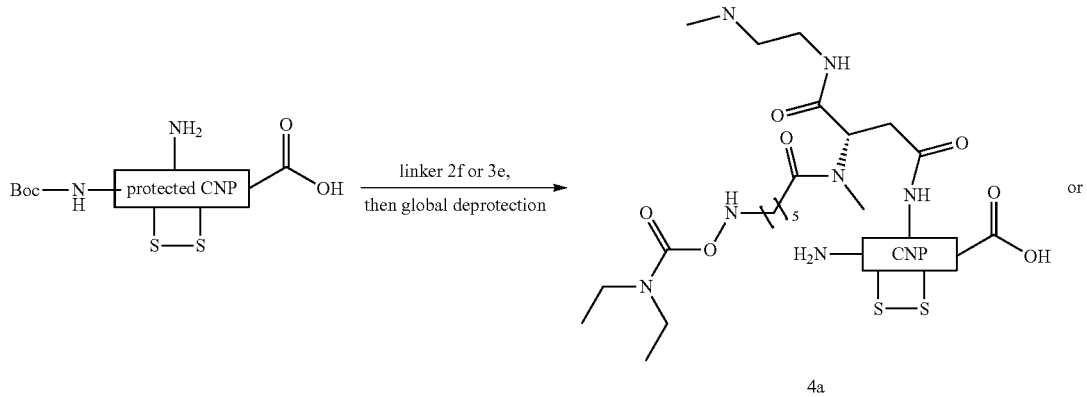

4a

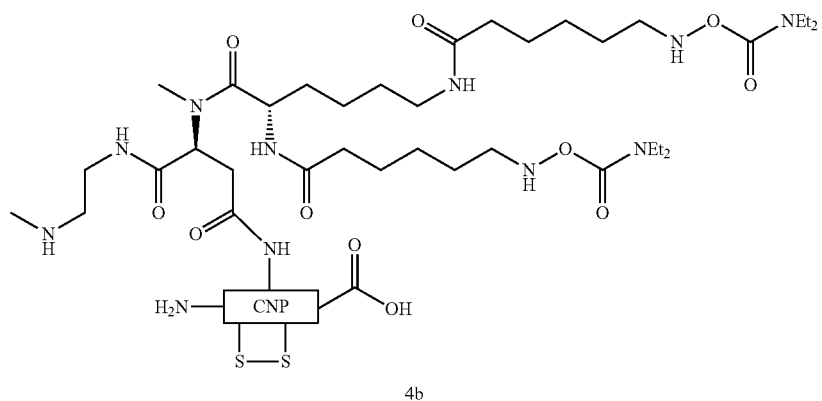

4b

General procedure: Protected CNP (1.0 eq) and the respective linker (2f or 3e, 1.1 eq) were dissolved in DMF (6.7 ml/g protected CNP). DIPEA (3 eq) was added and the reaction mixture was stirred for 20 h. The peptide was precipitated by addition of diethyl ether. The precipitate was washed twice with diethyl ether. The precipitate was dissolved in TFE/DCM and deprotected in TFA/TES/water/thioanisole 95:3:2.5:1 v/v/v/v for 1 h. The peptide was precipitated again with diethyl ether. The crude was purified by RP-HPLC.

4a: Yield: 10.6 mg, 30%, 10× TFA salt.

MS: m/z 1119.10=[M+4H]$^{4+}$, (calculated monoisotopic mass for [M+4H]$^{4+}$=1119.10).

was added to 45 ml heptane/diethyl ether 1:1. A white precipitate formed, and the suspension was kept at −20° C. for 30 minutes. The suspension was centrifuged, the supernatant was discarded and the residue washed once with 45 mL ice-cold heptane/diethyl ether 1:1. The residue was dried in vacuo. The crude material was purified by RP-HPLC with water/acetonitrile (no TFA) to yield 5.

Yield: 24 mg, 24%.

Example 6

Synthesis of KAT Functionalized 20 kDA-PEG

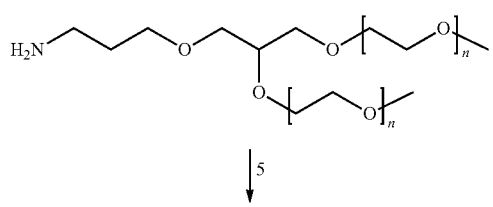

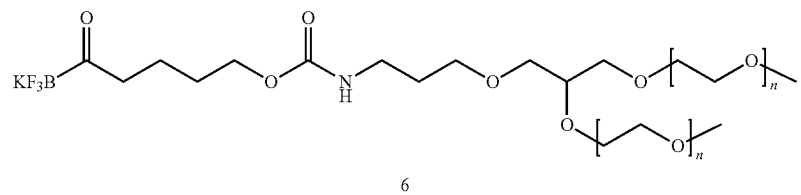

6

4b: Yield: 5.7 mg, 20%, 10× TFA salt.

MS: m/z 1208.16=[M+4H]$^{4+}$, (calculated monoisotopic mass for [M+4H]$^{4+}$=1208.16).

Example 5

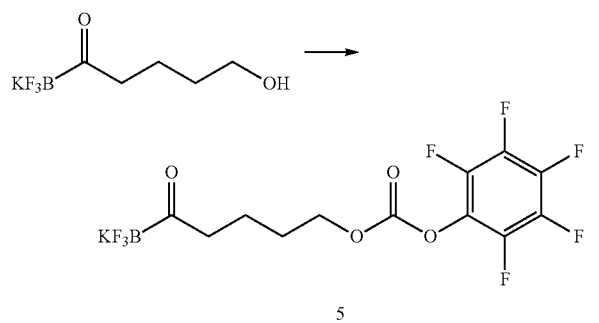

5

Potassium 5-hydroxypentanoyltrifluoroborate (50 mg, 0.24 mmol) and bis(pentafluorophenyl) carbonate (189 mg, 0.48 mmol) were dissolved in NMP (1 ml). The solution was cooled to 0° C. in an ice-bath and potassium carbonate (133 mg, 0.96 mmol) was added. The reaction mixture was stirred at room temperature for 2 h. The suspension was filtered and the precipitate was washed with NMP (0.5 ml). The filtrate Sunbright® GL2-200PA (20 kDa mPEG amine, 642 mg, 32 μmol) was dissolved in NMP (6.5 ml). Compound 5 (134 mg, 0.32 mmol) was dissolved in NMP (1.25 mL) and DIPEA (56 μL, 0.32 mmol) was added. Both solutions were mixed and stirred for 30 min. The product was precipitated in MTBE, dissolved in DCM and precipitated again from MTBE. The residue was dried in vacuo. 295 mg of this residue were further purified by dialysis (MWCO 3500) (3×0.1 M potassium phosphate buffer pH 7, 3× water). The product was lyophilized, dissolved in water, filtered and the filtrate was lyophilized.

Yield: 240 mg, 67%.

Example 7

Synthesis of H-GP(161)-OH

Fmoc-GP(80)-OH was synthesized by standard solid phase peptide synthesis. By coupling H-Gly-OtBu to the Fmoc-GP(80)-OH fragment in solution using PyBOP and DIPEA in DMF followed by Fmoc deprotection (20% piperidine in DMF), polypeptide H-GP(80)G-OtBu was obtained.

Fragment coupling of Fmoc-GP(80)-OH and H-GP(80)G-OtBu using PyBOP and DIPEA in DMSO and cleavage of protecting groups (Fmoc: 20% piperidine in DMF, tBu: 50% TFA in DCM) yielded polypeptide H-GP(161)-OH (7). Each intermediate and final polypeptide 7 were purified by RP-HPLC.

Yield: 87 mg of H-(GGPGGPGPGGPGGPGPGGPG)$_8$G-OH*1×TFA (7)

MS: m/z 818.52=[M+14H]$^{14+}$, (calculated monoisotopic mass for [M+14H]$^{14+}$=818.17).

Example 8

Synthesis of Ac-GP(80)-Lys-GP(81)-OH

Ac-GP(80)-OH and Fmoc-Lys(Cbz)-GP(80)-OH were synthesized on solid phase. H-Gly-OtBu was coupled to Fmoc-Lys(Cbz)-GP(80)-OH (PyBOP, DIPEA, NMP) in solution followed by Fmoc deprotection (20% piperidine in DMF) to yield H-Lys(Cbz)-GP(80)G-OtBu.

Fragment coupling of Ac-GP(80)-OH and H-Lys(Cbz)-GP(80)G-OtBu (PyBOP, DIPEA, DMSO) followed by global deprotection (Fmoc: 20% piperidine in DMF, tBu: 50% TFA in DCM, Cbz: $H_2$, Pd/C, DMF) produced polypeptide Ac-GP(80)-Lys-GP(81)-OH (8). Each intermediate and final product 8 were purified by RP-HPLC.

Yield: 133 mg of Ac-(GGPGGPGPGGPGGPGPGGPG)$_4$K(GGPGGPGPGGPGGPGPGGPG)$_4$G-OH*1×TFA (8)

MS: m/z 1659.76=[M+7H]$^{7+}$, (calculated monoisotopic mass for [M+7H]$^{7+}$=1659.63).

Example 9

Synthesis of KAT Functionalized GP-Polypeptides 9a and 9b:

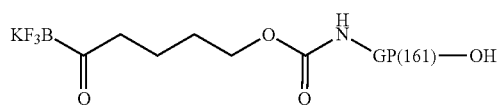
9a

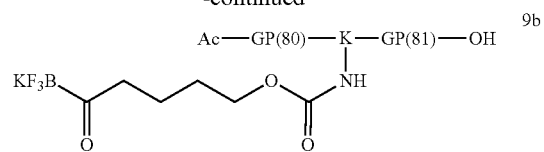
9b

Polypeptide 7 or 8 respectively (20 mg, 1.70 µmol) was dissolved in DMSO (250 µl). Potassium carbonate (2.4 mg, 17 µmol) was added. KAT reagent 5 (1.4 mg, 3.4 µmol) in 250 µl DMSO was added and the reaction stirred for 15 min. The resulting polypeptide (9a or 9b) was precipitated with diethyl ether (10 ml). The suspension was centrifuged, the supernatant decanted and the precipitate washed again with diethyl ether (10 ml). The residue was dried in vacuo and purified by RP-HPLC.

9a (using 7): 26.7 mg.

MS: m/z 894.57=[M-KF+13H]$^{13+}$, (calculated monoisotopic mass for [M-KF+13H]$^{13+}$=894.57).

9b (using 8): 9.5 mg.

MS: m/z 907.66=[M-KF+13H]$^{13+}$, (calculated monoisotopic mass for [M-KF+13H]$^{13+}$=907.65).

Example 10

The following conjugates were synthesized:

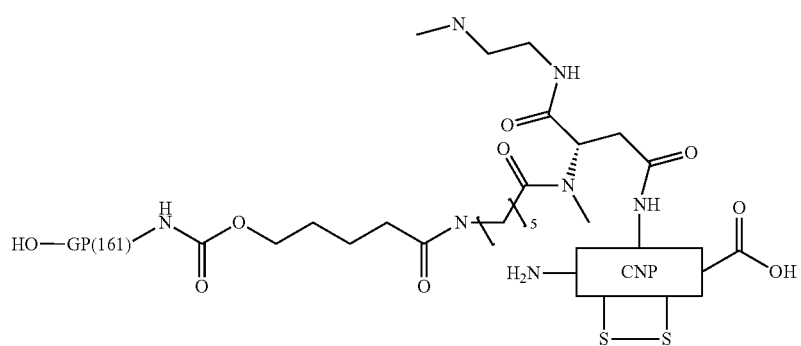
10a

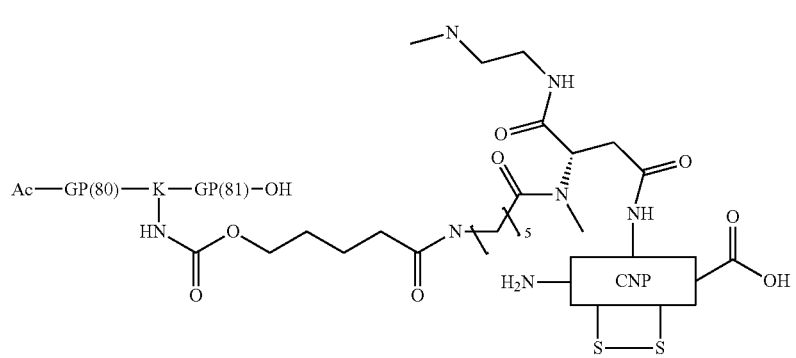
10b

-continued

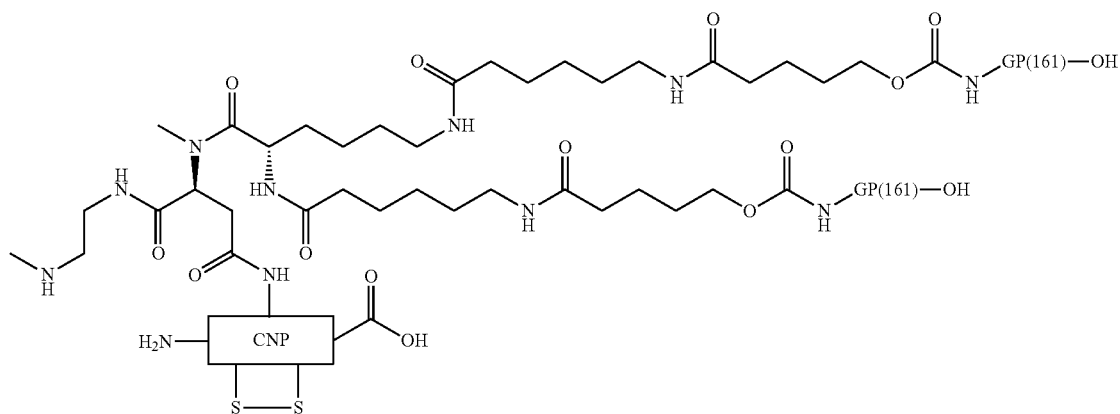

10c

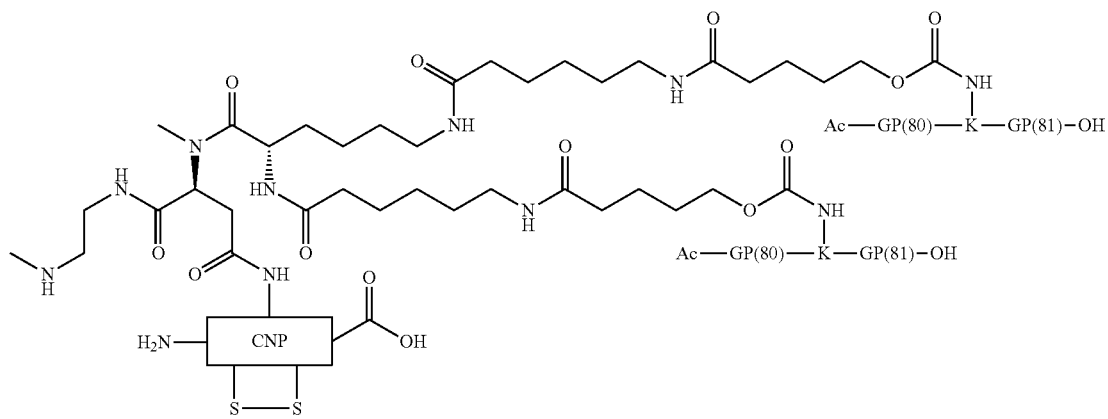

10d

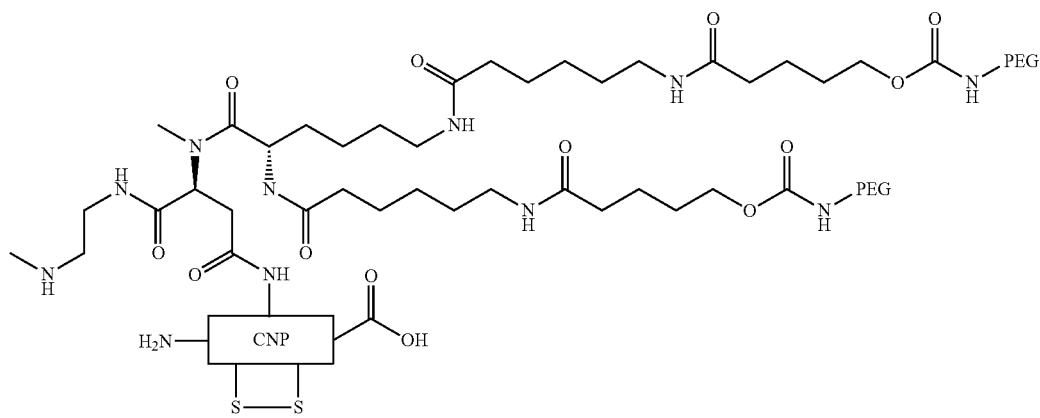

10e

10a: KAT functionalized polypeptide 9a (13.4 mg, 1.15 µmol) was used as stock solution in water (424 µl). CNP linker hydroxylamine 4a (4.5 mg, 0.8 µmol) was dissolved in ACN/water 1:1 containing 0.1% TFA v/v/v (5 ml). The KAT reagent solution was successively added until all CNP linker hydroxylamines reacted (total of 331 µl, 1 h reaction time) while the reaction was agitated. The product 10a was purified by RP-HPLC.

Yield: 4.1 mg, 30%.

MS: m/z 938.19=[M+17H]$^{17+}$, (calculated m/z for [M+17H]$^{17+}$=938.25).

10b: KAT functionalized polypeptide 9b (5 mg, 0.42 µmol) was used as stock solution in water (169 µl). CNP linker hydroxylamine 4a (2.0 mg, 0.35 µmol) was dissolved in ACN/water 1:1 containing 0.1% TFA v/v/v (140 µl). 28 µl 1 M sodium citrate buffer (pH 4) was added, then the KAT reagent solution (140 µl) was added and the reaction agitated for 15 min. The product 10b was purified by RP-HPLC.

Yield: 4.2 mg, 69%.

MS: m/z 947.98=[M+17H]$^{17+}$, (calculated m/z for [M+17H]$^{17+}$=948.26).

10c: KAT functionalized polypeptide 9a (7.7 mg, 0.5 µmol) was used as stock solution in water (100 µl). CNP linker hydroxylamine 4b (1.4 mg, 0.24 µmol) was dissolved in ACN/water 1:2 containing 0.1% TFA v/v/v (7.5 ml). The KAT reagent solution was successively added until all CNP linker hydroxylamines reacted (total of 82.5 µl, 5 h reaction time) while the reaction was agitated. The product 10c was purified by RP-HPLC.

Yield: 2 mg, 29%.

10d: KAT functionalized polypeptide 9b (4.3 mg, 0.36 µmol) was used as stock solution in water (100 µl). CNP linker hydroxylamine 4b (1.1 mg, 0.19 µmol) was dissolved in ACN/water 1:2 containing 0.1% TFA v/v/v (5.7 ml). The KAT reagent solution was successively added until all CNP linker hydroxylamines reacted (total of 95.2 µl, 1.5 h reaction time) while the reaction was agitated. The product 10d was purified by RP-HPLC.

Yield: 1.8 mg, 34%.

MS: m/z 1221.65=$[M+23H]^{23+}$, (calculated m/z for $[M+23H]^{23+}$=1222.23).

10e: PEG-KAT 6 was used as stock solution in water (50 mg/ml). CNP linker hydroxylamine 4b (4.2 mg, 0.7 µmol) was dissolved in 100 mM sodium citrate buffer (pH 4, 140 µl). 17.5 µl 1 M sodium citrate buffer (pH 3.9) containing 40 mM methionine was added to 160 µl of the PEG-KAT solution, then the solution of 4b (15 µl, 0.08 µmol) was added and the reaction agitated for 22 h. The product 10e was purified by SEC on an Aekta Purifier 100 system, using a Superdex 200 10/30 GL column and pH 7.4 buffer (10 mM phosphate, 140 mM NaCl, 3 mM KCl, 3 mM EDTA, 10 mM methionine, 0.03% Tween® 20) as eluent.

Example 11

Release Kinetics In Vitro

CNP conjugates 10a-d were dissolved in 60 mM sodium phosphate, 20 mM methionine, 3 mM EDTA, pH 7.4 at a concentration of 0.14 mg/mL. 10e was obtained from SEC in 10 mM phosphate, 140 mM NaCl, 3 mM KCl, 3 mM EDTA, 10 mM methionine, 0.03% Tween® 20, pH 7.4. The five solutions were incubated at 37° C. At various time points aliquots were withdrawn and analysed by RP-HPLC and ESI-MS. UV-signals were integrated and the ratio of the integral of liberated CNP to the total integrated area was plotted against incubation time.

Curve-fitting software was applied to estimate the corresponding half-life and plateau of release:

| compound | Half-life | plateau |
|---|---|---|
| 10a | 3.5 d | 98% |
| 10b | 3.7 d | 97% |
| 10c | 4.9 d | 98% |
| 10d | 4.9 d | 98% |
| 10e | 8.7 d | 98% |

The plateaus show near quantitative release of CNP.

Example 12

Synthesis of Carboxylic Acid 12

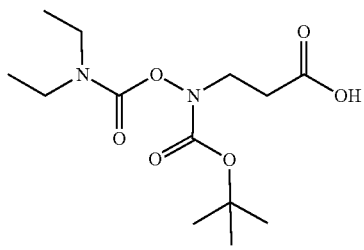

12

Carboxylic acid 12 was synthesized according to JACS 2014, 136, 5611 (supporting information pages S11-12).

Example 13

Synthesis of Hydroxylamine Functionalized TransCon Linker 13b

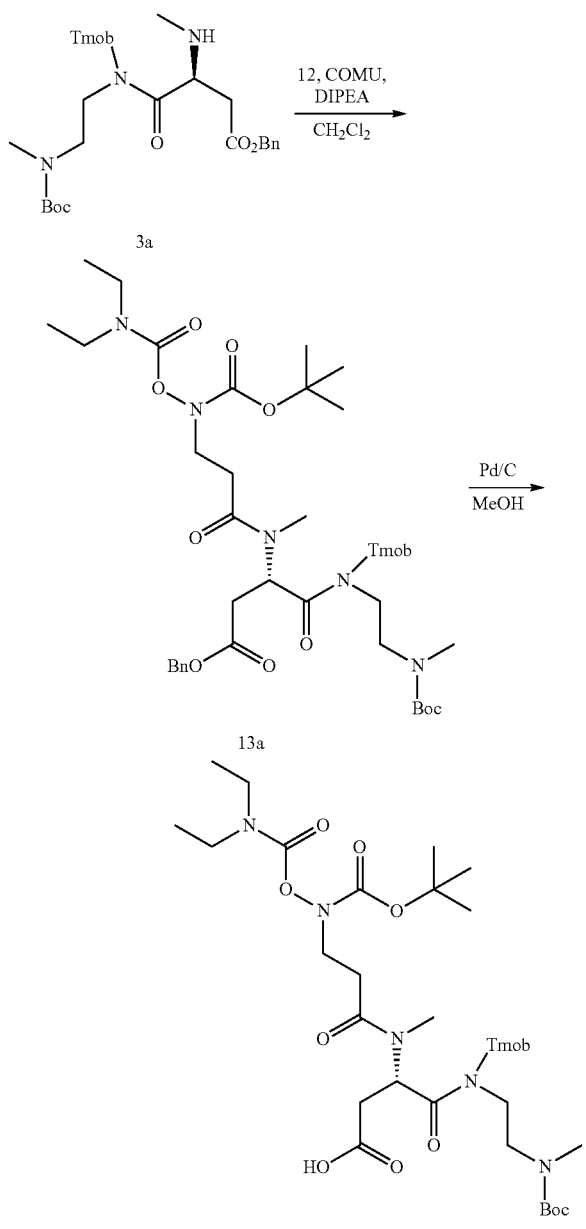

Building block 12 (1.2 eq), 3a (1 eq), COMU (2 eq) and DIPEA (4 eq) are stirred in CH$_2$Cl$_2$ until full conversion is observed by LCMS. The reaction mixture is diluted with CH$_2$Cl$_2$ and washed 3 times with 0.1 M HCl and 3× with brine. The combined aqueous phases are extracted with CH$_2$Cl$_2$. The combined organic phases are dried over Na$_2$SO$_4$, filtrated and concentrated. The crude material is purified using flash chromatography to yield 13a.

To a solution of 13a (45 g, 52 mmol) in MeOH (1.2 L) is added 10% Pd/C (18 g) in a 2 L hydrogenated bottle. The reaction mixture is degassed and purged three times with H₂ and then stirred at 25° C. under H₂-atmosphere (45 psi) for 2.5 h. The reaction mixture is filtered through diatomite and the filtrate is concentrated in vacuo to give crude 13b. 13b is purified by flash chromatography with CH₂Cl₂/MeOH.

Example 14

Synthesis of Linker Conjugate 14

Ramage resin ⟶

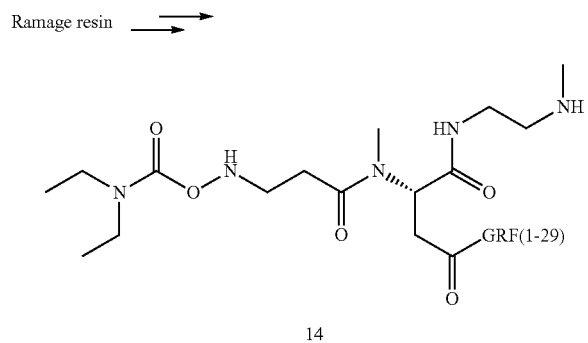

14

Product 14 is synthesized by Fmoc solid phase peptide synthesis starting with Ramage Resin (e.g. IRIS Biotech GmbH). GRF(1-29) refers to the following peptide sequence: H-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH₂. Protected amino acids and hydroxyl amine building block 13b are coupled with TBTU (2.5 eq) and DIPEA (5 eq) in DMF. Fmoc deprotections are performed with 2:2:96 piperidine/DBU/DMF. Side chain protecting groups and the peptide-resin bond are cleaved by stirring the protected product-resin in a cleavage cocktail consisting of 90:5:5 TFA/TES/H₂O. The crude material is purified by preparative HPLC. The product containing fractions are pooled and lyophilized to yield linker conjugate 14.

Example 15

Synthesis of KAT Reagent 15d

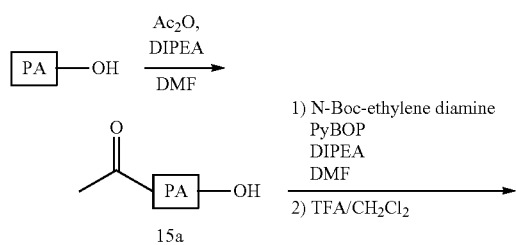

15a

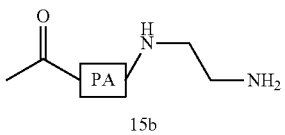

15b

Acetic acid anhydride (5 eq) is added to a solution of PA (1 eq) and DIPEA (10 eq) in DMF. The reaction mixture is stirred for 30 min at room temperature and the acetylated PA 15a is isolated by precipitation.

Ac-PA (1 eq), N-Boc-ethylene diamine (1.1 eq), PyBOP (1.5 eq) and DIPEA (3 eq) are dissolved in DMF and stirred until full conversion is observed. The product is purified by preparative HPLC. A solution of TFA/CH₂Cl₂ (1:1) is added to Ac-PA-NHCH₂CH₂NHBoc and stirred for 1 h at room temperature. The solution is concentrated and dried under high vacuum to yield 15b.

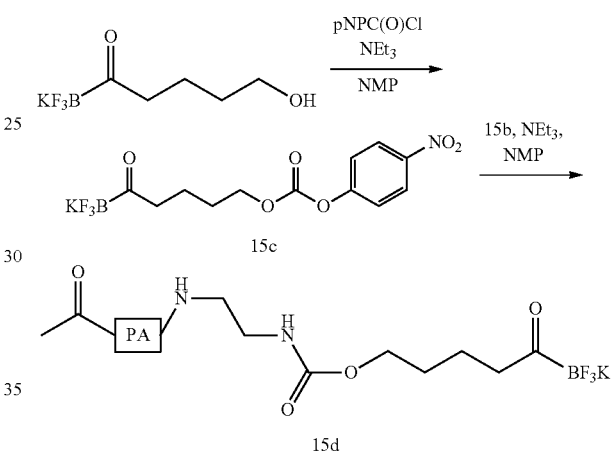

Potassium 5-hydroxypentanoyltrifluoroborate (1 eq), 4-nitrophenyl chloroformate (1 eq) and triethylamine (2 eq) are stirred in NMP. After 2 h product 15c is precipitated with Et₂O. Activated KAT reagent 15c is dissolved in NMP and 15b (1 eq) and NEt₃ (8 eq) in NMP are added and the reaction is stirred at room temperature. The product 15d is isolated by preparative HPLC using ACN/water as eluent.

Example 16

Synthesis of TransCon PA GRF(1-29)

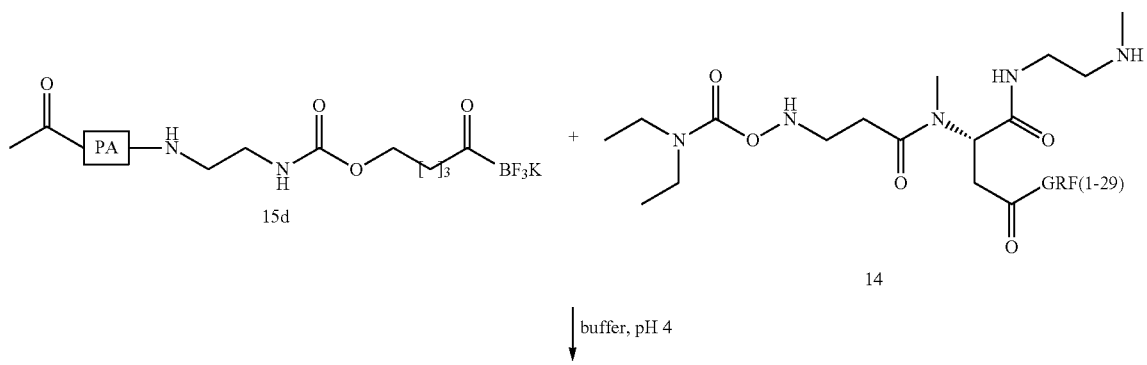

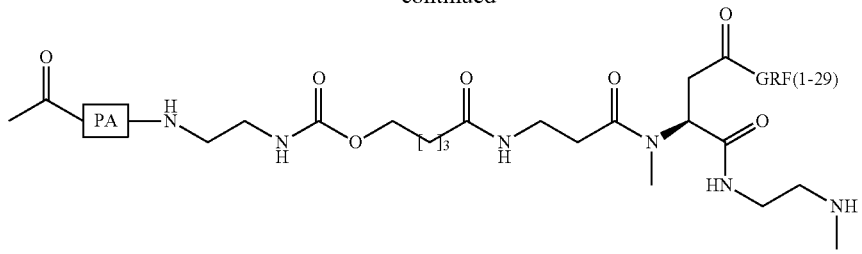
16
Building block 14 (1 eq) is reacted with KAT polymer 15d (1 eq) in potassium citrate buffer (pH 4) at room temperature. The mixture is stirred until good conversion is observed by LCMS. The product is purified by HPLC.
Accordingly, the reaction can be performed with HA-KAT reagent 17.
Example 17
Synthesis of HA-KAT Reagent 17b
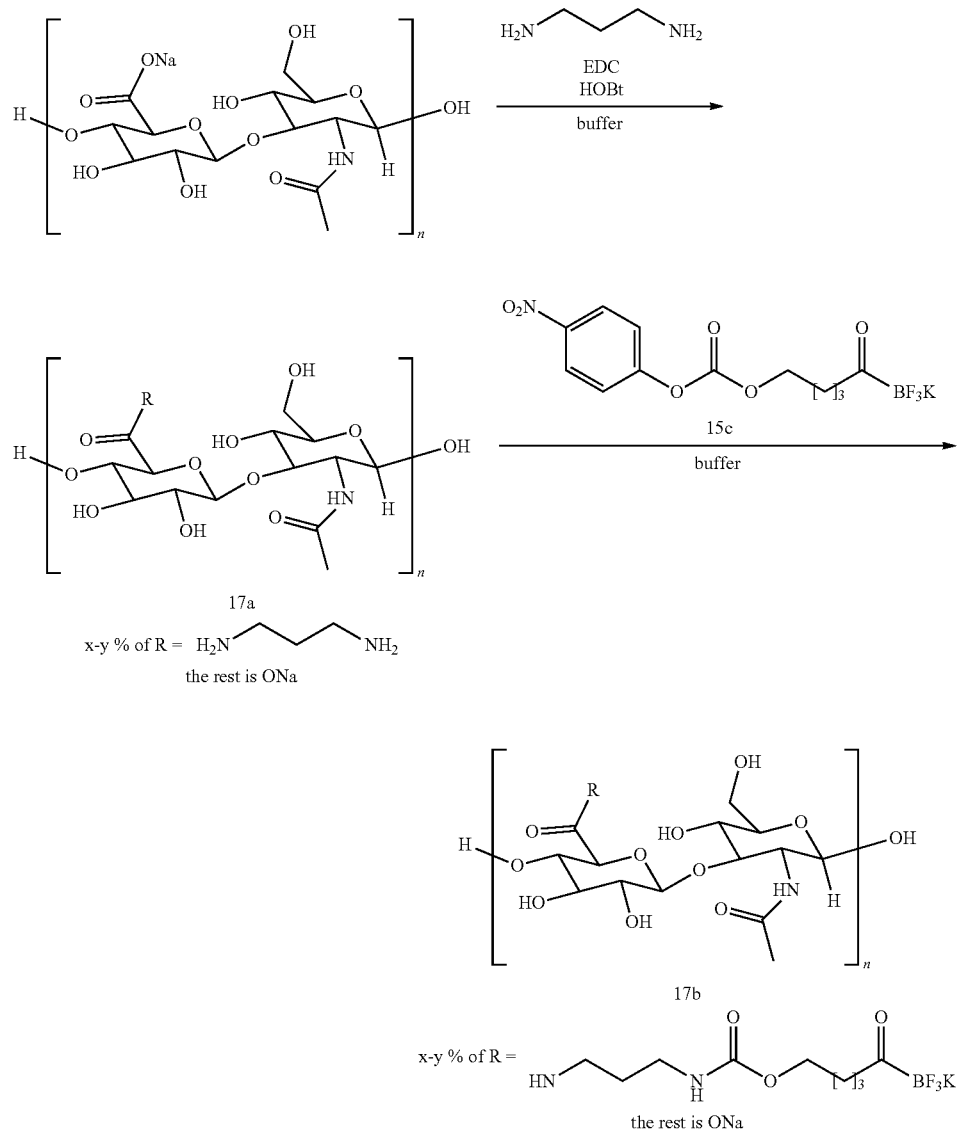

Hyaluronic acid sodium salt (116 kDa, 1.00 g; 2.49 mmol; 1 eq.) was dissolved in a solution of 0.4 M 1.3-diaminopropane in 100 mM MES buffer (pH 5.5, 125 mL) under vigorous stirring. To the clear, colorless and viscous solution HOBt (1.15 g; 7.48 mmol; 3.00 eq.) was added. The mixture was treated in an ultrasonic bath until all lumps moldered and a grey suspension was formed. EDC.HCl (98.48 mg; 513.72 µmol; 0.21 eq.) was added. Upon dissolution of the carbodiimide, the suspension was stirred at room temperature overnight. Sodium acetate trihydrate (16.97 g; 124.69 mmol; 50.00 eq.) was added and a colorless, viscous and clear solution was formed immediately. After sodium acetate trihydrate dissolved completely, the solution was partitioned between fourteen 50 mL Falcon tubes (10 mL each). The HA was precipitated by addition of absolute EtOH (ad 50 mL). The tubes were closed, vigorously shaken and centrifuged at 8000 rpm for 3 minutes. After discarding the supernatant, the pellets were successively washed with EtOH, combined and dried under high vacuum. The obtained white pellets were dissolved in water (80.00 mL) to yield a clear, colorless and viscous solution. To this solution 4 M NaOH (26.62 mL) was added stirred at room temperature. Acetic acid (6.09 mL) was added, the pH was checked with pH-paper: pH 8.5 and the solution was filtered through a 150 mL bottletop filter into a 150 mL Corning bottle. The filtered solution was partitioned between eleven 50 mL Falcon tubes (10 mL each). The HA was precipitated by addition of absolute EtOH (ad 50 mL). The tubes were closed, vigorously shaken and centrifuged at 8000 rpm for 3 minutes. After discarding the supernatant, the obtained white pellets were washed with EtOH. After discarding the supernatant, the pellets were combined and dried under high vacuum to yield 17a.

Yield: 905 mg; 90%, white powder.

Amine content: 0.083 mmol/g.

Accordingly, hyaluronic acids with up to 60% derivatization can be synthesized.

Aminofunctionalized HA 17a (1 eq) is dissolved in buffer (pH 8). Compound 15c (5 eq) is added and the reaction mixture is stirred at room temperature until sufficient conversion is observed. KAT functionalized HA 17b is purified by precipitation.

Example 18

Synthesis of PA-Hydroxylamine Reagent 18

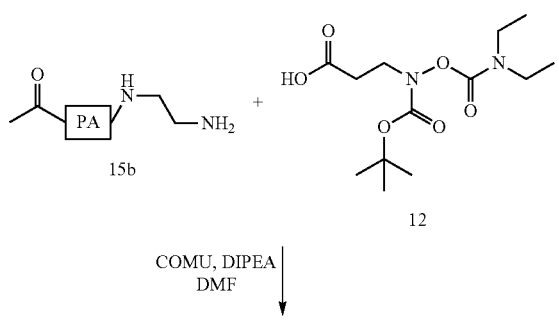

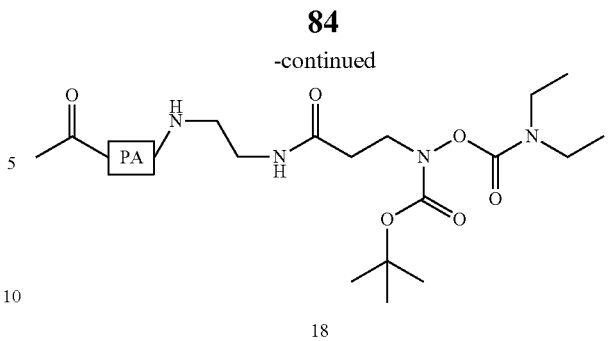

Polymer 15b (1 eq), carboxylic acid 12 (2 eq) and COMU (2 eq) are dissolved in DMF. DIPEA (4 eq) is added and the reaction mixture is stirred at room temperature. After full conversion was detected by LCMS, polymer 18 was purified by preparative HPLC.

Example 19

Synthesis of HA-Hydroxylamine Reagent 19

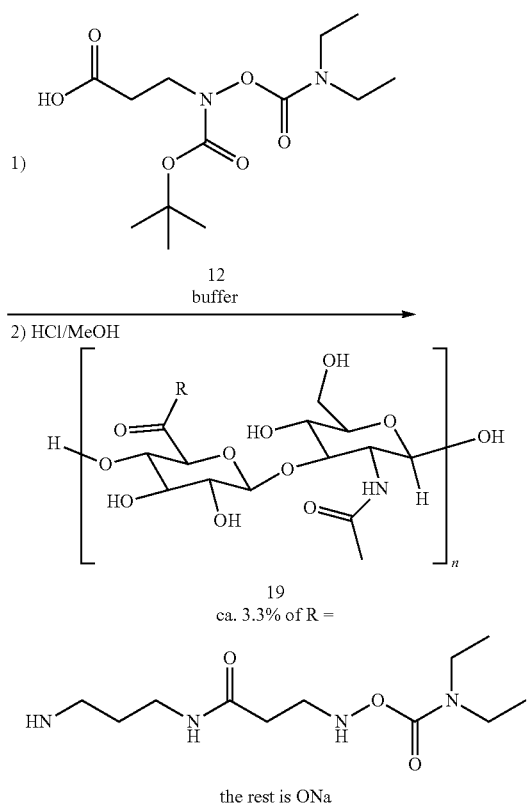

Hyaluronic acid 17a (1 eq), carboxylic acid 12 (0.3 eq), EDC.HCl (0.3 eq) and HOBt (3 eq) are stirred in MES buffer (pH 5.5) overnight. The functionalized HA intermediate is purified by precipitation.

Functionalized HA (228.00 mg; 1 eq.) is dissolved in water (11.40 ml) in a 50 ml-Falcon tube under vigorous shaking to yield a viscous solution (2% w/v HA) within 3.5 hours. TFA (3.80 ml; 0.05 mol; 88.96 eq.) is added to the HA solution and the reaction mixture is shaken vigorously. After 60 minutes the HA is precipitated from the viscous solution by addition of acetone. The precipitate is washed with EtOH and dried under high vacuum to yield 19.

Reagents 18 and 19 can be used to attach polymers to KAT functionalized linker-drug conjugates. If these linkers are designed to be cleavable (as in example 5), large prodrugs with extended plasma half-lives are formed.

ABBREVIATIONS

Ac acetyl
Ac-PA N-terminal acetylated polypeptide containing proline and alanine residues
ACN acetonitrile
aq. aqueous
Asp aspartate
Bn benzyl
Boc tert-butyloxycarbonyl
Bzl benzyl
Cbz benzyloxycarbonyl
CNP C-type natriuretic peptide
COMU (1-Cyano-2-ethoxy-2-oxoethylidenaminooxy)dimethylamino-morpholino-carbenium hexafluorophosphate
DBU 1,8-diazabicyclo (5.4.0)undec-7-ene
DCM dichloromethane
DIPEA diisopropylethylamine
DMAP dimethylaminopyridine
DMF dimethylformamide
eq equivalent
EDC 1-ethyl-3-(3-dimethylaminopropyl)carbodiimide
EDTA ethylene diamine tetraacetic acid
Et ethyl
Fmoc fluorenylmethyloxycarbonyl
GRF growth hormone-releasing factor
GP(80) glycine proline polypeptide (number of amino acids indicated in bracket)
HA hyaluronic acid
HOBt 1-hydroxybenzotriazole
HPLC high performance liquid chromatography
KAT potassium acyltrifluoroborate
LC liquid chromatography
LCMS liquid chromatography mass spectrometry
Lys lysine
Me methyl
MeOH methanol
MeCN acetonitrile
MES 2-(N-morpholino)ethanesulfonic acid
MTBE methyl-tert-butylether
MWCO molecular weight cut-off
MS mass spectrum/mass spectrometry
NHS N-hydroxysuccinimide
NMP N-methyl-2-pyrrolidone
OxymaPure ethyl-(hydroxyimino)cyanoacetate
PA proline/alanine polypeptide
PEG polyethylene glycol
pNP para-nitrophenyl
PyBOP benzotriazol-1-yl-oxytripyrrolidinophosphonium hexafluorophosphate
RP reversed phase
sat. saturated
SEC size exclusion chromatography
TBTU N,N,N',N'-tetramethyl-O-(benzotriazol-1-yl)uronium tetrafluoroborate
$T_3P$ 2,4,6-tripropyl-1,3,5,2,4,6-trioxatriphosphorinane-2,4,6-trioxide
tBu and t-Bu tert-butyl
TES triethylsilane
TFA trifluoroacetic acid
TFE trifluoroethanol
THF tetrahydrofuran
TLC thin layer chromatography
Tmob 2,4,6-trimethoxybenzyl
UPLC ultra performance liquid chromatography

---

The invention claimed is:

1. A compound of formula (I)

$$D\text{-}(L^1\text{-}L^2\text{-}A)_a \quad (I),$$

wherein

-D is drug moiety;

each -$L^1$- is independently a reversible prodrug linker, which is covalently conjugated to -D through a reversible linkage that is cleavable in the absence of enzymes in aqueous buffer at pH 7.4 and 37° C.;

each -$L^2$- is independently a chemical bond or a spacer;

each -A is —$X^0$ or —$Y^0$;

a is selected from the group consisting of 1, 2, 3, 4, 5, 6, 7 and 8;

—$X^0$ is a substituted acyl borate; and

—$Y^0$ is a substituted hydroxylamine.

2. The compound of claim 1, wherein -D is selected from the group consisting of small molecule drug moieties, oligonucleotide moieties, peptide nucleic acid moieties, peptide moieties and protein moieties.

3. The compound of claim 2, wherein -$L^1$- is of formula (a-i):

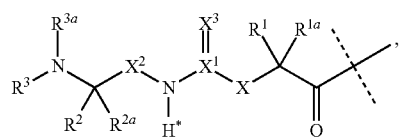

(a-i)

wherein the dashed line indicates the attachment to a primary or secondary amine of -D by forming an amide bond;

—X— is —C($R^4R^{4a}$)—; —N($R^4$)—; —O—; —C($R^4R^{4a}$)—C($R^5R^{5a}$)—; —C($R^5R^{5a}$)—C($R^4R^{4a}$)—; —C($R^4R^{4a}$)—N($R^6$)—; —N($R^6$)—C($R^4R^{4a}$)—; —C($R^4R^{4a}$)—O—; —O—C($R^4R^{4a}$)—; or —C($R^7R^{7a}$)—;

>$X^1$= is C; or S(O);

—$X^2$— is —C($R^8R^{8a}$)— or —C($R^8R^{8a}$)—C($R^9R^{9a}$)—;

=$X^3$ is =O; =S; or =N—CN;

—$R^1$, —$R^{1a}$, —$R^2$, —$R^{2a}$, —$R^4$, —$R^{4a}$, —$R^5$, —$R^{5a}$, —$R^6$, —$R^8$, —$R^{8a}$, —$R^9$, —$R^{9a}$ are independently selected from the group consisting of —H and $C_{1-6}$ alkyl;

—$R^3$, —$R^{3a}$ are independently selected from the group consisting of —H and $C_{1-6}$ alkyl, provided that in case one of —$R^3$, —$R^{3a}$ or both are other than —H they are connected to N to which they are attached through a $sp^3$-hybridized carbon atom;

—$R^7$ is —N($R^{10}R^{10a}$); or —$NR^{10}$—(C=O)—$R^{11}$;

—$R^{7a}$, —$R^{10}$, —$R^{10a}$, —$R^{11}$ are independently of each other —H; or $C_{1-6}$ alkyl;

optionally, one or more of the pairs —$R^{1a}$/—$R^{4a}$, —$R^{1a}$/—$R^{5a}$, —$R^{1a}$/—$R^{7a}$, —$R^{4a}$/—$R^{5a}$, —$R^{8a}$/$R^{9a}$ form a chemical bond;

optionally, one or more of the pairs —R/—$R^{1a}$, —$R^2$/—$R^{2a}$, —$R^4$/—$R^{4a}$, —$R^5$/—$R^{5a}$, —$R^8$/—$R^{8a}$, —$R^9$/—$R^{9a}$ are joined together with the atom to which they are attached to form a $C_{3-10}$ cycloalkyl; or 3- to 10-membered heterocyclyl;

optionally, one or more of the pairs —$R^1$/—$R^4$, —$R^1$/—$R^5$, —$R^1$/—$R^6$, —$R^1$/—$R^{7a}$, —$R^4$/—$R^5$, —$R^4$/—$R^6$, —$R^8$/—$R^9$, —$R^2$/—$R^3$ are joined together with the atoms to which they are attached to form a ring $A^0$;

optionally, $R^3$/$R^{3a}$ are joined together with the nitrogen atom to which they are attached to form a 3- to 10-membered heterocycle;

$A^0$ is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and wherein -$L^1$- is substituted with 1, 2, 3, 4, 5, 6, 7 or 8 moieties of -$L^2$-A and wherein -$L^1$- is optionally further substituted, provided that the hydrogen marked with the asterisk in formula (a-i) is not replaced by -$L^2$-A or a substituent.

4. A compound of formula (II)

$$Z-(L^{2'}-B^0)_b \quad (II),$$

wherein
—Z is a carrier comprising a $C_{8-24}$ alkyl moiety or a polymeric moiety;
-$L^{2'}$- is a chemical bond or a spacer;
—$B^0$ is —$Y^0$;
b is an integer of at least 1; and
—$Y^0$ is a substituted hydroxylamine.

5. The compound of claim 4, wherein —Z comprises a PEG-based polymer.

6. The compound of claim 4, wherein —Z comprises a hyaluronic acid-based polymer.

7. The compound of claim 4, wherein b is selected from the group consisting of 1, 2, 3, 4, 5, 6, 7, 8, 9, 10, 11 and 12.

8. The compound claim 1 or 4, wherein -$L^2$- and -$L^{2'}$- are selected from the group consisting of -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^3$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^4$)($R^{y4a}$)—, —N($R^{y4}$)C(O)N($R^{y4a}$)— and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

each —$R^{y2}$ is independently selected from the group consisting of halogen, —CN, oxo(=O), —COO$R^{y5}$, —O$R^{y5}$, —C(O)$R^{y5}$, —C(O)N($R^{y5}R^{y5a}$), —S(O)$_2$N($R^{y5}R^{y5a}$), —S(O)N($R^{y5}R^{y5a}$), —S(O)$_2R^{y5}$, —S(O)$R^{y5}$, —N($R^{y5}$)S(O)$_2$N($R^{y5a}R^{y5b}$), —S$R^{y5}$, —N($R^{y5}R^{y5a}$), —NO$_2$, —OC(O)$R^{y5}$, —N($R^{y5}$)C(O)$R^{y5a}$, —N($R^{y5}$)S(O)$_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$ —$R^{y5a}$ and —$R^{y5b}$ is independently selected from the group consisting of —H, and $C_{1-6}$ alkyl, wherein $C_{1-6}$ alkyl is optionally substituted with one or more halogen, which are the same or different.

9. The compound of claim 8, wherein -$L^2$- and -$L^{2'}$- are selected from the group consisting of $C_{1-10}$ alkyl, phenyl, naphthyl, azulenyl, indenyl, indanyl, $C_{3-10}$ cycloalkyl, 3- to 10-membered heterocyclyl and -A is —$X^0$.

10. The compound of claim 9, wherein -$L^2$- and -$L^{2'}$- are selected from $C_{1-10}$ alkyl and phenyl.

11. The compound of claim 8, wherein -$L^2$- and -$L^{2'}$- are $C_{1-10}$ alkyl and -A is —$Y^0$.

12. The compound of claim 11, wherein -$L^2$- and -$L^{2'}$- are $C_6$ alkyl.

13. The compound of claim 10, wherein —$X^0$ is of formula (III)

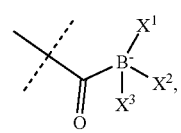

(III)

wherein
the dashed line indicates attachment to -$L^2$- or -$L^{2'}$-, respectively;
—$X^1$, —$X^2$ and —$X^3$ are independently of each other selected from the group consisting of —F, —OR, —$N^+R_3$, —$N^+R_2$OR, —$N^+R_2$SR and —$N^+R_2NR_2$;
each —R is independently selected from the group consisting of —H, -$T^0$, $C_{1-50}$ alkyl, $C_{2-50}$ alkenyl, and $C_{2-50}$ alkynyl; wherein -$T^0$, $C_{1-50}$ alkyl, $C_{2-50}$ alkenyl, and $C_{2-50}$ alkynyl are optionally substituted with one or more —$R^{x1}$, which are the same or different and wherein $C_{1-50}$ alkyl, $C_{2-50}$ alkenyl, and $C_{2-50}$ alkynyl are optionally interrupted by one or more groups selected from the group consisting of -$T^0$-, —C(O)O—, —O—, —C(O)—, —C(O)N($R^{x2}$)—, —S(O)$_2$N($R^{x2}$)—, S(O)N($R^{x2}$), —S(O)$_2$—, —S(O)—, —N($R^{x2}$)S(O)$_2$N($R^{x2a}$)—, —S—, —N($R^{x2}$)—, —OC(O$R^{x2}$)($R^{x2a}$), —N($R^{x2}$)C(O)N($R^{x2a}$)—, and —OC(O)N($R^{x2}$)—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 30-membered heteropolycyclyl; wherein each $T^0$ is independently optionally substituted with one or more —$R^{x1}$, which are the same or different;

each —$R^{x1}$ is independently selected from the group consisting of halogen, -$T^0$, —CN, oxo (=O), —CO-O$R^{x3}$, —O$R^{x3}$, —C(O)$R^{x3}$, —C(O)N($R^{x3}R^{x3a}$), —S(O)$_2$N($R^{x3}R^{x3a}$), —S(O)N($R^{x3}R^{x3a}$), —S(O)$_2R^{x3}$, —S(O)$R^{x3}$, —N($R^{x3}$)S(O)$_2$N($R^{x3a}R^{x3b}$), —S$R^{x3}$, —N($R^{x3}R^{x3a}$), —NO$_2$, —OC(O)$R^{x3}$, —N($R^{x3}$)C(O)$R^{x3a}$, —N($R^{x3}$)S(O)$_2R^{x3a}$, —N($R^{x3}$)S(O)$R^{x3a}$, —N($R^{x3}$)C(O)O$R^{x3a}$, —N($R^{x3}$)C(O)N($R^{x3a}R^{x3b}$), —OC(O)N($R^{x3}R^{x3a}$), and $C_{1-6}$ alkyl; wherein $C_{1-6}$ alkyl is optionally substituted with one or more halogen, which are the same or different;

each —$R^{x2}$, —$R^{x2a}$, —$R^{x3}$, —$R^{x3a}$, $R^{x3b}$ is independently selected from the group consisting of —H and $C_{1-6}$ alkyl; wherein $C_{1-6}$ alkyl is optionally substituted with one or more halogen, which are the same or different;

optionally, two or three of —$X^1$, —$X^2$ and —$X^3$ are joined together with the atom to which they are attached to form a ring $A^0$;

$A^0$ is selected from the group consisting of 3- to 10-membered heterocyclyl and 8- to 30-membered heteropolycyclyl.

14. The compound of claim 13, wherein —$X^1$, —$X^2$ and —$X^3$ are —F.

15. The compound of claim 12, wherein each —$Y^0$ is independently of formula (IV)

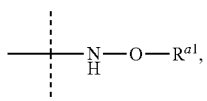
(IV)

wherein
the dashed line indicates attachment to -$L^2$- or -$L^{2'}$-, respectively;
—$R^{a1}$ is selected from the group consisting of —COO$R^{x1}$, —O$R^{x1}$, —C(O)$R^{x1}$, —C(O)N($R^{x1}R^{x1a}$), —S(O)$_2$N($R^{x1}R^{x1a}$), —S(O)N($R^{x1}R^{x1a}$), —S(O)$_2R^{x1}$, —S(O)$R^{x1}$, —S(O)$_2$O$R^{x1}$, —N($R^{x1}R^{x1a}$), -$T^0$, $C_{1-20}$ alkyl, $C_{2-20}$ alkenyl, and $C_{2-20}$ alkynyl; wherein -$T^0$, $C_{1-20}$ alkyl, $C_{2-20}$ alkenyl, and $C_{2-20}$ alkynyl are optionally substituted with one or more —$R^{x2}$, which are the same or different and wherein $C_{1-20}$ alkyl, $C_{2-20}$ alkenyl, and $C_{2-20}$ alkynyl are optionally interrupted by one or more groups selected from the group consisting of -$T^0$-, —C(O)O—, —O—, —C(O)—, —C(O)N($R^{x3}$)—, —S(O)$_2$N($R^{x3}$)—, —S(O)N($R^{x3}$)—, —S(O)$_2$—, —S(O)—, —N($R^{x3}$)S(O)$_2$N($R^{x3a}$)—, —S—, —N($R^{x3}$)—, —OC(O$R^{x3}$)($R^{x3a}$)—, —N($R^{x3}$)C(O)N($R^{x3a}$)—, and —OC(O)N($R^{x3}$)—;
—$R^{x1}$, —$R^{x1a}$, —$R^{x1b}$ are independently of each other selected from the group consisting of —H, -$T^0$, $C_{1-10}$ alkyl, $C_{2-10}$ alkenyl, and $C_{2-10}$ alkynyl; wherein -$T^0$, $C_{1-10}$ alkyl, $C_{2-10}$ alkenyl, and $C_{2-10}$ alkynyl are optionally substituted with one or more —$R^{x2}$, which are the same or different and wherein $C_{1-10}$ alkyl, $C_{2-10}$ alkenyl, and $C_{2-10}$ alkynyl are optionally interrupted by one or more groups selected from the group consisting of -$T^0$-, —C(O)O—, —O—, —C(O)—, —C(O)N($R^{x3}$)—, —S(O)$_2$N($R^{x3}$)—, —S(O)N($R^{x3}$)—; —S(O)$_2$—, —S(O)—, —N($R^{x3}$)S(O)$_2$N($R^{x3a}$)—, —S—, —N($R^{x3}$)—, —OC(O$R^{x3}$)($R^{x3a}$)—, —N($R^{x3}$)C(O)N($R^{x3a}$)—, and —OC(O)N($R^{x3}$)—;
each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{x2}$, which are the same or different;
each —$R^{x2}$ is independently selected from the group consisting of halogen, -$T^0$, —CN, oxo(=O), —COO$R^{x4}$, —O$R^{x4}$, —C(O)$R^{x4}$, —C(O)N($R^{x4}R^{x4a}$), —S(O)$_2$N($R^{x4}R^{x4a}$), —S(O)N($R^{x4}R^{x4a}$), —S(O)$_2R^{x4}$, —S(O)$R^{x4}$, —N($R^{x4}$)S(O)$_2$N($R^{x4a}R^{x4b}$), —S$R^{x4}$, —N($R^{x4}R^{x4a}$), —NO$_2$, —OC(O)$R^{x4}$, —N($R^{x4}$)C(O)$R^{x4a}$, —N($R^{x4}$)S(O)$_2R^{x4a}$, —N($R^{x4}$)S(O)$R^{x4a}$, —N($R^{x4}$)C(O)O$R^{x4a}$, —N($R^{x4}$)C(O)N($R^{x4a}R^{x4b}$), —OC(O)N($R^{x4}R^{x4a}$), and $C_{1-4}$ alkyl; wherein $C_{1-4}$ alkyl is optionally substituted with one or more halogen, which are the same or different;
each —$R^{x3}$, —$R^{x3a}$, —$R^{x4}$, —$R^{x4a}$, —$R^{x4b}$ is independently selected from the group consisting of —H and $C_{1-4}$ alkyl; wherein $C_{1-4}$ alkyl is optionally substituted with one or more halogen, which are the same or different.

16. The compound of claim 15, wherein —$R^{a1}$ of formula (IV) is selected from the group consisting of methyl, ethyl, propyl,

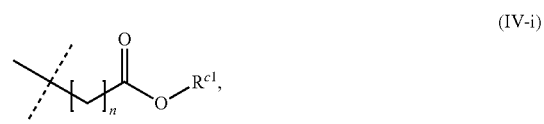
(IV-i)

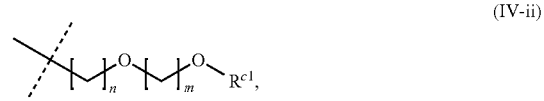
(IV-ii)

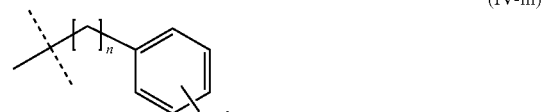
(IV-iii)

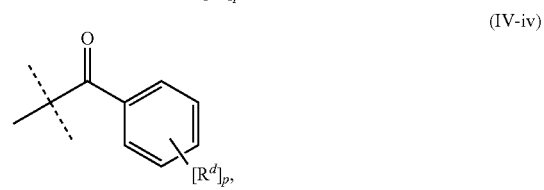
(IV-iv)

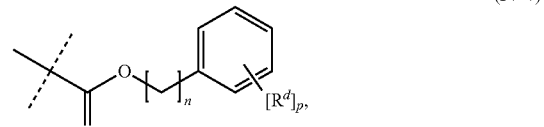
(IV-v)

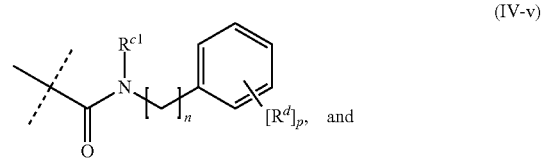
(IV-v)

(IV-vi)

wherein
—$R^{c1}$ and —$R^{c1a}$ are independently of each other selected from the group consisting of —H, -$T^0$ and $C_{1-6}$ alkyl;
—$R^d$ is selected from the group consisting of $C_{1-6}$ alkyl and —NO$_2$, —CN, —C(O)O$R^e$, —S(O)$_2$O$R^e$;
each -$T^0$ is independently of each other selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each -$T^0$ is independently optionally substituted with one or more —$R^e$, which are the same or different;
each —$R^e$ is independently $C_{1-6}$ alkyl;
n is selected from the group consisting of 0, 1, 2, 3, 4, 5, 6, 7, 8, 9 and 10;
m is selected from the group consisting of 1, 2, 3, 4, 5, 6, 7, 8, 9 and 10; and
p is selected from the group consisting of 0, 1, 2, 3, 4 and 5.

17. The compound of claim 16, wherein —$R^{a1}$ is

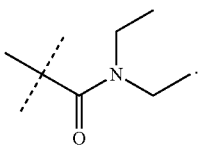

18. A method of synthesizing a carrier-linked prodrug, the method comprising the step of reacting a compound of formula (I)

$$D\text{-}(L^1\text{-}L^2\text{-}A)_a \quad (I),$$

wherein
-D is a drug moiety;
each -$L^1$- is independently a reversible prodrug linker, which is covalently conjugated to -D through a reversible linkage that is cleavable in the absence of enzymes in aqueous buffer at pH 7.4 and 37° C.;
each -$L^2$- is independently a chemical bond or a spacer;
each -A is —$X^0$ or —$Y^0$;
a is selected from the group consisting of 1, 2, 3, 4, 5, 6, 7 and 8;
—$X^0$ is a substituted acyl borate; and
—$Y^0$ is a substituted hydroxylamine;

under aqueous conditions with a compound of formula (II)

$$Z\text{-}(L^{2'}\text{-}B^0)_b \quad (II),$$

wherein
—Z is a carrier comprising a $C_{8-24}$ alkyl moiety or a polymeric moiety;
-$L^{2'}$- is a chemical bond or a spacer;
—$B^0$ is —$Y^0$;
b is an integer of at least 1; and
—$Y^0$ is a substituted hydroxylamine;
with -A being —$X^0$ and —$B^0$ being —$Y^0$, and forming an amide bond between moiety -A and a moiety —$B^0$.

19. The method of claim 18, wherein the method is performed at a pH ranging from and including 1 to 8.

20. The method of claim 19, wherein the method is performed at a pH ranging from and including 3 to 5.

21. The method of claim 18, wherein the method is conducted in an aqueous buffer.

22. The method of claim 18, wherein the reaction is conducted in a solvent mixture selected from the group consisting of THF/$H_2O$, $CH_3CN$/$H_2O$, tBuOH/$H_2O$ and DMSO/tBuOH/$H_2O$.

23. The method of claim 22, wherein the method of the present invention is performed for 1 minute to 5 hours.

24. The method of claim 21, wherein the aqueous buffer comprises additives.

* * * * *

UNITED STATES PATENT AND TRADEMARK OFFICE
CERTIFICATE OF CORRECTION

PATENT NO. : 11,896,671 B2
APPLICATION NO. : 16/317689
DATED : February 13, 2024
INVENTOR(S) : Nicola Bisek et al.

It is certified that error appears in the above-identified patent and that said Letters Patent is hereby corrected as shown below:

On the Title Page

Right column, item (56) under the Foreign Patent Documents section, third reference from the bottom, please replace "WO2015/104374" with "WO 2015/104374".

Right column, item (56) under the Other Publications section, first reference, please replace "J'nal of the ACS" with "Journal of the American Chemical Society".

Right column, item (56) under the Other Publications section, third reference, please replace "Hheridia" with "Heredia".

Right column, item (56) under the Other Publications section, sixth reference, please replace "Herdia" with "Heredia".

Right column, item (56) under the Other Publications section, sixth reference, please replace "Aminoxy" with "Aminooxy".

Right column, item (56) under the Other Publications section, seventh reference, please delete "Hideotoshi".

Right column, item (56) under the Other Publications section, seventh reference, please replace "Joumal" with "Journal".

On page 2, left column, item (56) under the Other Publications section, first reference, please replace "Wiley-VCHH" with "Wiley-VCH".

In the Claims

At Column 87, Claim number 1, Line number 34, please replace "is drug" with "is a drug".

Signed and Sealed this
Seventh Day of May, 2024

Katherine Kelly Vidal
*Director of the United States Patent and Trademark Office*

CERTIFICATE OF CORRECTION (continued)
U.S. Pat. No. 11,896,671 B2

At Column 88, Claim number 3, Line numbers 39 and 40, please replace "a sp$^3$-hybridized" with "an sp$^3$-hybridized".

At Column 88, Claim number 3, Line number 45, please replace "-R$^{8a}$/R$^{9a}$" with "-R$^{8a}$/-R$^{9a}$".

At Column 88, Claim number 3, Line number 47, please replace "-R/-R$^{1a}$" with "-R$^1$/-R$^{1a}$".

At Column 88, Claim number 3, Line number 56, please replace "R$^3$/R$^{3a}$" with "-R$^3$/R$^{3a}$-".

At Column 90, Claim number 10, Line numbers 8 and 9, please replace "selected from" with "selected from the group consisting of".

At Column 90, Claim number 13, Line number 61, please replace "R$^{x3b}$" with "-R$^{x3b}$".